(12) United States Patent
Bishop et al.

(10) Patent No.: US 11,344,572 B2
(45) Date of Patent: May 31, 2022

(54) METHODS FOR PRODUCING ULTRAPURE WATER THAT GENERATES INCREASED CELLULAR PERMEATION

(71) Applicant: HYDROSOME HOLDINGS, LLC, Tampa, FL (US)

(72) Inventors: Patrick Charles Bishop, Hoover, AL (US); Sean Bryan Gill, Lithia, FL (US)

(73) Assignee: HYDROSOME HOLDINGS, LLC, Tampa, FL (US)

( * ) Notice: Subject to any disclaimer, the term of this patent is extended or adjusted under 35 U.S.C. 154(b) by 0 days.

(21) Appl. No.: 17/386,150

(22) Filed: Jul. 27, 2021

(65) Prior Publication Data

US 2021/0353667 A1 Nov. 18, 2021

Related U.S. Application Data

(63) Continuation of application No. 16/350,259, filed on Oct. 20, 2018, now abandoned.

(51) Int. Cl.
*A61K 33/00* (2006.01)
*C02F 9/00* (2006.01)
(Continued)

(52) U.S. Cl.
CPC .............. *A61K 33/00* (2013.01); *A23L 2/52* (2013.01); *A61L 2/0047* (2013.01); *C02F 1/68* (2013.01);
(Continued)

(58) Field of Classification Search
CPC ......... A61K 33/00; A23L 2/52; A61L 2/0047; A61L 2202/21; C02F 1/68; C02F 9/00; C02F 1/001
See application file for complete search history.

(56) References Cited

U.S. PATENT DOCUMENTS

| | | | |
|---|---|---|---|
| 5,435,913 A * | 7/1995 | Ashbrook | ................. A61L 2/02 210/188 |
| 6,521,248 B1 | 2/2003 | Holloway et al. | |

(Continued)

FOREIGN PATENT DOCUMENTS

WO      2018179495 A1     10/2018

OTHER PUBLICATIONS

The Declaration of Michael Raymond Cary Regarding Public Use and Public Availability of Inventions Claimed in U.S. Appl. No. 16/421,163 (Year: 2020).*

(Continued)

*Primary Examiner* — Anshu Bhatia
(74) *Attorney, Agent, or Firm* — Morgan, Lewis & Bockius LLP; Christopher J. Betti

(57) ABSTRACT

The invention relates to products by processes, product compositions, product formulations and product uses that are all related to reduced ultrapure water cluster sizes in an aqueous composition containing a non-$H_2O$ substance in the reduced size water clusters in order to improve bioavailability of the aqueous composition. The invention processes use higher flow rate of the blended aqueous composition from a jet openings of a nozzle inside the hollow cylinder to reduce sizes of the ultrapure water clusters in the blended aqueous composition of the non-$H_2O$ substance to less than 300 nanometers.

17 Claims, 21 Drawing Sheets

(51) Int. Cl.
| | |
|---|---|
| C02F 1/68 | (2006.01) |
| A23L 2/52 | (2006.01) |
| A61L 2/00 | (2006.01) |
| C02F 1/00 | (2006.01) |
| C02F 1/28 | (2006.01) |
| C02F 1/32 | (2006.01) |
| C02F 1/44 | (2006.01) |
| C02F 1/469 | (2006.01) |
| C02F 101/12 | (2006.01) |
| C02F 103/04 | (2006.01) |

(52) U.S. Cl.
CPC ............ *C02F 9/00* (2013.01); *A23V 2002/00* (2013.01); *A61L 2202/21* (2013.01); *C02F 1/001* (2013.01); *C02F 1/283* (2013.01); *C02F 1/32* (2013.01); *C02F 1/441* (2013.01); *C02F 1/4695* (2013.01); *C02F 2101/12* (2013.01); *C02F 2103/04* (2013.01); *C02F 2209/05* (2013.01)

(56) References Cited

U.S. PATENT DOCUMENTS

| | | |
|---|---|---|
| 7,832,920 B2 | 11/2010 | Wood et al. |
| 8,193,251 B2 | 6/2012 | Lo et al. |
| 8,623,212 B2 | 1/2014 | Irvin, Sr. et al. |
| 9,474,991 B2 | 10/2016 | Irvin, Sr. et al. |
| 2005/0031657 A1 | 2/2005 | Gilson et al. |
| 2007/0186367 A1 | 8/2007 | Field et al. |
| 2011/0218251 A1 | 9/2011 | Lo et al. |
| 2012/0039951 A1 | 2/2012 | Watson et al. |
| 2017/0290854 A1* | 10/2017 | Matlick ............... A61K 9/08 |

OTHER PUBLICATIONS

Dary, Mark, LinkedIn profile, Nov. 27, 2021 (7 pages).
Rish, Michelle, LinkedIn profile, Nov. 27, 2021 (5 pages).
Declaration of Michael Raymond Cary Regarding Public Use and Public Availability mailed Oct. 15, 2020. (Year: 2020).
Second Declaration Of Michael Raymond Cary Regarding Public Use And Public Availability Of Inventions Claimed in U.S. Appl. No. 16/421,163, dated May 23, 2019, 36 pages.
Krishan, Awtar, Rapid flow cytofluorometric analysis of mammalian cell cycle by propidium iodide staining, The Journal of Cell Biology, 1975, pp. 188-193, vol. 66.
Keutsch, Frank N., Saykally Richard J., Wather clusters: untangling the mysteries of the liquid, one molecule at a time, PNAS. Sep. 1, 2001, pp. 10533-10540, vol. 98(19).
Eaves, J.D., Loparo, J.J., et al. Hydrogen bonds in liquid water are broken only fleetingly, PNAS, Sep. 13, 2005, pp. 13019-13022, vol. 102(37).
Plumridge, T.H., Waigh, R.D., Water structure theory and some implications for drug design, JPP, 2002, pp. 1155-1179, vol. 54.
Smith, Jared D. et al., Unified description of temperature-dependent hydrogen-bond rearrangements in liquid water, PNAS, Oct. 4, 2005, pp. 14171-14174, vol. 102(40).
Chaplin, Martin, Water's hydrogen bond strength, Jun. 10, 2007, pp. 1-20, Cornell University Library. Citation includes https://arxiv.org>condmat>arXiv:0707. 1355.
Peternelj, Andreja, Charge and size of particles in surface waters, Master's thesis, Jan. 2009, Lund University.
Shu, Li et al., Directly observe sodium chloride aggregates waltzing through dilute solutions, Solutions to Environ. Challenges Through Innovation in Research, 2013, p. 213-223.
Shirreffs, Susan M., Sawka, Michael N., Fluid and electrolyte needs for training, competition and recovery, Journal of Sports Sciences, 2011, pp. S39-S46, vol. 29(S1).
Tomaszewska et al., Detection Limits of DLS and UV-Vis spectroscopy in charact. of polydisperse nanoparticle colloid, Journal of Nanomaterials, 2013, Hindawi v.20/313081. 10 pgs.
Gravelle, Simon et al., Optimizing water permeability through the hourglass shape of aquaporins, PNAS, Oct. 8, 2013, pp. 16367-16372, vol. 110(41).
Stoyanov, Evgenii S. et al., The structure of the hydrogen ion (Haq+) in water, J Am Chem Soc., Feb. 10, 2010, pp. 1484-1485, vol. 132(5).
Del Giudice, Emilio et al., The origin and the special role of coherent water in living systems, Fields of the Cell, 2015, pp. 95-111.
Nestle Pure Life, Bottled Water Quality Report, REV Dec. 31, 2015, 14 pages, Nestle Waters North America Inc., 900 Long Ridge Rd., Stamford, CT 06902.
Dehydration, from Wikipedia the free encyclopedia on the internet, last edited Jan. 30, 2018, 5 pages.
Aquaporin, from Wikipedia the free encyclopedia on the internet, last edited on Jan. 31, 2018, 12 pages.
Purified water, from Wikipedia the free encyclopedia on the internet, last edited Feb. 8, 2018, 10 pages.
Water cluster, from Wikipedia the free encyclopedia and Wikivisually on the internet, last edited in 2018, 4 pages.
Declaration of Michael Raymond Cary regarding Public Use and Public Availability of Inventions claimed in U.S. Appl. No. 16/350,259, signed Oct. 15, 2020, 33 pages.
Declaration of Michael Raymond Cary regarding Public Use and Public Availability of Inventions claimed in U.S. Appl. No. 16/421,163, signed Oct. 15, 2020, 33 pages.
U.S. Appl. No. 62/675,248, filed May 23, 2018; titled "Methods for Making, Compositions, and Uses of Nano-Sized Particles for Improved Biological Transport".
U.S. Appl. No. 16/421,163, filed May 23, 2019; titled "Compositions Comprising a Solute Encapsulated by a Nanosized Water Cluster and Methods of Use Thereof".

* cited by examiner

METHODS FOR PRODUCING ULTRAPURE WATER THAT GENERATES INCREASED CELLULAR PERMEATION

CROSS-REFERENCE TO RELATED APPLICATIONS

The present application is a continuation of U.S. patent application Ser. No. 16/350,259, entitled "COMPOSITION COMPRISING AQUEOUS MEDIUM WITH REDUCED SIZE WATER CLUSTERS TO IMPROVE BIOAVAILABILITY OF THE AQUEOUS MEDIUM AND METHODS FOR MAKING AND USING THE COMPOSITIONS," filed on Oct. 20, 2018, all which is incorporated herein by reference in its entirety.

BACKGROUND OF THE INVENTION

The common 2D view of $H_2O$ is illustrated in FIG. 1 where two (2) hydrogen atoms 401, 404 are chemically bonded to one (1) oxygen atom 402 at a 106 angle to makes make a polar molecule with an electronic size (dashed line) of 0.28 by 0.32 nanometers. $H_2O$ is known to ionize to hydronium cations and hydroxonium anions ($OH^-$). The hydronium ion is often given the empirical molecular formula $H_3O^+$ and depicted in 2D as an oxygen atom 400 bonded to three hydrogen atoms 401, 402, and 403 with the dashed line 404 defining its 2D electronic size (see FIG. 4). The hydroxonium ion (traditionally called hydroxide ion with molecular formula $OH^-$) is depicted in FIG. 3 as an oxygen atom 301 and a hydrogen atom 302.

Each $H_2O$ molecule can form up to four hydrogen bonds in liquid water. FIG. 2 illustrates a hydrogen bond between two (2) water molecules. Oxygen atom 202 is hydrogen bonded to water molecule hydrogen atom 201. Most models for intermolecular water H-bonding would suggest that hydrogen atoms 203 and 204 would be also have formed hydrogen bonds with other $H_2O$ molecules at the same time. The hydrogen bond is generally considered to be a partial electrostatic attraction between a hydrogen which is bound to a more electronegative atom (the hydrogen atom donor) such a nitrogen, oxygen, or fluorine, and another atom bearing a lone pair of electrons (the hydrogen atom acceptor). The hydrogen bond's energy can vary greatly (between 1 and 40 kcal/mol) depending upon the donor atom donating the hydrogen atom and acceptor atom receiving the hydrogen atom to make the H-bond. Also the energy of an H-bond varies for the same type hydrogen bond as a function of the relative size of the water cluster of $H_2O$ molecules, a particular H-bond's conformation, geometry and needs for resonance delocalization of neighboring charges and radical free electrons, steric effects, electronic induction effects, and other H-bond network attraction, dipole, and opposition forces.

The H-bond has some features ascribed to covalent bonding such as the H-bond being a directional bond, can be a strong bond, and can produce interatomic distances shorter than the sum of the van der Waals radii. Note van der Waals radius is used to define half of the distance between the closest approach of two non-bonded atoms of a given element. Covalent characteristics of H-bonds are more substantial when acceptors bind hydrogens from more electronegative donors. For example, the acceptor atoms in the $H_2O$ molecule and in the $H_2S$ (hydrogen sulfide) molecule are oxygen and sulfur atoms respectively. $H_2O$ forms stronger intermolecular hydrogen bonds due to the higher electronegativity of the oxygen atom (in $H_2O$) compared to the lower electronegativity of the sulfur atom in hydrogen sulfide ($H_2S$) which forms weaker intermolecular hydrogen bonds. Consequently $H_2O$ has a higher melting temperature and a higher boiling temperature than $H_2S$ because $H_2O$ forms stronger intermolecular H-bonds. Thus at room temperature $H_2O$ is a liquid whereas $H_2S$ is a gas. H-bonds readily form between molecules of water, ice, ammonia, hydrogen sulfide, and many functionalized organic molecules for example where the functional group has a hydrogen atom bonded to a nitrogen or oxygen. Hydrogen bonds also can form between atoms in a single molecule are termed intramolecular hydrogen bonds. Many polynucleotides, proteins, drugs, and polymers form intramolecular hydrogen bonds and these bonds critically define or restrict secondary and tertiary structure conformations of these molecules. Below depicted in a simple way are five types of hydrogen bonds and their H-bond enthalpies (energy) which range in strength about 3.5 fold.

In the H-bond depictions below the H donor atom is on the left; the H-Bond is the dashed line, and the acceptor atom is depicted on the right.

| H-Bond | Enthalpy (kJ/mol) or (kcal/mol) units |
|---|---|
| O—H•••:N | 29 kJ/mol (= 6.9 kcal/mol), as for example with a hydrogen bond between a water molecule and an amine group molecule. |
| O—H•••:O | 21 kJ/mol (= 5.0 kcal/mol), as for example with a hydrogen bond between two water molecules. |
| HO—H•••:$OH+_3$ | 18 kJ/mol (= 4.3 kcal/mol) as for example with a hydrogen bond between a water molecule and a hydronium ion |
| N—H•••:N | 13 kJ/mol (= 3.1 kcal/mol), as for example with a hydrogen bond between two amine group molecules. |
| N—H•••:O | 8 kJ/mol (= 1.9 kcal/mol), as for example with a hydrogen bond between a water molecule and an amine group molecule. |

A model for a hydrogen ion by Stoyanov (2010) proposes that the hydrogen ion in water is a proton 502 clustered by six water molecules as depicted in FIG. 5 within circular dashed line 501. Structure inside the circular dashed line 501 for the hydronium ion has a molecular formula $H_{13}O_6^+$. Next to proton 502 is a water molecule that is hydrogen bonded to it by an oxygen atom 503 of another water molecule. Depicted hydrogen atom 504 which is of the same water molecule as oxygen atom 503, is itself hydrogen bonded to oxygen atom 507. Depicted hydrogen atom 505 which is of the same water molecule as oxygen atom 507, is itself hydrogen bonded to oxygen atom 506 of a water molecule which is depicted just on the perimeter of circular dashed line 501.

When X-ray (Morgan & Warren, 1938) and infrared studies (Magat 1936) on liquid water were first carried out, these studies suggested a liquid water structure model to Bernal & Fowler (1933) which called a uniform continuum model for liquid water. In this model, all oxygen atoms retain their four-coordination, but the hydrogen bonds are bent to such an extent that an instantaneous view from the central oxygen would see no order beyond the nearest neighbors. A random network model with soft hydrogen bonds suggested a water network with apex-linked polygons in rings of 4-, 5-, 6- or more-membered rings, similar to ices and clathrates, but randomly arranged (from Plumridge & Waigh, 2002).

Frank & Evans in 1945 introduced "the concept of icebergs induced in water by solute molecules or the mixture model of water." Using volume and entropy measurements to study effects of non-polar molecules dissolved in water (noble gases, CO, methane), they found that the non-polar molecules affected the water around them, making the water around them less dense, at a lower entropy, and less mobile than the bulk water. In other words, they found that the dissolution of small non-polar molecules in water made the water more structured. They postulated that perhaps some molecules could be added to water to make it act in the opposite way, namely less structured and more dense than bulk water.

In 1957, Frank & Wen postulated that the existence of long-lived structures in liquid water was not likely. They thought a more useful model might involve flickering clusters of hydrogen-bonded water molecules. Frank & Wen also classified ions that could behave in liquid water as either being structure makers or structure breakers. They suggested a mechanism for this which assumed the ion is surrounded by three concentric regions: an innermost ice-like region nearest the ion where all water molecules are immobilized by H-bonds; a second region in which water molecules are less ice-like; and the third region in which the influence of the ion on water molecules is weak (from Plumridge & Waigh, 2002).

The classification of ions and some polar molecules as a water structure-maker or a water structure-breaker was furthered by the observation that some ions/polar molecules stabilized ("kosmotropic") whereas some ions/polar molecules destabilized ("chaotropic") the native conformations of proteins, as assessed by enzyme activity, denaturation, temperature and solubility (Collins & Washabaugh 1985). These effects had additivity, for example a strongly denaturing (structure breaking) solute such as urea could be offset by adding a strongly stabilizing (structure making) solute such as trimethylamine oxide. Also two structure-breaking solutes would destabilize a protein structure more so than either one alone. The structure-making or structure-breaking action of solutes was quantifiable in aqueous solution by measuring either the change in aqueous medium viscosity (structure breakers lower it), or the rate of exchange of water molecules (structure breakers lower energy of activation), or the longitudinal relaxation rate of water molecules as measured by NMR (structure breakers increase the rate).

In 1986 Marcus proposed that the entropy of hydration was affected by the structure-making and structure solutes based on individual entropy contributions of 50 ions to causing compression, immobilization and electrostatic effects upon water structure. The Hofmeister ion series (1988) ranked ions based on their ability to precipitate hen egg-white proteins and Collins in 1997 demonstrated that the Hofmeister ions destabilizes the structure of other biological macromolecules in the same order. The Hoffmeister ion series shows opposite correlations for anions and cations with their degree of hydration. It turns out that structure-breaking ions destroy the hydrogen-bonded water network in a manner similar to increased temperature or pressure (Leberman & Soper 1995). It has been noticed that anions hydrate more strongly than cations of the same ionic radius and this is believed due to the fact that the partial-positive hydrogen atom of a water molecule can approach anions about 0.8 Å more closely than the partial negative oxygen atom of a water molecule. Note 10 Å (angstrom) is the same distance as 1 nanometer (nm). The hypothesis is (A) that small ions are strongly hydrated with small or negative hydration entropies creating local order, and (B) that large singly charged ions have larger positive entropies of hydration, and so act like hydrophobic molecules with their binding being dependent on van der Waals forces and their ion charge. The product of the measured viscosity and the measured conductivity at infinite dilution of a solution, has been used as a measure of a solute's water-structuring activity and is called the Walden product. This has been used to quantify structure-making and structure-breaking effects of amino acids, in conjunction with spectroscopic studies. Most anion forms of amino acids exhibit some structure-breaking activity. l-lysine, l-glutamic acid, l-aspartic acid and their salts show strong structure-breaking activity. Dextrose, however, behaves as a classic structure maker and reverses the structure-breaking action of l-lysine (Lutz et al 1994) (from Plumridge & Waigh, 2002).

Positive cooperative effects of hydrogen bonding in water are found and promote large tetrahedral networks of hydrogen-bonded water to form. Cooperative patterns were found in the first systematic studies of hydrogen bonding in carbohydrates (Jeffrey et al 1977). The water molecule acting as acceptor in a particular hydrogen bond will strengthen the other hydrogen bonds of the water molecule acting as a donor (Tombari et al., 1999). In 1998, Luck reported that in liquid water, hydrogen bonding cooperativity strengthens hydrogen bonds by up to 25 times the strength of the individual hydrogen bond in the water dimer (from Plumridge & Waigh, 2002).

Keutsch (2001) compiled data on hydrogen bond lengths in $H_2O$ dimers, trimers, tetramers, pentamers and hexamers using terahertz laser vibration-rotation-tunneling (VRT) spectra and mid-IR laser spectra. The obvious limitation of the Keutsch study is probably that he studied only UPW which is never the state of biological water. Keutsch hypothesized that the hydrogen bond (H-bond) in bulk water should be dominated by electrostatic interactions. Coulomb force, also called "electrostatic force" or Coulomb interaction, attraction or repulsion of particles or objects because of their electric charge . . . . Two like electric charges, both positive or both negative, repel each other along a straight line between their centers.

Keutsch also hypothesized that the hydrogen bond (H-bond) in bulk water should be balanced by the repulsive electron exchange. The consequence of the Pauli principle here is that electrons of the same spin are kept apart by a "repulsive electron exchange" interaction, which is a short-range effect, acting simultaneously with the long-range electrostatic or Coulombic force.

Keutsch further hypothesized that the hydrogen bond (H-bond) in bulk water should result in the dispersion force having a detectable effect. The London "dispersion force" is the weakest intermolecular force. The London dispersion force is a temporary attractive force that results when the electrons in two adjacent atoms occupy positions that make the atoms form temporary dipoles. This force is sometimes called an induced dipole-induced dipole attraction.

In addition, Keutsch hypothesized that the hydrogen bond (H-bond) in bulk water should cause induction (polarization) acting as the dominant many-body effect. Induction is a general phenomenon where charges are 'induced'(redistribution) in a body when another charged body is brought near it. Polarization is a vector quantity defined as the dipole moment per unit volume.

Keutsch measured the H-bond in the water dimer in terms of the oxygen-oxygen distance between the two water molecules to be 2.952 Å (0.295 nanometers). Note 10 Å (angstrom) is 1 nanometer (nm). Keutsch found that the water trimer is a much more rigid structure than the dimer, as the former has three strained H-bonds. The oxygen-oxygen distance of the H bond in the trimer is 2.85 Å, which is shorter than the H bond in the dimer, a result of the increased hydrogen bond strength caused by the cooperative effect of three-body forces. He found that the H-bonding motif of the water tetramer is similar to that of the trimer, with each monomer acting as a single donor and acceptor, and having one free and one bound H. He found that the average oxygen-oxygen distance in the tetramer is further shortened to 2.79 Å. The water pentamer was found to be similar to the trimer in both structure and dynamics. However, he found the pentamer ring is puckered with an oxygen-oxygen distance further shortened to 2.76 Å and having hydrogen bonds nearly linear in the axis of the two opposing oxygen atoms.

Keutsch reported that five-membered water molecule hydrogen bonded rings are a dominant topology in liquid water after running computer simulations of their molecular dynamics. He reported that the water hexamer represents a transition of a H-bond network from being two-dimensional to being most stably as a three-dimensional octahedral cage structure in which four of the water molecules are triple H-bonded, and two apical water molecules are double H-bonded. Thus Keutsch reported that $H_2O$ molecules in bulk liquid water are hydrogen bonded together to form $H_2O$ dimers, $H_2O$ trimers, $H_2O$ tetramers, $H_2O$ pentamers, $H_2O$ hexamers and larger poly-$H_2O$ molecular structures. It is unclear how to relate a pure water structure model to a biological water structure model which contains a myriad of biological molecules other than to point out that small water molecule clustering occurs even in pure water.

There is evidence from studies of the ices, from water clathrates and other solid solutions, as well as from liquid solutions, that certain motifs (designs, patterns) occur very frequently and have relatively high stability, such as the $(H_2O)_{20}$ cavity-forming structure known from studies on clathrates. The implications of recent models of water structure for an understanding of biological events, including the interactions of drugs with receptors, are profound. It is becoming clear that modeling of aqueous solutions of any molecule must consider the explicit interactions with water molecules and that water structures are simply not a continuum. As Keutsch shows water itself is not a continuum. Solute molecules which possess hydrogen-bonding groups will provoke the formation of further hydrogen-bonding chains of water molecules: if these can form rings, such rings will tend to persist longer than chains, giving the solute a secondary identity of associated water which may play a role in molecular recognition. Solutes that do not have hydrogen-bonding capability, or regions of solutes which are non-polar, may also produce partial cage-like water structures that are characteristic of the solute. (taken from Plumridge & Waigh, 2002, Water structure theory and some implications for drug design, J. Pharmacy & Pharmacology vol 54, 1155-1179).

High-resolution neutron diffraction and spectroscopic techniques have investigated pure water in confined conditions. Confined $H_2O$ molecules to 40 Å pores in Vycor glass show orientational preferences that are very different from those of bulk water (Bruni et al 1998). These $H_2O$ molecules have very slow relaxation times indicative of longer-lived cavity structures encaging other $H_2O$ molecules (Starr et al 1999). $H_2O$ dielectric relaxation times of water molecules confined by ultrafast laser spectroscopy are bimodal with a fast sub-picosecond response component as expected from bulk water and a slow response component of hundreds to thousands of picoseconds. This slow response component is 10%-40% of the total relaxation response and it is absent in pure water (Bhattacharyya & Bagchi 2000). The confined environments in these studies included molecular assemblies: reverse micelles, microemulsions (Riter et al., 1998), cyclodextrin (Vajda et al., 1995), micelles (Telgmann & Kaatze, 2000), lipids (Datta et al., 1998), proteins (Jordanides et al 1999) and DNA (Halle & Denisov 1998), and macroscopic solids which can trap water such as hydrogels (Datta et al 1997)). In all cases, the slow response component was detected and the researcher believe its origin lies in the dynamic exchange between free and bound water. A comprehensive understanding of the mechanism and implications of this phenomenon is not yet available. Overall, it is apparent that water in contact with regular hydrogen-bonding surfaces can adopt the pattern expressed at the surface and extend that pattern out into the bulk water, at least to several hundred molecular diameters (taken from Plumridge & Waigh, 2002).

Depicted in FIG. 6 is a horizontal bar graph of sorts which provides the ranges of sizes of small known objects and particulates to illustrate their sizes relative to the lengths of 0.0001 to 1000 microns. This is the same range as 0.1 nanometer to 1,000,000 nanometers. Named at the bottom of FIG. 6 are types of membrane systems (reverse osmosis, nanofiltration, ultrafiltration, microfiltration, and conventional particulate filtration) which can be used to trap or exclude particular size ranges of particulates. The three-dimensional structures of all biological macromolecules are intimately associated with water. The solid-state hydration structures of small biological molecules (carbohydrates, purines, pyrimidines, nucleosides and nucleotides) are determined mainly by packing forces, and hydrogen bonding between the functional groups of the organic molecules. Water plays a secondary role in these structures, occupying the space between the organics, and adding to the hydrogen bond energy of the lattice while in competition with the molecular packing in the absence of water. If biological molecules aggregate, or if a substrate enters the active site of an enzyme, the water molecules have to move from the contact surface of the biological molecule in a coordinated manner with the least expenditure of energy. Hydrogen bonding must play an important role in this substitution process (Jeffeey & Saenger, 1991). Unfortunately, regarding aqueous solutions in the liquid state—the structural information that can be obtained from diffraction studies on liquid species is limited because of the continual translational and rotational movement of the molecules (taken from Plumridge & Waigh, 2002).

In regard to current hypotheses for the structure of water at an interface with a charged particle or surface note that FIG. 8 depicts a prior art diagram of a model for a radial electrostatic charge distance 813 (mv) neutralization 812 of the static charge on the surface of a colloidal charged particle 802 at an interface 807 with an ionic aqueous medium 800, 801. In this aqueous radial electrostatic charge neutralization model there are three regions with the potential 809, 810, and 811. This model predicts 2 layers of aqueous ions. There is a measurable Zeta potential 811 but potentials 809 and 810 are theoretical. FIG. 8 presents this model using a negative surface charge on a colloid particle. The concept of the FIG. 8 diagram is that the negative charge of the colloid particle surface in this model will become electrically neutralized 812 over a radial distance 813 away from the particle's surface due to the charge neutralizing layers of cations 807 which accumulate and are gradually also accompanied by some anions 806, 807 in a second layer. For more details see graphs 812 and 813 in FIG. 8. These layers of particle charge neutralizing ions eventually become the bulk ionic medium 800 composition of cations 801 and anions 801. In FIG. 8 the charged particle 802 has a negative charge surface 803 which causes a surface potential 809 and there is a Stern layer 805 of positive counter-ions (cations) 804 and peripheral to the Stern layer is a concentrated mixture of cations 807 and anions 806 which has a finite thickness and then further out from the colloid charged particle is a demarcation point known as the slipping plane 808. The voltage at the slipping plane 808 is called the Zeta potential 811. The Zeta potential is an experimentally measurable characteristic of stable colloidal particle dispersions in aqueous media, which is very sensitive to the aforementioned constituents of the medium and its colloidal particle.

Another current hypotheses for the structure of water at an interface with a charged particle or surface note is described in FIG. 9 which depicts a prior art model of the effect of a charged colloid in bulk ionic medium which contrasts with the theoretical model of FIG. 9. In FIG. 9 the ionic medium at the interface of a positively charged surface 905, 903 is a model called the EZ Water Interface Model of a Charged Colloid 902 in Bulk Ionic Medium in which there is a relatively thick layer of "EZ Water" which is an aqueous medium having only anions 906, 907 and 908. This markedly contrasts with the model depicted in FIG. 9 where there is more mixing of anions and cations and the layer of this mixing appears to be thinner. Notably, within the EZ Water layer, the concentration of anions decreases radially from the charged surface 905. There is then a sudden change at 904 where the EZ Water layer and the bulk ionic medium come into contact. At this contact location 904 the EZ Water Interface Model predicts that the bulk ionic medium is concentrated in cations 909. Further and further out in the bulk ionic medium from interface 904 the concentration of cations decreases as depicted by 909, 910 and 911. The basis for the thickness of the EZ Water layer is hypothesized that it might be due to the tendency of water molecules to form complex large networks (arrays, clusters, aggregates) of water molecules that can be stabilized in unpredictable ways by various formations of variable strength H-bonds and numbers of H-bonds.

Structured water in the gaseous state has provided some evidence for long lasting stable water cluster species. Very generally speaking a cluster is a chemical description of aggregates of atoms or molecules that can be weakly bound together to create a larger structure than its individual atoms or molecules. In the mass spectra of polymeric compounds or complexes the appearance of prominent peaks in an otherwise continuous distribution of signals is called a magic number cluster, and may indicate the existence of species with enhanced stability. In water systems, it is well known that the cluster corresponding to $(H_2O)_{21}H+$ always exhibits a pronounced magic number under different experimental conditions (e.g. expansion of ionized vapor (Beuhler & Friedman 1982), ion bombardment of ice surfaces (Haberland 1984); electron impact ionization (Echt et al 1989) and vacuum photoionization of neutral clusters (Shinohara et al 1985)). Shinohara et al (1985) employed a neutral supersonic nozzle linked to a molecular-beam mass spectrometer supplied with premixed water±ammonia gas, to investigate the formation of mixed binary water±ammonium clusters. Evidence was found for exceptional structural stability of protonated clusters corresponding to $(H_2O)_{20}(NH_3)mH+$ $(m^{-1 \pm 6})_{and}$ $(H_2O)_{27}NH^{+4}$. A parallel Monte Carlo simulation yielded larger binding energies for these structures compared with their close neighbors, in agreement with the mass spectrometry results, and a deformed pentagonal dodecahedron enclosing an $NH^{+4}$ ion was proposed, with the stability due to strong coulombic interactions (ionic hydrogen bonding) between the $NH^{+4}$ and the 20 waters, as well as the inherent stability of pentagonal rings and the pentagonal dodecahedron (taken from Plumridge & Waigh, 2002).

Hydration of nucleic acids is important for the conformation of DNA. This has been demonstrated by the alteration of water activity by the addition of salts. If the DNA is fully hydrated, there are appears to be about twenty water molecules of hydration per nucleotide. If the hydration is reduced, the minimum number of waters per nucleotide approaches 3 to 6. The hydration of DNA has been described as existing with two hydration shells (Cohen & Eisenberg 1968), based on DNA sedimentation equilibrium studies. The first hydration shell is viewed as impermeable to ions and does not freeze into an ice-like state. Of the twenty waters per DNA nucleotide, it appears that 11 to 12 waters would be are directly bound in the first hydration shell to the DNA. In hydrated DNA crystal structure analyses, the first hydration shell waters are hydrogen bonded to DNA oxygen and nitrogen atoms. The second hydration shell is permeable to cations, freezes to ice I structure, and is subtly different from bulk water far away from the DNA. In considering the hydration of A-DNA, B-DNA, and Z-DNA, there are characteristic hydration patterns which are DNA sequence-dependent and DNA sequence-independent motifs (taken from Plumridge & Waigh, 2002).

Plumridge and Waigh propose there are at least four ways in which water can alter the structure of a biological macromolecule. (1) An $H_2O$ molecule can bridge two hydrogen-bonding substituents. (2) By hydrophobic bonding, two or more non-polar regions can come together and release the water molecule(s) structured about the two or more non-polar regions. (3) A polar residue that is geometrically incompatible with structured water may be transmitted by water molecules to neighboring groups and lead to a disruption of hydrophobic bonding. (4) The connecting of two domains of structured water which are geometrically compatible could occur over a relatively long distance. They propose that water domains of structured water between non-polar groups could be promoted by phosphorylation of hydrocarbons. This occurs in living cells by protein kinases and such phosphorylation is known to have a profound effects on the protein conformation which greatly modify, increase or decrease key protein functions.

Water has high adhesion properties because of its polar nature. On glass, water may form a thin film when molecular adhesive forces between glass molecules and water molecules are stronger than the cohesive forces between the water molecules. In biological cells and organelles, water is in contact with various cellular membranes and protein surfaces that are hydrophilic (water attracting).

Overall there is in any given time period in liquid water a clustering of a large portion of the $H_2O$ molecules by many H-bonds of varying strengths and steady state lifetimes. Water molecules stay close to each other (cohesion), due to the collective action of hydrogen bonds between water molecules. However, when an additional non-water substance is present or water is confined, then the hydrogen bonding should no longer be randomized and merely tetrahedral. There is ample biological evidence of this critical and essential role of water structures in biological functioning. The strength of hydrogen bonding between water molecules is hypothesized to explain why liquid water has a high surface tension of 72 mN/m at 25° C. Another piece of evidence for the strong cohesive forces between water molecules and the strong adhesive forces between water molecules and various hydrophilic surfaces is the observation that liquid water can be transported in the trunk of a tree to a height of more than 300 feet above ground. The solvent ability of liquid water is related to its high dielectric constant (88-55 at 0-100° C.). Thus the higher the dielectric constant of the substance the higher an electric field can exist between two coulombic point charges in the substance before there is an electric discharge current flow between the two coulombic point charges. Substances that mix well and dissolve in water are described as hydrophilic, whereas substances that do not mix well with water are described as hydrophobic. The ability of a substance to dissolve in water is depends on whether or not the substance can match or better the strong cohesive forces between water molecules. If a substance has properties that do not allow it to overcome the cohesive forces between the water molecules, then the substance appears to be insoluble. Put another way, it is not that water and insoluble (hydrophobic) substances "repel" each other; it is the cohesiveness of water molecules.

The hydration of insoluble (hydrophobic) substances are actually energetically favorable but not entropically favorable. Entropy is a thermodynamic concept in which it is tendency of the universe to go towards a state of greater disorder. Many non-polar substances such as fats and oils are often poorly soluble (insoluble or immiscible) in water.

In the case when an ionic or a polar compound is placed in liquid water, the compound is surrounded by water molecules and is thus hydrated because the adhesive forces of the water molecules to the hydrophilic substance are greater than the cohesive forces between the liquid water molecules. Many water molecules may surround one molecule of solute. Many ionic and polar substances such as acids, alcohols, and salts are highly soluble or miscible (soluble in each other in any proportion) in water. Water solubility of a substance may depend as well on the presence of other species dissolved in the solvent, for example, complex-forming anions (ligands) in liquids may facilitate the solubility of poorly soluble molecules.

According to the prior art, a water cluster of $H_2O$ molecules is defined to be a discrete hydrogen bonded assembly of $H_2O$ molecules of water. Water clusters have been found experimentally or predicted in silico in various forms of water; in ice, in crystal lattices and in bulk liquid water. The realization that water manifests itself as clusters rather than an isotropic collection may help explain many anomalous water characteristics such as its highly unusual density temperature dependence. Water clusters are also implicated in the stabilization of certain supramolecular structures. So little is understood about water clusters in bulk water that it is considered one of the unsolved problems in chemistry that hydrogen bonds in water break and reform at similar rates (Water Clusters, Wikivisually).

In-silico water models have been discovered which are cyclic water clusters $(H_2O)_n$ are found with n=3 to 60. Structures of water molecules with the highest resolution have been demonstrated in the studies of Saykally of Univ. Cal. At Berkeley. With increasing cluster size the oxygen to oxygen distance is found to decrease which is attributed to so-called cooperative many-body interactions: due to a change in charge distribution the H-acceptor molecule becomes a better H-donor molecule with each expansion of the water assembly. Many isomeric forms seem to exist for the hexamer: from ring, book, bag, cage, to prism shape with nearly identical energy. Two cage-like isomers exist for heptamers, and octamers are found either cyclic or in the shape of a cube. Even larger clusters are predicted: the fullerene-like cluster $(H_2O)_{28}$ is called the water buckyball and even for a 280 water molecule monster icosahedral network (with each water molecule coordinate to 4 others) there is found a local energy minimum. The 280 molecule icosahedral structure, which is 3 nm in diameter, consists of icosahedral shells with 280, 100 and 320 molecules (the 100 molecule structure is shown the figure above). There is increased stability with the addition of each shell. There are theoretical models of water clusters of more than 700 water molecules by Chaplin and Zenin.

In the prior art, it is assumed that the hydrogen bonds (H-bonds) between water molecules all have an average lifetime of 10 picoseconds, but this is unlikely. The great variability of the energy in H-bonds means that the strength of H-bonds must be highly variable and this means that the average half life time of an H-bond is going to be highly variable (some H-bonds with a half-life as brief as 10 picoseconds and some H-bonds (as in DNA chains) that has a half-life which for all purposes lasts the lifetime of the molecule. The life time of a molecule may be many years and be more affected by sudden changes in the chemical environment of the H-bond rather than the kinetic rate constants of its inherent H-bond forming and retension (adhesion and cohesion) forces. Important to note is that quantum chemical calculations of the relevant inter-residue potential constants (compliance constants) predict there should be significant differences between individual hydrogen bonds of the same type in a molecule which is a member of a population of molecules. These significant differences may result in separate or various degrees of aggregation or clustering of molecules having intermolecular H-bonds. For example, the central inter-residue N—H . . . N hydrogen bond between guanine and cytosine is much stronger in comparison to the N—H . . . N bond between the adenine-thymine pair. Accordingly within arrays of hydrogen bonds in poly water arrangements, there is no need to assume the hydrogen bonds have an equal hydrogen bond strength (Hydrogen Bond, Wikipedia, 2018).

In conclusion, there are complex overt relationships and some subtle relationships between chemical molecular, atomic and electronic and physical forces in $H_2O$ molecules, between $H_2O$ molecules, and between water cluster populations of $H_2O$ molecules. The assessment of these forces and their relative roles in water remains controversial (Plumridge & Waigh, 2002; Eaves et al., 2005; Smith et al., 2005; Chaplin, 2007; Del Guidice, 2015). The two water structure models: the uniform continuum model for liquid water versus the mixture models for liquid water continue to guide questions but more so now scientists from various disciplines (chemistry, physics, biology) have resorted to using mathematical model computer simulations and various kinds of spectroscopy experiments to perform studies of selected $H_2O$ chemical and physical phenomena.

Now add the complexity that water compositions prepared for human use and consumption often contain minerals and other non-$H_2O$ substances. $H_2O$ molecules and non-$H_2O$ substances interact in very complex ways and with a time dependence as mentioned earlier. Also, it has been mentioned that it is well known that water cluster populations of $H_2O$ molecules will change in the presence of biological molecules as mentioned. Thus, a water composition prepared for human consumption can have known ingredients, be produced by a novel process, and the water composition can have new and unpredictable properties. Improving bioavailability is an important goal for water compositions prepared for human, animal and plant consumption (Dehydration-Wikipedia, 2018; Shirreefs & Sawka, 2011; Gravelle et al., 2013). More suitable processes for making improved bioavailability water compositions are needed.

SUMMARY OF THE INVENTION

The field of the invention relates aqueous compositions with improved bioavailability, the compositions comprising an aqueous medium with reduced-size water cluster populations of $H_2O$ molecules and a non-aqueous substance. The field of the invention also relates to methods for making improved bioavailability aqueous compositions comprising processes for making an aqueous medium with reduced-size water cluster populations of $H_2O$ molecules and a non-aqueous substance. The field of the invention also relates to methods for using the improved bioavailability composition comprising aqueous medium with the reduced-size water cluster populations of $H_2O$ molecules and a non-aqueous substance. See FIG. 10 which depicts two hypothetical water clusters with intermolecular hydrogen bonded $H_2O$ molecules surrounding a non-aqueous substance. It is an object of the present invention to reduce a water cluster, for example from the one depicted in the left hand side of FIG. 10 to a reduced size water cluster for example as depicted in the right side of FIG. 10. In FIG. 11 is a flow chart which illustrates a general means with 9 process steps for accomplishing this object.

In some embodiments, the present invention is a process for reducing water cluster sizes in an aqueous composition containing a non-$H_2O$ substance in order to improve bioavailability of the aqueous composition, the process comprising the steps of: choosing an amount of the non-$H_2O$ substance to add to a volume of ultrapure water; adding the amount of the non-$H_2O$ substance to the volume of ultrapure water in a mixing tank to form a blended aqueous composition containing the non-$H_2O$ substance in the ultrapure water; pumping the blended aqueous composition at a selected flow rate from the mixing tank to a nozzle with one jet opening or a plurality of jet openings inside a hollow cylinder; using the one jet opening or the plurality of jet openings in the nozzle to jet the blended aqueous composition at a higher flow rate into the hollow cylinder; using the higher flow rate of the blended aqueous composition from the one jet opening or the plurality of jet openings inside the hollow cylinder to reduce sizes of the water clusters in the blended aqueous composition of the non-$H_2O$ substance in the ultrapure water; removing the aqueous composition with the reduced size water clusters containing the non-$H_2O$ substance at the selected flow rate from inside the hollow cylinder; and using the reduced size water clusters containing the non-$H_2O$ substance in the aqueous medium to improve the bioavailability of the aqueous composition.

In some embodiments, the present invention is a process wherein more specifically the reduced size water clusters containing the non-$H_2O$ substance in the aqueous medium may have a median water cluster size selected from the group consisting of between about 2 to 10 nanometers, about 10 to 50 nanometers, about 50 to 100 nanometers, about 100 to 200 nanometers, about 200 to 300 nanometers, about 300 to 400 nanometers, and a combination thereof.

In some embodiments, the present invention is a process, wherein more specifically the non-$H_2O$ substance comprises a ionizable salt, and wherein the amount of the ionizable salt added per gallon of the ultrapure water may be selected from the group consisting of between about 10 micrograms to 50 micrograms, about 50 micrograms to 100 micrograms, about 100 micrograms to 200 micrograms, about 200 micrograms to 400 micrograms, about 400 micrograms to 800 micrograms, about 800 micrograms to 1.6 milligrams, about 1.6 milligrams to 3.2 milligrams, about 3.2 milligrams to 6.4 milligrams, about 6.4 milligrams to 30 milligrams, and a combination thereof.

In some embodiments, the present invention is a process, wherein more specifically the ionizable salt may be comprised of ions selected from the group consisting of Aluminum ion, Ammonium ion, Antimony ion, Arsenic ion, Barium ion, Beryllium ion, Bismuth ion, Boron ion, Bromide ion, Cadmium ion, Calcium ion, Cerium ion, Cesium cation, Chloride ion, Chromium ion, Cobalt ion, Copper ion, Dysprosium ion, Erbium ion, Europium ion, Fluoride ion, Gadolinium ion, Gallium ion, Germanium ion, Gold ion, Hafnium ion, Holmium ion, Indium ion, Iodine ion, Iridium ion, Iron ion, Lanthanum ion, Lead ion, Lithium ion, Lutetium ion, Magnesium ion, Manganese ion, Mercury ion, Molybdenum ion, Neodymium ion, Nickel ion, Niobium ion, Osmium ion, Palladium ion, Phosphorus ion, Platinum ion, Potassium ion, Praseodymium ion, Rhenium ion, Rhodium ion, Rubidium ion, Ruthenium ion, Samarium ion, Scandium ion, Selenium ion, Silicon ion, Silver ion, Sodium ion, Strontium ion, Sulfate ion, Tantalum ion, Tellurium ion, Terbium ion, Thallium ion, Thorium ion, Thulium ion, Tin ion, Titanium ion, Tungsten ion, Vanadium ion, Ytterbium ion, Yttrium ion, Zinc ion, Zirconium ion, and a combination of thereof.

In some embodiments, the present invention is a process, wherein more specifically the selected flow rate from the mixing tank to the nozzle may result in a flow volume per minute which is a multiple of the hollow cylinder volume, the multiple selected from the group consisting of about 1 to 2, about 2 to 3, about 3 to 4, about 4 to 5, about 5 to 6, about 6 to 7, about 7 to 8, about 8 to 9, about 9 to 10, about 10 to 11, about 11 to 12, about 12 to 13, about 13 to 14, about 14 to 15, about 15 to 16, about 16 to 17, about 17 to 18, about 18 to 19, about 19 to 20, about 20 to 21, about 21 to 22, about 22 to 23, about 23 to 24, about 24 to 25, about 25 to 26, about 26 to 27, about 27 to 28, about 28 to 29, about 29 to 30.

In some embodiments, the present invention is a process, wherein more specifically the hollow cylinder has an inner width in inches which may be selected from the group consisting of between about 1 to 2 inches, about 2 to 3 inches, about 3 to 4 inches, about 4 to 5 inches, about 5 to 6 inches, about 6 to 7 inches, about 7 to 8 inches, about 8 to 9 inches, about 9 to 10 inches, about 10 to 11 inches, about 11 to 12 inches, about 12 to 13 inches, about 13 to 14 inches, about 14 to 15 inches, about 15 to 16 inches, about 16 to 17 inches, about 17 to 18 inches, about 18 to 19 inches, about 19 to 20 inches, and a combination thereof.

In some embodiments, the present invention is a process, wherein more specifically the hollow cylinder has an inner length in inches may be selected from the group consisting of between about 2 to 4 inches, about 4 to 6 inches, about 6 to 8 inches, about 8 to 10 inches, about 10 to 12 inches, about 12 to 14 inches, about 14 to 16 inches, about 16 to 18 inches, about 18 to 20 inches, about 20 to 22 inches, about 22 to 24 inches, about 24 to 26 inches, about 26 to 28 inches, about 28 to 30 inches, about 32 to 34 inches, about 34 to 36 inches, about 36 to 38 inches, about 38 to 40 inches, about 40 to 42 inches, about 42 to 44 inches, about 44 to 46 inches, about 46 to 48 inches, about 48 to 50, about 50 to 52, about 52 to 54, about 54 to 56, about 56 to 58, about 58 to 60, about 60 to 62, about 62 to 64, about 64 to 66, about 66 to 68, about 68 to 70, about 70 to 72, about 72 to 74, about 74 to 76, about 76 to 78, about 78 to 80 and a combination thereof.

In some embodiments, the present invention is a process, wherein more specifically the ratio of the nozzle outer diameter in inches to the hollow cylinder inner diameter in inches is a ratio which may be selected from the group consisting of about a ratio of 1:1.15 to about 1:1.25, a ratio of 1:1.25 to about 1:1.33, a ratio of about 1:1.33 to about 1:1.50, a ratio of about 1:1.50 to about 1:1.75, a ratio of about 1:1.75 to about 1:2.0, a ratio of about 1:2.0 to about 1:2.35, a ratio of about 1:2.35 to about 1:2.70, a ratio of about 1:2.70 to about 1:3.0, a ratio of about 1:3.0 to about 1:3.40, a ratio of about 1:3.40 to about 1:3.70, a ratio of about 1:3.70 to about 1:4.0, a ratio of about 1:4.0 to about 1:4.30, a ratio of about 1:4.30 to about 1:4.60, a ratio of about 1:4.60 to about 1:4.80, a ratio of about 1:4.80 to about 1:5.10, a ratio of about 1:5.10 to about 1:5.50, a ratio of about 1:5.50 to about 1:5.90, a ratio of about 1.5.90 to about 1:6.50, a ratio of ratio of about 1:6.50 to about 1:7.50, and about a ratio of 1:7.50 to about 1:12.0, and a combination thereof.

In some embodiments, the present invention is a process, wherein more specifically the nozzle may have the one jet opening or the plurality of the jet openings selected from the group consisting of 1, 2, 3, 4, 5, 6, 7, 8, 9, 10, 11, 12, 13, 14, 15, 16, 17, 18, 19, and 20. Preferred are four (4) jet openings on a nozzle of the invention.

In some embodiments, the present invention is a process, wherein more specifically the ratio of sum total area of jet openings on nozzle outer side to area of nozzle inner diameter may be selected from the group consisting of the ratio of about 0.01 to 0.05, a ratio of about 0.05 to 0.10, a ratio of about 0.10 to 0.15, a ratio of about 0.15 to 0.20, a ratio of about 0.20 to 0.25, a ratio of about 0.25 to 0.30, a ratio of about 0.30 to 0.35, a ratio of about 0.35 to 0.40, a ratio of about 0.40 to 0.45, a ratio of about 0.45 to 0.50, a ratio of about 0.50 to 0.55, a ratio of about 0.55 to 0.60, a ratio of about 0.60 to 0.65, a ratio of about 0.65 to 0.70, a ratio of about 0.70 to 0.75, a ratio of about 0.75 to 0.80, a ratio of about 0.80 to 0.85, a ratio of about 0.85 to 0.90, a ratio of about 0.90-1.0, a ratio of about 1.0 to 1.2, a ratio of about 1.2 to 1.5, a ratio of about 1.5 to 1.7, and a combination thereof.

In some embodiments, the present invention is a process, wherein more specifically the nozzle may have one curved bore hole jet opening or a plurality of the curved bore hole jet openings providing an average redirection of the jet opening angle in degrees which may be selected from the group consisting of 0, 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, and 90 degrees. In some embodiments, the present invention is a process, wherein more specifically the nozzle has the curved bore hole jet opening providing the redirection of the jet opening angle as a clockwise redirection of the jet opening angle or as a counter-clockwise redirection of the jet opening angle.

In some embodiments, the present invention is a process, wherein more specifically the process for making an aqueous composition comprising an aqueous medium with reduced size water clusters containing a non-H$_2$O substance is a process method which is not selected from the group consisting of a magnetic mixing process, a moving part mixing process, a moving impellor mixing process, a moving propeller mixing process, a moving turbine part mixing process, a moving solid baffle mixing process, a solid moving part mixing process, a moving solid rotor mixing process, a moving turbine blade mixing process, a motorized moving part mixing process, an electric motor mixing process, an electric current using process, an electric voltage using process, an electric field using process, a static electricity using process, a lightning using process, an electric spark using process, an electric shock using process, a ground isolated electric signal change using process, a ground isolated electrical pulse using process, an electric arc using process, a cathode electrode using process, an anode electrode using process, an electrolysis of water process, an electrophoresis using process, a plasma matter state using process, a permanent magnetic using process, an electromagnet using process, a magnetic field gradient using process, a linear magnetic field using process, a magnetic north field using process, a magnetic solenoid using process, a tesla coil using process, a superconducting magnet using process, a ferromagnetic field using process, a static water flow using process, a gas addition dependent process, a water steam energy using process, a water cleaning treatment plant process, a water evaporation process, a biological energy using process, an enzyme process, an Aquaporin water channel water transport process, an epithelial cell water transport process, a water insoluble liquid flow process, an extrusion of an aqueous medium through a porous wall process, a micron filtration process, an ultrafiltration process, a colloid filter process, a process using boiled water, a process in once distilled water, a non-ultrapurified water using process, a cooling source using process, a crushing materials using process, an abrasive slurry using process, and any combination thereof.

In some embodiments, the present invention is a process for reducing water cluster sizes in an aqueous composition containing a non-H$_2$O substance in order to improve bioavailability of the aqueous composition, the process comprising the steps of: choosing an amount of non-H$_2$O substance to be added to a large volume of ultrapure water; blending all of the non-H$_2$O substance in a small volume of the ultrapure water to make a small volume concentrate of the non-H$_2$O substance in the ultrapure water; wherein the small volume concentrate of the non-H$_2$O substance blended with the ultrapure water is a percent of the large volume of the ultrapure water that has been chosen, the percent may be selected from the group consisting of a 0.01 to 0.05 percent, a 0.05 to 0.1 percentage, a 0.1 to 0.2 percentage, a 0.2 to 0.3 percent, a 0.3 to 0.4 percent, a 0.4 to 0.5 percent, a 0.5 to 0.6 percent, a 0.6 to 0.7 percent, a 0.7 to 0.8 percent, a 0.8 to 0.9 percent, a 0.9 to 1.0 percent, a 1.0 to 2.0 percent, a 2.0 to 3.0 percent, a 3.0 to 4.0 percent, a 4.0 to 5.0 percent, a 5.0 to 10.0 percent, a 10.0 to 20.0 percent, and a combination thereof; filtering optionally, the small volume concentrate of the non-H$_2$O substance in the ultrapure water using a clean filter to remove micron-sized particulates from the small volume concentrate, wherein the minimum particle sizes removed by the clean filter may be selected from the group consisting of about 1 to 2 microns, 2.5 microns, 3 microns, 4 to 7 microns, 6 microns, 8-10 microns, 11 microns, and 12-25 microns, and a combination thereof; recirculating the large volume of the ultrapure water in a mixing tank and slowly adding the small volume concentrate of the non-H$_2$O substance in the ultrapure water to the mixing tank to form a blended aqueous composition containing the non-H$_2$O substance in an aqueous medium; wherein the large volume amount of the ultrapure water may be selected from the group consisting of about 10 to 20 gallons, about 20 to 50 gallons, about 50 to 100 gallons, about 100-300 gallons, about 300 to 600 gallons, about 600 gallons to about 1000 gallons, about 1000 gallons to about 2500 gallons, and a combination thereof, and wherein the adding of the small volume concentrate volume of the non-H$_2$O substance in the ultrapure water to the mixing tank to form a blended aqueous composition containing the non-H$_2$O substance in the aqueous medium may be accomplished over a time period selected from the group consisting of about 1 to 5 minutes, about 5 to 10 minutes, about 10 to 15 minutes, about 15 to 20 minutes, about 20 to 25 minutes, about 25 to 30 minutes, about 30 to 35 minutes, about 35 to 40 minutes, and a combination thereof; pumping the blended aqueous composition at a selected flow rate from the mixing tank to a nozzle with a jet opening inside a hollow cylinder; using the jet opening in the nozzle to jet the blended aqueous composition at a higher flow rate into the hollow cylinder; using the higher flow rate of the blended aqueous composition from the jet opening inside the hollow cylinder to reduce sizes of the water clusters in the blended aqueous composition of the non-$H_2O$ substance in the ultrapure water; removing the aqueous composition with the reduced size water clusters containing the non-$H_2O$ substance at the selected flow rate from inside the hollow cylinder; and using the reduced size water clusters containing the non-$H_2O$ substance in the aqueous medium to improve the bioavailability of the aqueous composition.

In some embodiments, the present invention is a process, wherein more specifically the ultrapure water is prepared by a process comprising the steps of: filtering a volume of water from a supply of water with a carbon filter to produce an amount of water with a low chlorine content; removing ions by a reverse osmosis process from the carbon filtered water with the low chlorine content so as to produce a supply of a deionized water; electro-deionizing the supply of the deionized water from the reverse osmosis process to make an ultrapure water supply; testing the resistivity of the ultrapure water to determine if the resistivity of the ultrapure water is between about 17-18.2 meg-ohm cm; repeating a process step for preparing the ultrapure water and retesting the resistivity of the ultrapure water until the ultrapure water has a measured resistivity of between about 17 meg-ohm cm to 18.2 meg-ohm cm; irradiating the supply of the ultrapure water having a measured resistivity of between about 17 meg-ohm cm to 18.2 meg-ohm cm with ultraviolet light to make a sterilized ultrapure water supply; and storing the sterilized ultrapure water in a stainless steel container until sterilized ultrapure water is needed to be added in the process to make an aqueous composition comprising an aqueous medium with reduced size water clusters containing a non-$H_2O$ substance to improve bioavailability of the aqueous composition.

In some embodiments, the present invention is a process, wherein more specifically the non-$H_2O$ substance comprises a ionizable salt, wherein the amount of the ionizable salt added per gallon of the ultrapure water may be selected from the group consisting of between about 20 micrograms to 100 micrograms, about 100 micrograms to 500 micrograms, about 500 micrograms to 2.5 milligrams, about 2.5 milligrams to 5 milligrams, about 5 milligrams to 10 milligrams, wherein the ionizable salt is comprised of ions selected from the group consisting of Boron ion, Bromide ion, Calcium ion, Cerium ion, Cesium cation, Chloride ion, Chromium ion, Cobalt ion, Copper ion, Fluoride ion, Gold ion, Indium ion, Iodine ion, Iridium ion, Iron ion, Lanthanum ion, Lithium ion, Lutetium ion, Magnesium ion, Manganese ion, Molybdenum ion, Neodymium ion, Niobium ion, Osmium ion, Palladium ion, Phosphorus ion, Platinum ion, Potassium ion, Rhenium ion, Rhodium ion, Rubidium ion, Ruthenium ion, Scandium ion, Selenium ion, Silicon ion, Silver ion, Sodium ion, Strontium ion, Sulfate ion, Tantalum ion, Tin ion, Titanium ion, Tungsten ion, Vanadium ion, Zinc ion, Zirconium ion, and a combination of thereof.

In some embodiments, the present invention is a process, wherein more specifically the hollow cylinder has an inner width in inches which may be selected from the group consisting of between about 3 to 4 inches, about 4 to 5 inches, about 5 to 6 inches, about 6 to 7 inches, about 7 to 8 inches, and a combination thereof, and wherein the hollow cylinder has an inner length in inches selected from the group consisting of between about 8 to 10 inches, about 10 to 12 inches, about 12 to 14 inches, about 14 to 16 inches, about 16 to 18 inches, about 18 to 20 inches, about 20 to 22 inches, about 22 to 24 inches, about 24 to 26 inches, and a combination thereof.

In some embodiments, the present invention is a process, wherein more specifically the selected flow rate from the mixing tank to the nozzle results in a flow volume per minute which is a multiple of the hollow cylinder volume, the multiple selected from the group consisting of about 12 to 13, about 13 to 14, about 14 to 15, about 15 to 16, about 16 to 17, about 17 to 18, about 18 to 19, and a combination thereof. In some embodiments, the present invention is a process, wherein more specifically the reduced size water clusters containing the non-$H_2O$ substance in the aqueous medium have a median water cluster size from about 3 nanometers to about 300 nanometers.

BRIEF DESCRIPTION OF THE DRAWINGS

The foregoing summary, as well as the following detailed description of preferred embodiments of the invention, will be better understood when read in conjunction with the appended drawings. For the purpose of illustrating the invention, there is shown in the drawings embodiments which are presently preferred. It should be understood, however, that the invention is not limited to the precise arrangements and instrumentalities shown. In the drawings:

FIG. 8 presents this model using a negative surface charge on a colloid particle. The concept of the FIG. 8 diagram is that the negative charge of the colloid particle surface in this model will become electrically neutralized 812 over a radial distance 813 (see graphs 812/813) away from the particle's surface due to the charge neutralizing layers of cations 807 which accumulate and are gradually also accompanied by some anions 806, 807 in a second layer. These layers of particle charge neutralizing ions eventually become the bulk ionic medium 800 composition of cations 801 and anions 801. In FIG. 8 the charged particle 802 has a negative charge surface 803 which causes a surface potential 809 and there is a Stern layer 805 of positive counter-ions (cations) 804 and peripheral to the Stem layer is a concentrated mixture of cations 807 and anions 806 which has a finite thickness and then further out from the colloid charged particle is a demarcation point known as the slipping plane 808. The voltage at the slipping plane 808 is called the Zeta potential 811. The Zeta potential is an experimentally measurable characteristic of stable colloidal particle dispersions in aqueous media, which is very sensitive to the aforementioned constituents of the medium and its colloidal particle.

In FIG. 9 the ionic medium at the interface of a positively charged surface 905, 903 is a model called the EZ Water Interface Model of a Charged Colloid 902 in Bulk Ionic Medium in which there is a relatively thick layer of "EZ Water" which is an aqueous medium having only anions 906, 907 and 908. This markedly contrasts with the model depicted in FIG. 9 where there is more mixing of anions and cations and the layer of this mixing appears to be thinner. Notably, within the EZ Water layer, the concentration of anions decreases radially from the charged surface 905. There is then a sudden change at 904 where the EZ Water layer and the bulk ionic medium come into contact. At this contact location 904 the EZ Water Interface Model predicts that the bulk ionic medium is concentrated in cations 909. Further and further out in the bulk ionic medium from interface 904 the concentration of cations decreases as depicted by 909, 910 and 911. The basis for the thickness of the EZ Water layer is hypothesized that it might be due to the tendency of water molecules to form complex large networks (arrays, clusters, aggregates) of water molecules that can be stabilized in unpredictable ways by various formations of variable strength H-bonds and numbers of H-bonds.

FIG. 16 data represents experimental proof of an actual reduction of the invention to practice. This embodiment of the present invention based on testing of this first test sample, reduced median water cluster size in flowing blended aqueous formulation 1213 by 44-fold (from a median value of 358 nanometers down to 8 nanometers).

FIG. 18 data represents a second example proof of a reduction to practice of the invention. This embodiment of the present invention based on testing of this second test sample, reduced median water cluster size in flowing blended aqueous formulation 1213 by 114-fold (from a median value of 286 nanometers down to 2.5 nanometers).

FIGS. 15 and 17 depicts three modes of size distributions with median sizes of 310 nm, 542 nm, and 20 nm. The standard deviation is 293 nm for the mode with a median value of 542 nm, and is 108 nm for the data with the median value of 310. See histogram at bottom of FIG. 19 for size distribution of the measured water clusters in the tested sample. FIG. 19 represents the kind of problem data that can apparently arise when the invention apparatus has not fully yet operational. One inventor is of the opinion that this invention sample absorbed atmospheric air and this would modify the water cluster sizes in ultrapurified water (UPW) BEFORE there has been any water cluster size reduction by the present invention.

DETAILED DESCRIPTION OF THE INVENTION

Figure 1:
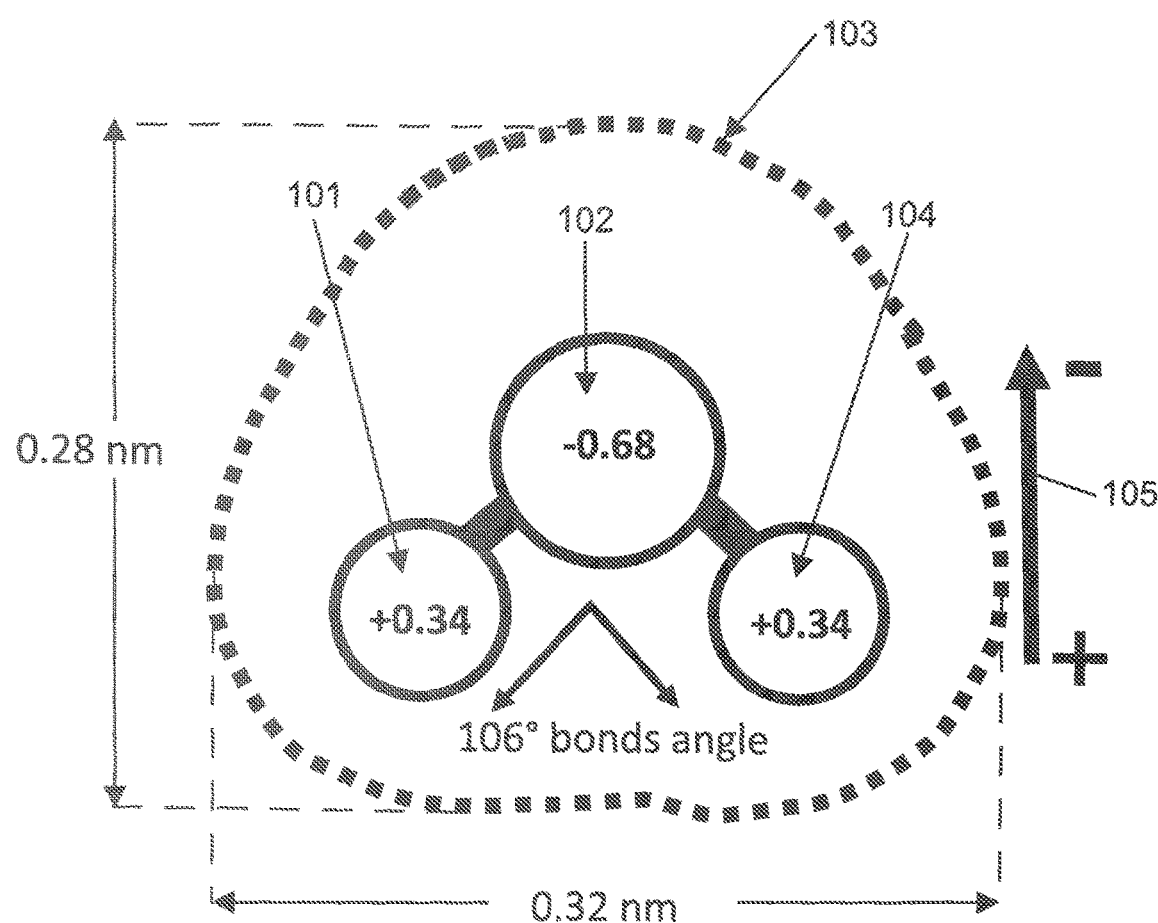
FIG. 1 depicts a prior art diagram of a gas phase water molecule in which water is portrayed as a simple molecule containing 2 hydrogen atoms and 1 oxygen atom with a bond angle of 106 degrees and as a polar molecule.
Figure 2:
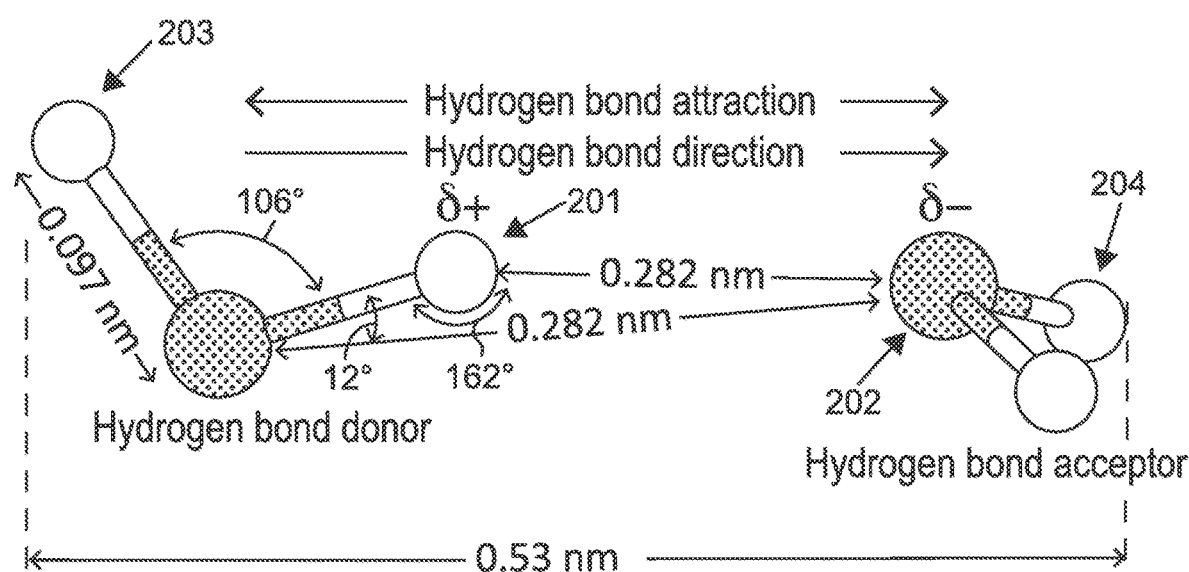
FIG. 2 depicts a prior art diagram of 2 water molecules engaged in hydrogen bonding one water molecule oxygen atom 202 and the second water molecule hydrogen atom 201 form an H-bond. Such a simple 2 molecule interaction may be uncommon in liquid water where formations of a larger number of water molecules in interactions together involving 2, 3, and 4 hydrogen bonding events with neighboring water molecules are more commonly observed.
Figure 3:
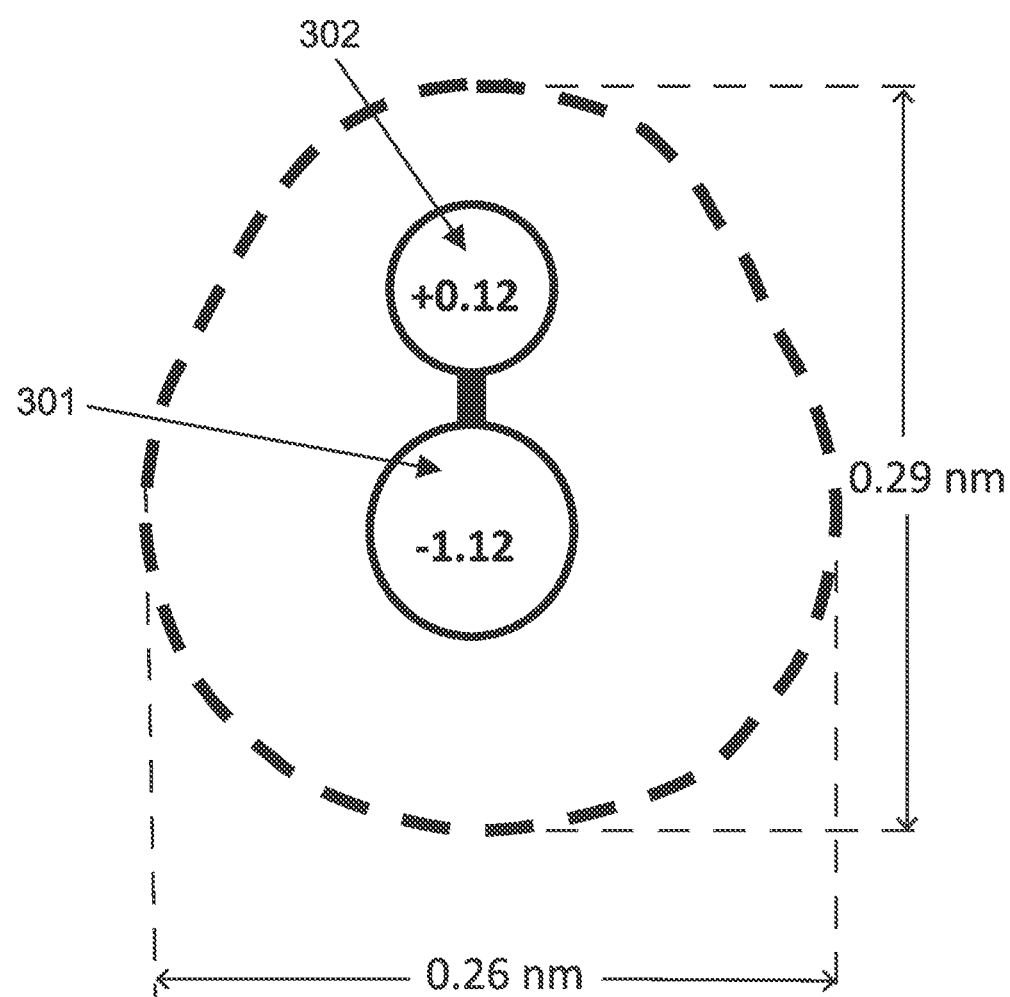
FIG. 3 depicts a prior art diagram in an overly simplified structure for the hydroxonium ion (—OH) in water which has also been called the hydroxide anion.
Figure 4:
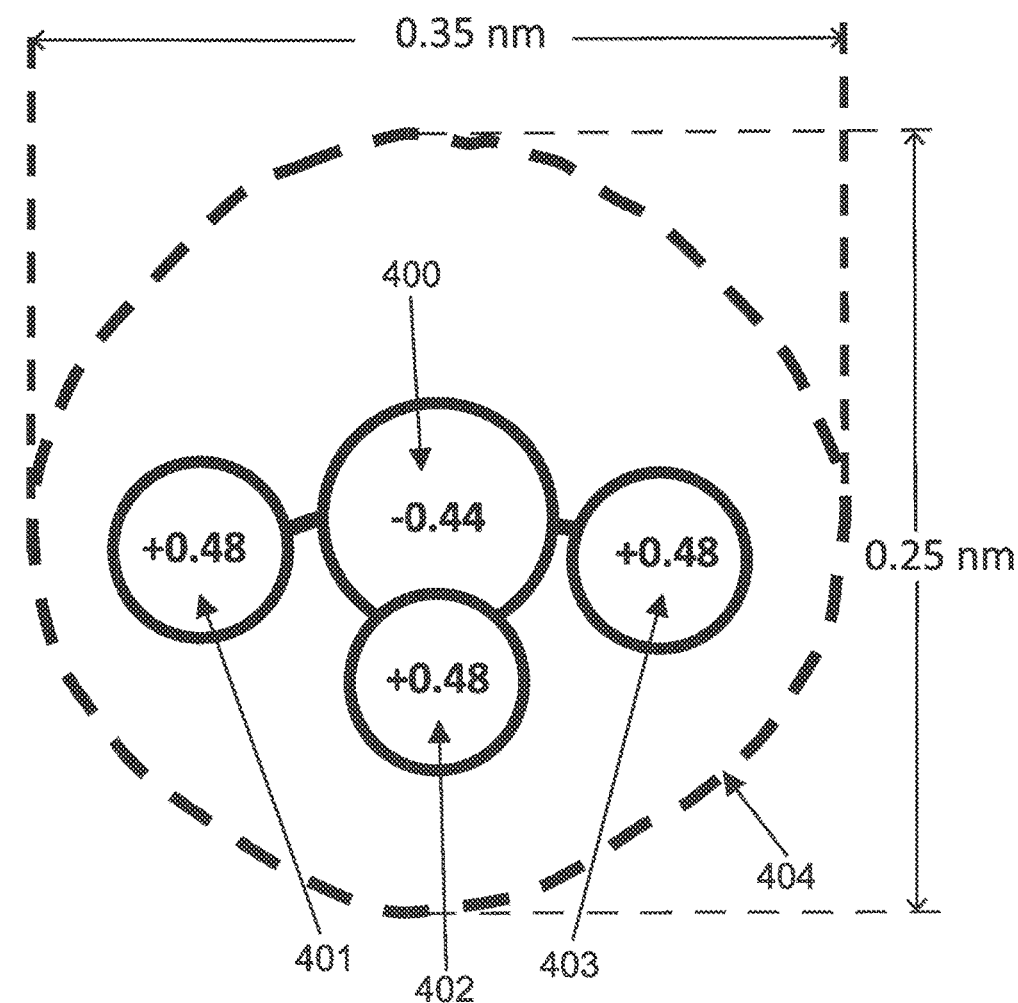
FIG. 4 depicts a prior art diagram of hydronium ion molecule in an overly simplified form as having 3 hydrogen atoms and 1 oxygen atom.
Figure 5:
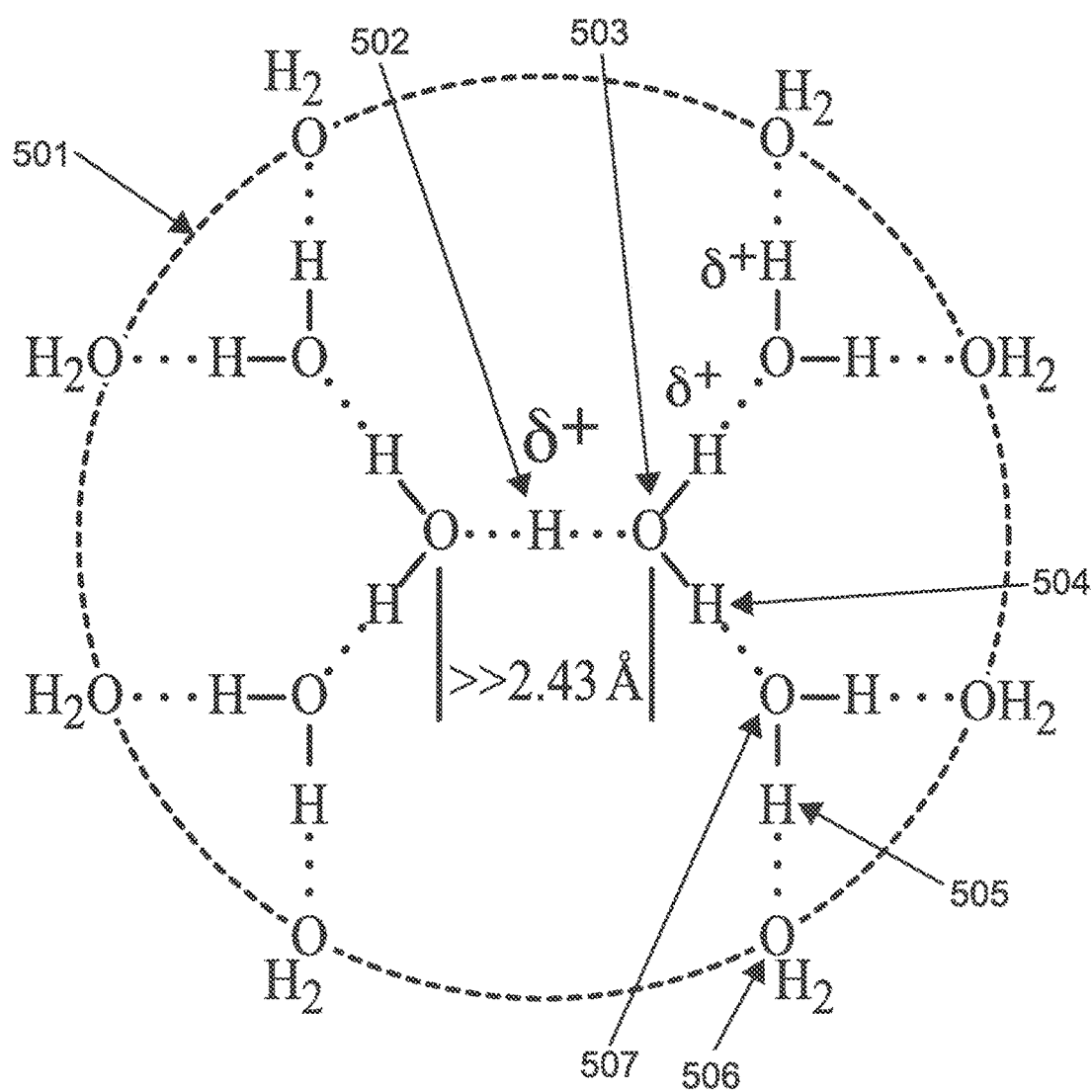
FIG. 5 depicts a prior art model of how a hydrogen ion (proton) might become situated between 2 oxygen atoms of 2 different water molecules as a means for a neutralization or a delocalization of some of the positive charge of the proton. This model was proposed by Stoyanov in 2010 and represents a 6 water molecule planar network of hydrogen bonding within the dashed circle 501. This 6 molecule water structure has been assigned the molecular formula $H_{13}O_6^+$.
Figure 6:
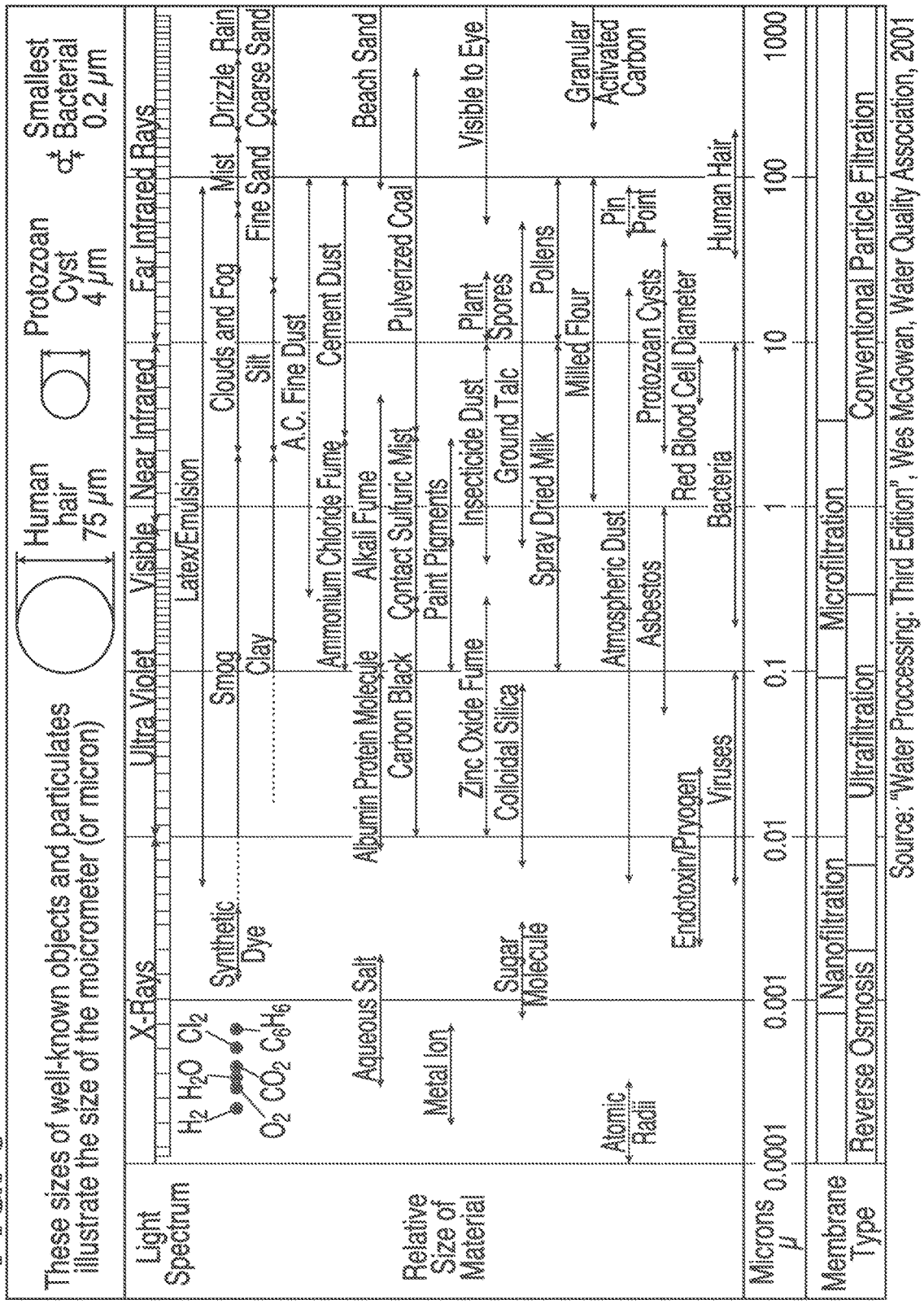
FIG. 6 depicts a prior art diagram listing the ranges of sizes of substances (microorganisms, proteins, sugars, aqueous salts, metal ions and water molecules). The diagram does not suggest hydrogen bond related water clusters, aggregates of water molecules, organized arrays of water molecules or the like whatsoever, particularly note in aqueous salt size ranges. Only large particle sizes (100 nm or larger sizes) are shown for solids in the FIG. 6 diagram.

The field of the invention relates compositions with improved bioavailability, the compositions comprising an aqueous medium with reduced-size water cluster populations of $H_2O$ molecules and a selected non-aqueous substance. The field of the invention also relates to methods for making the improved bioavailability compositions comprising the aqueous medium with the reduced-size water cluster populations of $H_2O$ molecules and a selected non-aqueous substance. The field of the invention also relates to methods for using the improved bioavailability composition comprising aqueous medium with the reduced-size water cluster populations of $H_2O$ molecules and a selected non-aqueous substance.

Invention Attributes

Embodiments of the present invention have the following attributes: (a) water molecule cluster arrangements after the process are stable in their new nano-size range; (b) water molecules can encapsulate desired particles and/or nutritional agents and serve as a more efficient cellular delivery system for particles or nutritional agents; (c) encapsulated nano-water molecules work in both a ionic and non-ionic environment; (d) encapsulated nano-water molecule arrangements have a highly stable and consistent size range that measures in 1 nm to 400 nm range.

The size range measurement of encapsulated nano-water molecule arrangements depends also on the nature and size of encapsulated particle or nutritional agent. The nano-water molecule arrangements stabilize and form a highly bound condition that is unique to the particle being encapsulated. During processes of the present invention for making water, the making of Ultra Pure Water (UPW) requires the complete removal of all impurities or previously contain traces of other particles or contaminates. Once Ultra Pure Water (UPW) status is reached, only then is non-$H_2O$ substance (particle or nutritional agent) added to the UPW. This way the UPW can encapsulate the non-$H_2O$ substance in a small size UPW water cluster.

Example Utility Embodiments of the Present Invention

For some embodiments of the present invention, being able to do nano-sizing of a non-$H_2O$ substance in ultrapure water is a highly useful utility of the present invention. For example embodiments of the present invention can be useful for improving a hydration drink for mammals including humans and animals. Drinks for meals, for water bottles, for water coolers, for beverages sold in bottles, beer, wine—all can all be made better hydrating using the present invention embodiments. Water in food preparation at home and in stores can use the invention's water embodiments. Persons needing hydration include athletes, outdoors persons, office workers, people camping and hiking, In some embodiments of the present invention, nano-sized particles in ultra purified water clusters can be useful as a means for increasing growth and body weight in mammals including humans and animals, for example for growth and health of non-human animals—farming poultry, beef, pig and other animal farming. Fish farms and seafood farms in artificial pools can use the present invention embodiments.

In yet other embodiments of the present invention, nano-sized particles in ultra purified water clusters are useful as a means for increasing root development in plants, growth and health of plant material—farming, agriculture, aqua-culture process uses.

Furthermore, in some other specific embodiments of the present invention, nano-sized particles in ultra purified water are useful as a means for increasing leaf development in plants.

It is observed that some embodiments of the present invention, nano-sized particles in ultra purified water clusters can be used as a means for increasing water uptake in plants.

Notably, in some specific embodiments of the present invention, the nano-sized particles in ultra purified water are useful as a means for increasing drought tolerance in plants.

Surprising specific embodiments of the present invention, nano-sized particles in ultra purified water can be used as a means for increasing vegetable yields in plants.

In specific embodiments of the present invention, nano-sized particles in ultra purified water are used as a means for increasing fruit production from trees.

It is contemplated that specific embodiments of the present invention, can make nano-sized particles in ultra purified water that will be useful as a means for improving sweetness of grapes on grape vines.

In specific embodiments of the present invention, nano-sized particles in ultra purified water could be used as a means for increasing the rate of tree growth.

In specific embodiments of the present invention, nano-sized particles in ultra purified water can be used for improving an isotonic saline for intravenous use in a mammal.

In specific embodiments of the present invention, nano-sized particles in ultra purified water could be useful as a means for increasing drug solubility in drug formulations, improving pharmacokinetics and bioavailability processes. The potential applications of the invention as an improved water source water in medical products, cell culture, patient care, cadaver harvest, medical research, medical testing, medical equipment, surgical procedures.

It is contemplated that specific embodiments of the present invention may use nano-sized particles in ultra purified water as a means for increasing oral drug bioavailability.

Furthermore, specific embodiments of the present invention, nano-sized particles in ultra purified water could be used as a means for increasing drug potency.

Also specific embodiments of the present invention, nano-sized particles in ultra purified water are used as a means for increasing exercise ability of in a mammal.

It is contemplated as well that specific embodiments of the present invention, nano-sized particles in ultra purified water would be used as a means for increasing exercise ability of in a mammal In some forms, nano-sized particles in ultra purified water are contemplated to be useful as a means for increasing exercise ability of a mammal.

In some specific embodiments of the present invention, nano-sized particles in ultra-purified water would be useful as a means for increasing mental alertness in a mammal.

In addition, specific embodiments of the present invention, nano-sized particles in ultrapurified water have been found useful as a means for increasing recovery from dehydration of a mammal.

In specific embodiments of the present invention, nano-sized particles in ultra purified water are useful as a means for improving the mental thinking in a mammal.

This includes the conception that specific embodiments of the present invention, nano-sized particles in ultra purified water could be used as a means for treating psychological depression in a mammal.

Furthermore, specific embodiments of the present invention, nano-sized particles in ultra purified water are contemplated to helpful for treating hypothermia in a mammal.

Furthermore, specific embodiments of the present invention, nano-sized particles in ultra purified water could be used as a means for increasing drug potency of antibiotics.

Notably, some embodiments of the present invention, nano-sized particles in ultra purified water are contemplated to be used as a means for treating heat stroke in a mammal.

In some embodiments of the present invention, nano-sized particles in ultra purified water are useful for as a means for treating shock from physical trauma in a mammal.

In some specific pharmaceutical embodiments of the present invention, nano-sized particles in ultrapurified water could be used as a means for treating inflammation in a mammal.

Furthermore, specific embodiments of the present invention, nano-sized particles in ultrapurified water could be used as a means for increasing drug potency of narcotic medications.

By the present invention embodiment's potential to increasing a drug's bioavailability in a mammal there can be a lower dosing of the mammalian patient with a drug. This results in a lower drug loading of the patient and less drug side effects, less development of metabolic/psychological tolerance and less liver metabolic stress.

Furthermore, specific embodiments of the present invention, nano-sized particles in ultra purified water could be used as a means for increasing drug potency of antibiotics. Many other embodiments of the invention are contemplated and shall be tested.

Example for a Process for Making Embodiments of the Present Invention

Figure 11:
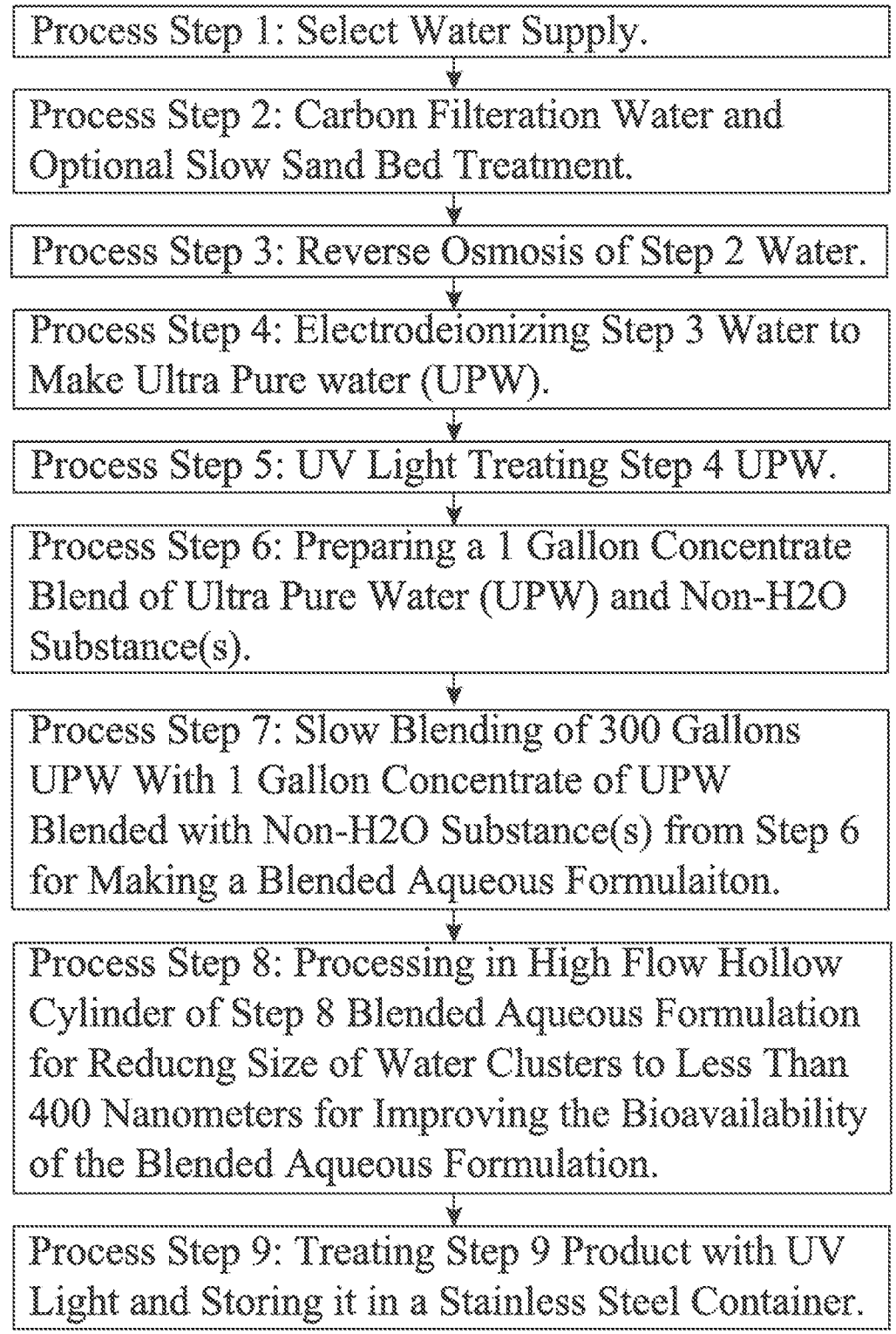
FIG. 11 depicts a flow chart for a process of the present invention with 9 process steps for making a composition based upon an invention embodiment formulation wherein the composition is an aqueous medium with reduced size water clusters comprising ultrapure water (UPW) with a non-$H_2O$ substance(s) and wherein the composition has usefulness as a surprisingly improved bioavailability product embodiment of the present invention.

Process Step 1—Selecting a Suitable Water Supply (FIG. 11)

Process Step 1 is selecting a suitable water supply to purify to make ultrapure water (UPW) in a four-step process. By the present invention, an example process for making most embodiments of the present invention, involves a first process step which is selecting a suitable water supply and preferably this is a fresh water supply. If one must begin the process by selecting a sea water or high salt containing water as a water supply then a distilling of or an evaporating of a salt-containing water is a means for making a fresh water condensate that can be used as a fresh water supply. A preferred fresh water supply is safe to drink and includes water from a municipal treated water supply, a fresh water lake, a fresh water river, or an uncontaminated ground water supply. Safe to drink means the fresh water has been tested to determine if the water supply is orally non-toxic to a mammal, meaning the safe to drink water contains nil levels or amounts of pathogenic microorganisms and toxic chemicals.

For example, a safe to drink fresh water supply preferably has immeasurable (meaning "nil") levels/amounts of the following pathogens and toxins: (a) pathogenic bacteria (for example fecal coliform), viruses (for example hepatitis viruses, hemorrhagic viruses, retroviruses such as AIDS virus), fungi, mycoplasm, protozoa, prokaryotes, protists, parasites, microorganisms causing infectious diseases, and their spores, eggs, DNA, RNA, or related reproductive constituents, prions, (b) toxic biochemical including toxic proteins, lipids, carbohydrates, toxic nucleic acids, known carcinogens, and chemotherapy drugs; (c) toxic inorganic chemicals (soluble and insoluble in water, and including toxic heavy metals) and their particles; (d) toxic organic chemicals (soluble and insoluble in water, and pesticides) and their particles; (e) non-water organic liquids (miscible and immiscible); (f) radioactive minerals, and (g) toxic gases including ammonia, arsenic pentafluoride, arsine, bis(trifluoromethyl)peroxide, boron tribromide, boron trichloride, boron trifluoride, bromine, bromine chloride, boromethane, carbon monoxide, chlorine, chlorine pentafluoride, chlorine trifluoride, chloropicrin, cyanogen, cyanogen chloride, diazomethane, diborane, dichloroacetylene, dichlorosilane, fluorine, formaldehyde, germane, hexylethyl tetraphosphate, hydrogen azide, hydrogen cyanide, hydrogen selenide, hydrogen sulfide, hydrogen telluride, nickel tetracarbonyl, nitrogen dioxide, osmium tetroxide, oxygen difluoride, perfluoroisobuytlene, phosgene, phosphine, phosphorus pentafluoride, selenium hexafluoride, silicon hexafluoride, silicon tetrachloride, stilbene, disulfur decafluoride, sulfur tetrafluoride, tellurium hexafluoride, tetraethyl pyrophosphate, tetraethyl dithiopyrophosphate, trifluoroacetyl chloride, tungsten hexafluoride, and radon. Nil levels or nil amounts means the level or amount is so low that it is currently immeasurable or undetectable by known means.

Process Step 2A—Carbon Filtering of the Suitable Water Supply (FIG. 11)

FIG. 11 provides a flow chart of an example of a 9-step process for making a product of the present invention and is not intended as a limiting example for embodiments of the invention directed to making products of the invention. Step 2 is a carbon filtering of the suitable water supply to be sure to remove any chlorine chemicals content (see FIG. 11, 1101). For example, several hundred gallons of Process Step 1 water may be used to perform Step 2 so that chlorine chemicals are removed prior to the Step 3 reverse osmosis process. This is done because chlorine chemicals can damage reverse osmosis membranes. In addition, carbon filtering is a method of filtering that uses a bed of activated carbon to usefully remove contaminants and impurities, using chemical adsorption. Each particle, or granule, of carbon provides a large surface area, or pore structure, allowing contaminants the maximum possible exposure to the active sites within the filter media. One gram of activated carbon has a surface area in excess of 3,000 meters$^2$ (32,000 sq. ft.). Activated carbon works via a process called adsorption, whereby pollutant molecules in the fluid to be treated are trapped inside the pore structure of the carbon substrate. Active charcoal carbon filters are most effective at removing chlorine, particles such as sediment, volatile organic compounds (VOCs), taste and odor from water. They are not effective at removing minerals, salts, and dissolved inorganic substances. Typical particle sizes that can be removed by carbon filters range from 0.5 to 50 micrometers (from Carbon Filtering—Wikipedia, Oct. 1, 2018). Carbon filtering of the suitable water supply with a carbon filtration process is useful for removing chlorine when the suitable water supply from a municipal drinking water supply using chlorination (Wikipedia, Carbon Filtration).

Process Step 2B—Optional Slow Sand Filter Treatment (FIG. 11)

Optionally, a Process Step 2B is added for a filtering of the suitable water supply with a slow sand filter. If the water supply is low quality water then a process of the filtering of the suitable water supply from Process Step 1 with a slow sand filter process Step 2B may be necessary prior to or following the step of filtering of the suitable water supply with the carbon filtration process. Pretreatment is important when working with reverse osmosis and nanofiltration membranes due to the nature of their spiral-wound design. The material is engineered in such a fashion as to allow only one-way flow through the system. As such, the spiral-wound design does not allow for back-pulsing with water or air agitation to scour its surface and remove solids. Since accumulated material cannot be removed from the membrane surface systems, they are highly susceptible to fouling (loss of production capacity). Therefore, pretreatment is a necessity for any reverse osmosis or nanofiltration system. Pretreatment in sea water reverse osmosis systems has four major components: (1) Screening of solids: Solids within the water must be removed and the water treated to prevent fouling of the membranes by fine particle or biological growth, and reduce the risk of damage to high-pressure pump components. (2) Cartridge filtration: Generally, string-wound polypropylene filters are used to remove particles of 1-5 μm diameter. (3) Dosing: Oxidizing biocides, such as chlorine, are added to kill bacteria, followed by bisulfite dosing to deactivate the chlorine, which can destroy a thin-film composite membrane. There are also biofouling inhibitors, which do not kill bacteria, but simply prevent them from growing slime on the membrane surface and plant walls. (4) Prefiltration pH adjustment: If the pH, hardness and the alkalinity in the feed water result in a scaling tendency when they are concentrated in the reject stream, acid is dosed to maintain carbonates in their soluble carbonic acid form. $CO3-+H3O+=HCO3-+H2O$ and $HCO3-+H3O+=H2CO3+H2O$. Carbonic acid cannot combine with calcium to form calcium carbonate scale. Calcium carbonate scaling tendency is estimated using the Langelier saturation index. Adding too much sulfuric acid to control carbonate scales may result in calcium sulfate, barium sulfate, or strontium sulfate scale formation on the reverse osmosis membranes, Prefiltration antiscalants: Scale inhibitors (also known as antiscalants) prevent formation of all scales compared to acid, which can only prevent formation of calcium carbonate and calcium phosphate scales. In addition to inhibiting carbonate and phosphate scales, antiscalants inhibit sulfate and fluoride scales and disperse colloids and metal oxides. Despite claims that antiscalants can inhibit silica formation, no concrete evidence proves that silica polymerization can be inhibited by antiscalants. Antiscalants can control acid-soluble scales at a fraction of the dosage required to control the same scale using sulfuric acid. Some small scale desalination units use 'beach wells'; they are usually drilled on the seashore in close vicinity to the ocean. These intake facilities are relatively simple to build and the seawater they collect is pretreated via slow filtration through the subsurface sand/seabed formations in the area of source water extraction. Raw seawater collected using beach wells is often of better quality in terms of solids, silt, oil and grease, natural organic contamination and aquatic microorganisms, compared to open seawater intakes. Sometimes, beach intakes may also yield source water of lower salinity.

For example, the slow sand filter can be used in water purification for treating raw water to produce a potable product. The slow sand filter may be 3-6 feet deep, and rectangular or cylindrical in cross section. The length and breadth of the tanks will be in part determined by the flow rate desired by the filters, which typically have a loading rate of 50-100 gallons per hour per square yard (or 0.2-0.4 cubic yards per square yard per hour). A slow sand filter works through the formation of a gelatinous layer (or biofilm) called the hypogeal layer or Schmutzdecke in the top few millimeters of the fine sand layer. The Schmutzdecke is formed in the first 10-20 days of operation and consists of bacteria, fungi, protozoa, rotifera and a range of aquatic insect larvae. As an epigeal biofilm ages, more algae tend to develop and larger aquatic organisms may be present including some bryozoa, snails and Annelid worms. The surface biofilm is the layer that provides the effective purification in potable water treatment, the underlying sand providing the support medium for this biological treatment layer. As water passes through the hypogeal layer, particles of foreign matter are trapped in the mucilaginous matrix and soluble organic material is adsorbed. The contaminants in the water coming into the slow sand filter are metabolized by the bacteria, fungi and protozoa. The water produced from an efficient slow sand filter can have a 90-99% bacterial cell count reduction. Slow sand filters gradually lose their performance as the biofilm thickens and thereby reduces the rate of flow through the filter. Eventually, it is necessary to refurbish the filter. Two methods are commonly used to do this. In the first, the top few millimeters of fine sand is scraped off to expose a new layer of clean sand. Water is then decanted back into the filter and re-circulated for a few hours to allow a new biofilm to develop. The filter is then filled to full volume and brought back into service. The second method, sometimes called wet harrowing, involves lowering the water level to just above the hypogeal layer, stirring the sand; thus precipitating any solids held in that layer and allowing the remaining water to wash through the sand. The filter column is then filled to full capacity and brought back into service. Wet harrowing can allow the filter to be brought back into service more quickly. Unlike other water filtration technologies that produce water on demand, slow sand filters produce water at a slow, constant flow rate and are usually used in conjunction with a storage tank for peak usage. Slow sand filters are recognized by the World Health Organization, Oxfam, and the United States Environmental Protection Agency as being superior technology for the treatment of surface water sources. According to the World Health Organization, "Under suitable circumstances, slow sand filtration may be not only the cheapest and simplest but also the most efficient method of water treatment." (Wikipedia, Slow Sand Filter).

Process Step 3—Reverse Osmosis Water Purification (FIG. 11)

Process Step 3 is performing a reverse osmosis water purification technology that uses, for example, a semipermeable membrane to remove ions, molecules and larger particles from drinking water (see FIG. 11, 1102) (Reverse Osmosis—Wikipedia). During the step 3 reverse osmosis process, an applied pressure is used to overcome osmotic pressure, a colligative property that is driven by chemical potential differences of the solvent, a thermodynamic parameter. Reverse osmosis can remove many types of dissolved and suspended species from water, including bacteria, and is used in both industrial processes and the production of potable water. The result is that the solute is retained on the pressurized side of the membrane and the pure solvent is allowed to pass to the other side. To be "selective", this membrane should not allow large molecules or ions through the pores (holes), but should allow smaller components of the solution (such as solvent molecules) to pass freely.

In the normal osmosis process, the solvent naturally moves from an area of low solute concentration (high water potential), through a membrane, to an area of high solute concentration (low water potential). The driving force for the movement of the solvent is the reduction in the free energy of the system when the difference in solvent concentration on either side of a membrane is reduced, generating osmotic pressure due to the solvent moving into the more concentrated solution. Applying an external pressure to reverse the natural flow of pure solvent, thus, is reverse osmosis. The process is similar to other membrane technology applications. However, key differences are found between reverse osmosis and filtration. The predominant removal mechanism in membrane filtration is straining, or size exclusion, so the process can theoretically achieve perfect efficiency regardless of parameters such as the solution's pressure and concentration. Reverse osmosis also involves diffusion, making the process dependent on pressure, flow rate, and other conditions. Reverse osmosis is most commonly known for its use in drinking water purification from seawater, removing the salt and other effluent materials from the water molecules. Rain water collected from storm drains is purified with reverse osmosis water processors and used for landscape irrigation and industrial cooling in Los Angeles and other cities, as a solution to the problem of water shortages. It is also used to clean effluent and brackish groundwater. The effluent in larger volumes (more than 500 m3/day) should be treated in an effluent treatment plant first, and then the clear effluent is subjected to reverse osmosis system. Treatment cost is reduced significantly and membrane life of the reverse osmosis system is increased. The process of reverse osmosis can be used for the production of deionized water. Reverse osmosis process for water purification does not require thermal energy. Flow-through reverse osmosis systems can be regulated by high-pressure pumps. The recovery of purified water depends upon various factors, including membrane sizes, membrane pore size, temperature, operating pressure, and membrane surface area. John Cadotte, of FilmTec Corporation, discovered that membranes with particularly high flux and low salt passage could be made, for example, by an interfacial polymerization of m-phenylene diamine and trimesoyl chloride. For these reverse osmosis membranes, an activated carbon filter to trap organic chemicals and chlorine, which will attack and degrade thin film composite membrane reverse osmosis membranes.

Formally, reverse osmosis is the process of forcing a solvent from a region of high solute concentration through a semipermeable membrane to a region of low solute concentration by applying a pressure in excess of the osmotic pressure. The largest and most important application of reverse osmosis is the separation of pure water from seawater and brackish waters; seawater or brackish water is pressurized against one surface of the membrane, causing transport of salt-depleted water across the membrane and emergence of potable drinking water from the low-pressure side. The membranes used for reverse osmosis have a dense layer in the polymer matrix—either the skin of an asymmetric membrane or an interfacially polymerized layer within a thin-film-composite membrane—where the separation occurs. In most cases, the membrane is designed to allow only water to pass through this dense layer while preventing the passage of solutes (such as salt ions). This process requires that a high pressure be exerted on the high concentration side of the membrane, usually 2-17 bar (30-250 psi) for fresh and brackish water, and 40-82 bar (600-1200 psi) for seawater, which has around 27 bar (390 psi) natural osmotic pressure that must be overcome. This process is best known for its use in desalination (removing the salt and other minerals from sea water to produce fresh water), but since the early 1970s, it has also been used to purify fresh water for medical, industrial, and domestic applications.

However, in some systems, an alternative method for performing Process Step 3 of the present invention is that the carbon pre-filter is omitted, and a cellulose triacetate membrane is used. CTA (cellulose triacetate) is a paper by-product membrane bonded to a synthetic layer and is made to allow contact with chlorine in the water. Up to 50% of the seawater input can be recovered as fresh water, though lower recoveries may reduce membrane fouling and energy consumption. High pressure pump—The high pressure pump supplies the pressure needed to push water through the membrane, even as the membrane rejects the passage of salt through it. Typical pressures for brackish water range from 1.6 to 2.6 MPa (225 to 376 psi). In the case of seawater, they range from 5.5 to 8 MPa (800 to 1,180 psi).

Membrane assembly: The layers of a membrane—The membrane assembly consists of a pressure vessel with a membrane that allows feed water to be pressed against it. The membrane must be strong enough to withstand whatever pressure is applied against it. Reverse osmosis membranes are made in a variety of physical configurations, with the two most common configurations being spiral-wound and hollow-fiber. Only a part of the saline feed water pumped into the membrane assembly passes through the membrane with the salt removed. The remaining "concentrate" flow passes along the saline side of the membrane to flush away the concentrated salt solution. The percentage of desalinated water produced versus the saline water feed flow is known as the "recovery ratio". This varies with the salinity of the feed water and the system design parameters: typically 20% for small seawater systems, 40%-50% for larger seawater systems, and 80%-85% for brackish water. The concentrate flow is at typically only 3 bar/50 psi less than the feed pressure, and thus still carries much of the high pressure pump input energy. The desalinated water purity is a function of the feed water salinity, membrane selection and recovery ratio. To achieve higher purity a second pass can be added which generally requires re-pumping. Purity expressed as total dissolved solids typically varies from 100 to 400 parts per million (ppm or mg/liter on a seawater feed. Reverse osmosis is an effective barrier to pathogens, but post-treatment provides secondary protection against compromised membranes and downstream problems. Disinfection by means of ultra violet (UV) lamps (sometimes called germicidal or bactericidal) may be employed to sterilize pathogens which bypassed the reverse osmosis process. Chlorination or chloramination (chlorine and ammonia) protects against pathogens which may have lodged in the distribution system downstream, such as from new construction, backwash, compromised pipes, etc. Due to its fine membrane construction, reverse osmosis not only removes harmful contaminants present in the water, but it also may remove many of the desirable minerals from the water. Since the 1970s, pre-filtration of high-fouling waters with another larger-pore membrane, with less hydraulic energy requirement, has been evaluated and sometimes used. However, this means that the water passes through two membranes and is often re-pressurized, which requires more energy to be put into the system, and thus increases the cost. Other recent developmental work has focused on integrating reverse osmosis with electro-dialysis to improve recovery of valuable deionized products, or to minimize the volume of concentrate requiring discharge or disposal. The latest developments in reverse osmosis membrane technology include nanoscale and graphene membranes.

Process Step 4—EDI Treatment (Electro-Deionization Treatment) (FIG. 11)

Process Step 4 an electro-deionization (EDI) water treatment (see FIG. 11, 1103) is performed that utilizes electricity, ion exchange membranes and resin to deionize water and separate dissolved ions (impurities) from water (EDI—Wikipedia). It differs from other water purification technologies in that it is done without the use of chemical treatments and is usually a polishing treatment to the reverse osmosis (RO) treatment. There are also EDI units that are often referred to as continuous electro-deionization (CEDI) since the electric current regenerates the resin mass continuously. CEDI technique can achieve very high purity, with conductivity below 0.1 µS/cm. Recently, Argonne National Laboratory developed a process called Resin-Wafer Electro-deionization (RW-EDI), which uses a unique porous resin wafer mold made from immobilized loose ion-exchange resin beads. The resin wafer material enhances mass transfer between solid (resin bead) and liquid (feed solution) phases to achieve a high purity, especially when treating impaired or brackish water. When fed with low TDS (total dissolved solids) feed (e.g., feed purified by RO (reverse osmosis), the product can reach very high purity levels (e.g., 18 meg-ohms cm). The ion exchange resins act to retain the ions, allowing these to be transported across the ion exchange membranes. The main applications of EDI (electro-deionization) technology, such as that supplied by Ionpure, E-cell and Snow-Pure, are in electronics, pharmaceuticals and power generation.

The means by which an EDI process can work is as follows. The process uses two electrodes in an electrochemical cell. Each electrode may function as either the anode or the cathode depending on the voltage applied to the cell. One option is to use a bipolar electrode that can function as the anode of one cell and the cathode of another cell. When using a bipolar electrode each cell will have an electrode and a water soluble electrolyte with ions that can undergo either an oxidation or a reduction. The electrolyte in the electrochemical cell is a source of free ions so that the cell can conduct electricity between its two electrodes.

EDI occurs as the reverse osmosis water made from Process Step 3 is then passed between an anode (positive electrode) and a cathode (negative electrode). Ion-selective membranes allow the positive ions to separate from the water toward the negative electrode and the negative ions toward the positive electrode. This clear the water of remaining mobile anions and cations so that a high purity deionized water results An alternative method to practicing Process Step 4 of the present invention is to use Resin-Water Electro-deionization—RW-EDI is a process that targets the desalination of impaired water or water with salt levels of 1,000-10,000 ppm. RW-EDI process uses a porous ion exchange resin wafer with 195 $cm^2$ (cross-section surface area). Water is run through the wafer, while an electric current is applied to setup. Between resin wafer compartments there are concentrate compartments from which brine flows. An anode is situated on one side of the concentrate compartment and the cathode is situated on the other side of the concentrate compartment. When an electric current is used to charge ions that need to be removed by the EDI, positively charged ions that are formed will flow toward the cathode and then can be rinsed away in one direction by a flowing concentrate stream. Negatively charged ions that are formed will flow toward the anode and then can be rinsed away in the same direction by another flowing concentrate stream. As a result, there is a production of purified water between the cathode and the anode electrodes which can flow in the opposite direction from the waste charged ions produced by the EDI. The resin-wafer technology usefully increases the energy efficiency of the desalination process by 5-10 fold. (EDI-Wikipedia). The term in the art of water purification is that EDI process is a "final polishing treatment". EDI is very important because it is a process which increases the resistivity of the water to nearly its theoretical maximum of 18 meg-ohms Cm. In one embodiment of the present invention the method for making the ultra-pure water (UPW) is completed once the Process Step 4 of EDI is completed, and in that case the UPW can be stored in a stainless steel holding tank until it is needed. The process for making ultrapure water (UPW), for some embodiments of the present invention, may require about 8 hours to run thru process steps 1 to 4 to make 300 gallons of 18 meg-ohm Cm resistivity UPW. If it is decided to proceed to Process Steps 5-9 for making an embodiment of the invention, then preferably the UPW is prepared and stored for only a few hours before the UPW is carefully mixed with the non-$H_2O$ substance in the next step which is Process Step 3. UltraPure Water (UPW) has about an 18.2 MΩ·cm resistivity. Small concentrations of ion impurities in UPW will greatly reduce UPW resistivity (increased electrical conductivity) which is why measurements of water resistivity a direct and rapid method to analyze quality of a volume of UPW before its use in the present processes of the invention.

Process Step 5—UV Light Exposure (FIG. 11)

Process step 5 is used as a means for sterilizing UPW. For example, the UPW may be treated with UV radiation at 260 nm for about 20 minutes. One option is to perform this UV radiation exposure of the UPW while the UPW is recirculating in a tank with a closed recirculation loop (see FIG. 12 for details). In one embodiment a volume of 300 Gallons of UPW is recirculated in a tank with a closed recirculation loop for at least 20 minutes. For example, the invention embodiments of the process for making the invention which are being tested in a Tampa, Fla. clean room 1208 (see FIG. 12) indicate that the UV treatment of the UPW can heat the UPW to between 80-98° F. from its initial of 70° F.-85° F. (the temperature of the water supply entering the clean room 1208. Studies will test making invention embodiments at other temperature ranges for their utility in making the invention embodiments. The temperatures of the water processing in the present patent application are merely example temperatures. The process of making the invention is conceived to be possible with at any liquid water temperature but may need various parameters of the process of making the invention may need to be modified or optimized further.

Process Step 6—Initial Mixing of Non-$H_2O$ Substance(s) with 1 Gallon of UPW (FIG. 11)

The mixing of non-$H_2O$ substance(s) with UPW preferably takes place in two separate containers. This allows one to carefully prepare the mixture of the Non-$H_2O$ substance(s) with UPW and to minimize how much air and dust may get into the process batch at this stage. First a particular formulation of non-$H_2O$ substances is selected to make almost 300 gallons of the composition of the invention. The Detailed Description of the Invention later on provides examples of formulations of the present invention.

In a "clean room" with Hepa air filtration, one method is to place 30 ounces of UPW 1201 in a 32 ounce commercial blender 1202 such as a Blendex. One third of the non-$H_2O$ ingredients 1203 are then added to the ultrapurified water 1201 in the blender 1202. The UPW should be at least 15 meg-ohm cm resistivity. More preferably the resistivity UPW is between 16-18 meg-ohm cm. The mixture 1205 of UPW 1201 and non-$H_2O$ ingredients 1203 is then mixed by the blender 1202 for a period of time selected from the group consisting of 0.5, 1, 1.5, 2, 2.5, 3, 3.5, 4, 4.5, and 5 minutes. A blending time more than three minutes is used only if there the non-H2O substance that is being used has a poor water solubility. Optionally, three such blender 1202 mixings will be ultimately done one after the other and combined. This creates about one gallon of a mixed concentrate 1205 of the non-$H_2O$ substance in UPW. Some air may have been taken up into the gallon of the mixed concentrate.

Process Step 7—Blending of the 1 Gallon Concentrate 1205 into 300 Gallons of UPW (FIG. 11)

Once mixed concentrate 1205 has been prepared by process step 6, then process step 7 is started. For process step 7, a closed mixing tank 1206 to which has been added 300 gallons of UPW 1207 in the clean room 1208 is pumped in a closed recirculation loop 1209 from the tank bottom drain 1214 to the top entry port of mixing tank 1206 using recirculation pump 1210. The closed mixing tank 1206 has a micron-size air filter 1211 to shield the tank contents from any dust particle introduction. While the mixing tank 1206 is recirculating the 300 gallons of UPW 1207, the gallon of the mixed concentrate 1205 is slowly pumped over about 20 minutes using a concentrate pump 1212 and a pipe 1200 to slowly add the mixed concentrate 1205 into mixing tank 1206 containing the 300 gallons of UPW 1207. As a result, after a minimum of 20 minutes the process ensures that the mixing tank 1206 contains a blended aqueous formulation 1213 of about 300 gallons in volume. When the term "non-$H_2O$ substance 1203" is used it means the same thing as the "non-$H_2O$ ingredients 1203".

Invention Process Temperatures at Tampa, Fla. Prototype Invention Process Facility At the inventor's production facility in Tampa, Fla., the warm weather causes the blended aqueous formulation 1213 at the end of Process Step 5 to have a temperature running between 77° F.-98° F. For the present example experiment, blended aqueous formulation 1213 comprising a blend of the UPW 1201, the UPW 1207 and the non-$H_2O$ substance 1203 at the end of Process Step 5 was measured to have a temperature of 96.4° F., a pH of 6.06, and an oxidation-reduction potential (ORP) of 89.5 mV. The pH and ORP values measured at the end of process step 5 have different values depending upon the chemistry of the ingredients once mixed in the UPW. The term "additives to the UPW" shall mean the same as "the non-$H_2O$ substance added to the UPW". For some embodiments of the present invention, in the Process steps 1 to 5, the temperature of the UPW, its pH, and the ORP will be adjusted and controlled before proceeding to Process step 6. One method of controlling the UPW temperature, pH, and ORP for the present invention is to use a controlled temperature clean room and tanks with cooling equipment. Also, a pH buffer and an ORP buffer system can be included in the UPW containing the non-$H_2O$ substance to control the pH and ORP.

Process Step 8—Reducing the Size of Water Clusters in the UPW Containing Non-$H_2O$ Substance(s).

Figure 12:
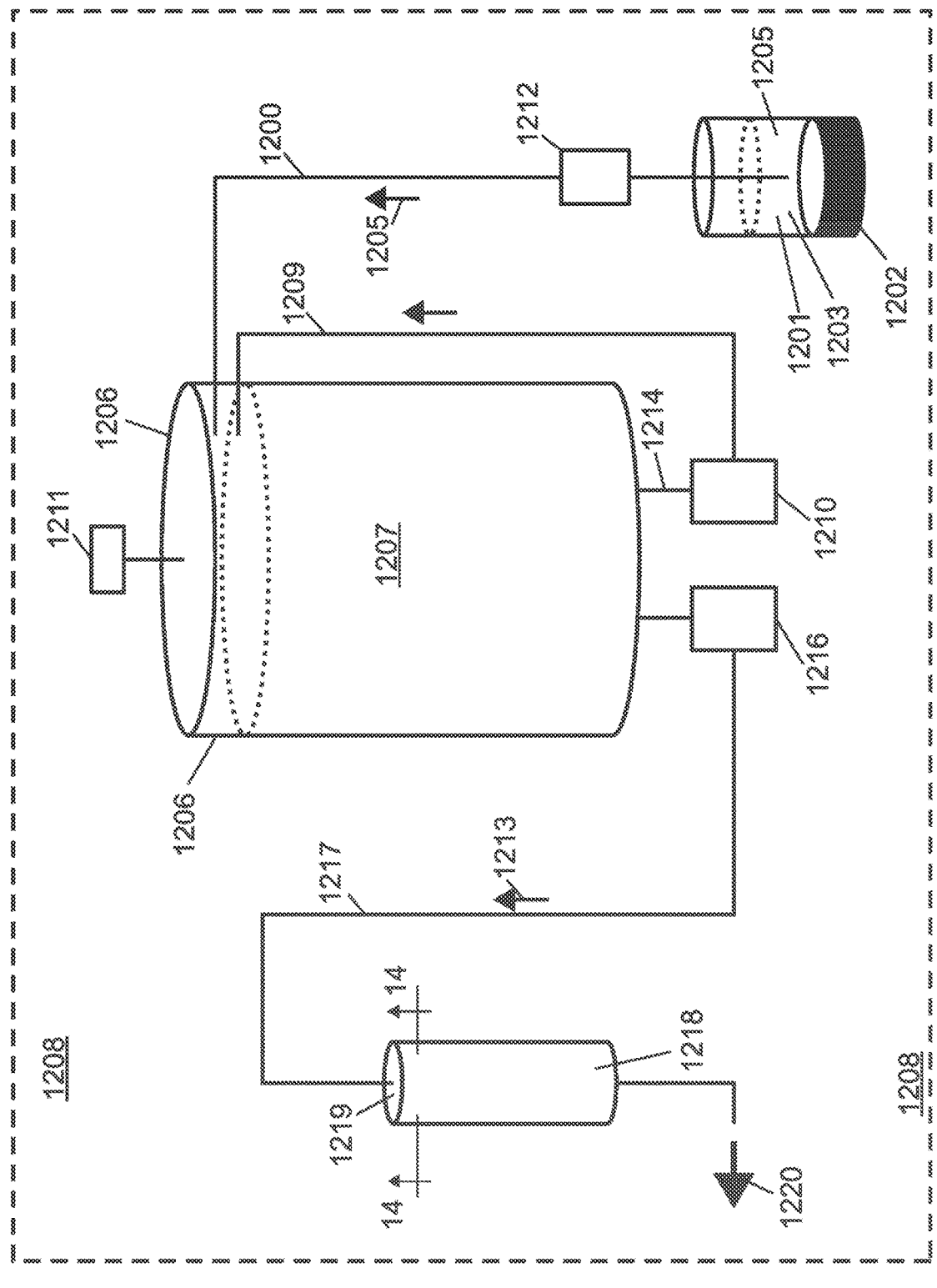
FIG. 12 depicts a highly simplified schematic of an inventive process for making some product embodiments of the present invention in a clean room 1208. Note that in the hollow cylinder 1218 depicted on far left of FIG. 12, that there is a Cross Section A view notation across a top portion of depicted hollow cylinder 1218. See FIG. 14 for the Cross Section A view.

Process Step 8 and its apparatus are well detailed in FIG. 12. Process Step 8 is performed so as to reduce the size of water clusters in blended aqueous formulation 1213. Blended aqueous formulation 1213 is pumped by a variable speed controlled pump 1216 using a transfer pipe 1217 from the closed mixing tank 1206 to a hollow cylinder 1218. The cylinder top 1219 of the hollow cylinder 1218 has a 1 inch inner diameter (ID) center top hole 1221 as an access means for the transfer pipe 1217 to deliver the blended aqueous formulation 1213 comprising UPW 1201, UPW 1207, and non-$H_2O$ substance(s) 1203 into the hollow cylinder 1218. The fluid pressure in the transfer pipe 1217 may be varied by changing the speed of the transfer pipe pump 1216. The fluid pressure in the transfer pipe 1217 is selected from the group consisting of 10-20 psi, 20-30 psi, 30-40 psi, 40-50 psi, 50-60 psi and 60-70 psi. The inventors discovered that the transfer pipe 1217 fluid pressure surprisingly and significantly affects the size of water clusters in the UPW containing non-$H_2O$ substance(s). If the transfer pipe 1217 fluid pressure is too low during the process step 8 process, then there is an insufficient decrease in the size distribution of the water clusters in the UPW containing non-$H_2O$ substance(s). When the transfer pipe 1217 fluid pressure is too high during the process step 8 process then there is an unwanted increase in the size of the water clusters in the UPW containing non-$H_2O$ substance(s). Thus for some embodiments, the invention apparatus for the process step 8 functions with optimum transfer pipe 1217 fluid pressure between about 25-50 pounds per square inch (psi), more preferably about 30-40 psi. For other embodiments for the invention apparatus, the psi values for the fluid pressure in transfer pipe 1217 will be different because the fluid pressure in transfer pipe 1217 depend upon the various sizes of the diameters, shapes and lengths of the invention apparatus pipes, jets, and chambers which are critical to process step 8 fluid path flow. Specific variables include transfer pipe 1217 length and ID, nozzle 1222 and nozzle jet(s) 1223 lengths, dimensions and orientations, and hollow cylinder 1218 dimensions and exit flow dimensions, as well as the temperature and the aqueous viscosity of the blended aqueous formulation 1213. Optionally, during the pumping of the blended aqueous formulation 1213 the pressure in the transfer pipe 1217 may be stepped up and down between various selected pressures between various selected flow rates either manually by a process operator or automatically by a computer program algorithm providing a flow fluctuation wave form instructions to a microprocessor regulating the invention process apparatus. For some embodiments of the invention, the transfer pipe pump 1216 is used to create a transfer pipe 1217 fluid pressure between about 20-60 pounds/square inch (psi), more preferably between about 27-53 psi.

In addition, the fluid flow rate in the transfer pipe 1217 is directly proportional to the transfer pipe 1217 pressure. By varying the transfer pipe pump 1216 speed, the flow rate in the 1" ID transfer pipe 1217 may be selected from the group consisting of 10-25, 10, 11, 12, 14, 15, 16, 18, 20, 22, 24, and 25 gallons per minute (gal/min). Preferably the flow rate in a 1" ID transfer pipe 1217 is between 12-18 gal/min and more preferably the transfer pipe 1217 flow rate is 14-16 gallons per minute. Optionally, during the pumping by the transfer pipe pump 1216, the transfer pipe 1217 flow rate may be stepped up or down between various selected flow rates either manually by a process operator or automatically by a computer program algorithm providing a flow fluctuation wave form instructions to a microprocessor regulating the invention process apparatus.

See Table 1 for a Process step 8 study of the flow rate (10-16 gallons per minute) dependence of some measureable fluid properties in the transfer pipe, in the hollow cylinder, and after expulsion from the hollow cylinder. See FIG. 12 for the process 8 apparatus. The "before" sample is taken from transfer pipe 1217 "before" the hollow cylinder 1218 where the water cluster size is reduced during process step 8 process. The "after" sample is taken from drain pipe 1235 "after" the hollow cylinder 1218 where the water cluster size is reduced during process step 8 process. First, there is noticed a flow dependent centrally-located vertical vapor space in the hollow cylinder 1218 that forms soon after flow is initiated. The vertical vapor space is wider in diameter at lower flow rates through the hollow cylinder 1218 perhaps due to lower flow rates being associated with lower fluid driving pressures in transfer pipe 1217. Table 1 also lists that there is a before sample versus after sample 1-2° F. cooling of the blended aqueous formulation 1213, and a before sample versus after sample 1.5 pH units drop in the pH of the blended aqueous formulation 1213 as it passes through the hollow cylinder 1218. However, at the lowest flow rate of 10 gallons per minute the pH drop is only about 0.6 pH units. If the pH drop in the blended aqueous formulation 1213 was due to a longer period of air contamination mixing of acidifying carbon dioxide, then a larger pH drop would have been expected to occur at the lowest flow rate, but this is not the case. While the flow rate changes may be small, certainly the process 8 step is not an exothermic process. It is a rapid acidifying process for reasons unknown to the inventors at present. Associated with the pH decline of 0.63-1.57 pH units, there is a before sample versus after sample increase in the oxidation-reduction potential (ORP) of +51 to +59 mV.

TABLE 1

Process Step 8 Example - Study of Flow Rate Dependence of Fluid Properties in the Transfer Pipe, in the Hollow Cylinder, and after expulsion from the Hollow cylinder.

| Transfer pipe flow rate (gallons/minute, gal/min) | 16 gal/min | 14 gal/min | 12 gal/min | 10 gal/min |
|---|---|---|---|---|
| Hollow cylinder inner dimensions in inches (width ", length ") | 4" × 18" | 4" × 18" | 4" × 18" | 4" × 18" |
| Temperature before (° F.) | 96.4° F. | 96.4° F. | 96.4° F. | 96.4° F. |
| Temperature after (° F.) | 94.5° F. | 94.5° F. | 95.3° F. | 95.4° F. |
| pH "before" | 6.06 | 6.06 | 6.06 | 6.06 |
| pH "after" | 4.49 | 4.49 | 4.49 | 5.43 |
| ORP (millivolts, mV) before | +89.5 mV | +89.5 mV | +89.5 mV | +89.5 mV |
| ORP (millivolts, mV) after (Oxidation Reduction Potential) | +148.6 mV | +148.6 mV | +146.3 mV | +140.9 mV |

A particularly important objective of embodiments of the present invention is to use an embodiment of process step 8 to modify water clusters in the UPW containing the non-$H_2O$ substance(s) so as to create an aqueous medium product with reduced size water clusters containing the non-$H_2O$ substance(s). When process variables have been optimized, then the reduced size of the water clusters containing the non-$H_2O$ substance(s) in the aqueous medium product has been found to possess surprisingly improved bioavailability compared to ordinary water containing the non-$H_2O$ substance(s). In other words, an important objective of the invention is that the process embodiments of the invention make improved bioavailability products. The product embodiments for various use formulations are generally described in some locations of the patent application by the term "product 1220". See FIG. 12, FIG. 13.

Quality Control Testing of Water Cluster Size Using the Malvern Zetasizer

Figure 7:
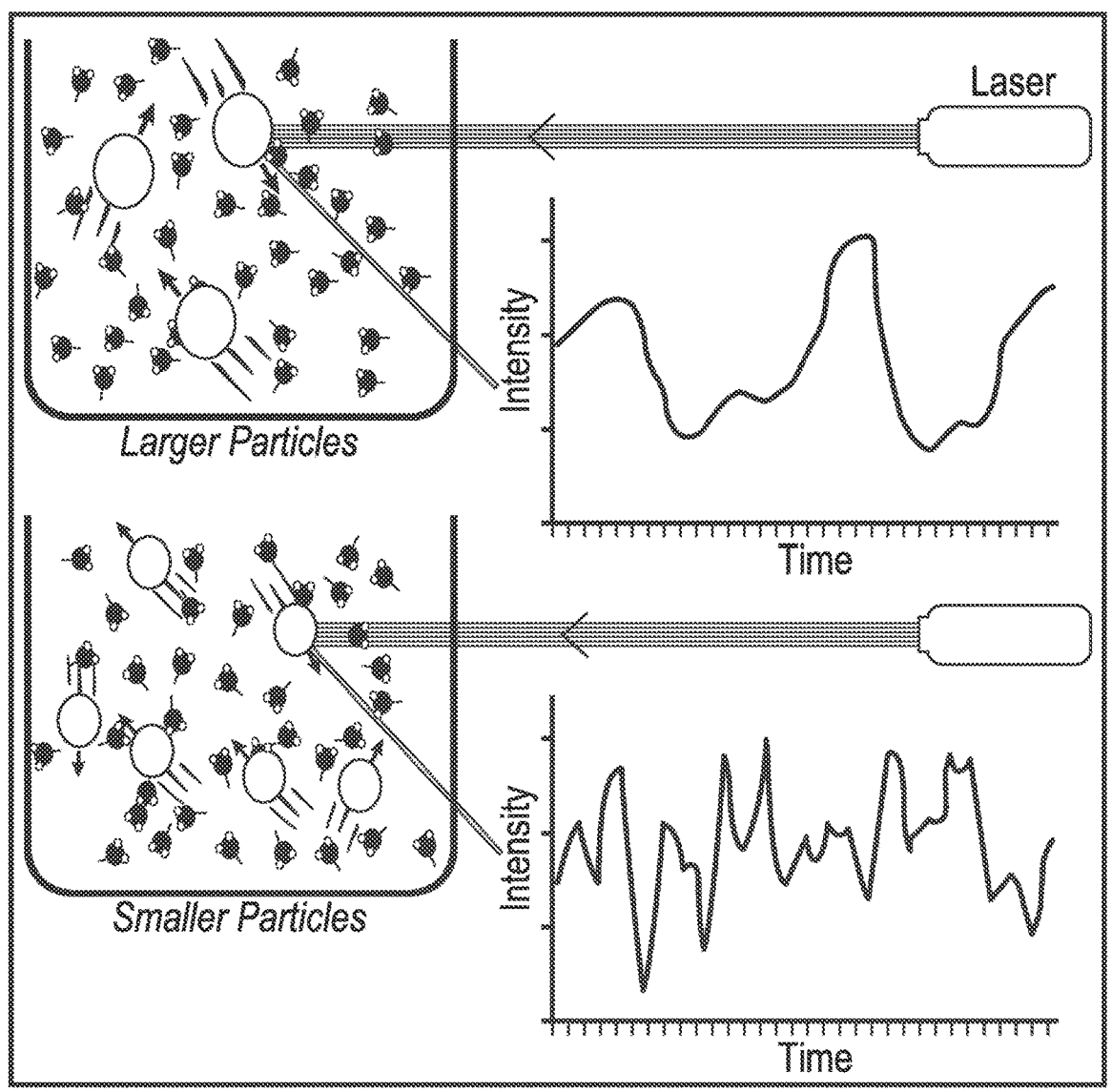
FIG. 7 depicts a method for measuring nano-sized particles by dynamic light scattering (DLS). Depicted is a hypothetical DLS test with two samples. A larger particles sample is being studied in the top beaker and a smaller particles sample is being studied in the bottom beaker. A monochromatic light source, usually a laser, is shot through a polarizer and into a sample. The scattered light then goes through a second polarizer where it is collected by a photomultiplier and the resulting image is projected onto a screen. There is a speckle pattern. All of the molecules in the solution are being hit with the light and all of the molecules diffract the light in all directions. The diffracted light from all of the molecules can either interfere constructively (light regions) or destructively (dark regions). This process is repeated at short time intervals and the resulting set of speckle patterns are analyzed by an auto-correlator that compares the intensity of light at each spot over time. The polarizers can be set up in two geometrical configurations. One is a vertical/vertical (VV) geometry, where the second polarizer allows light through that is in the same direction as the primary polarizer. In vertical/horizontal (VH) geometry the second polarizer allows light not in same direction as the incident light. Malvern Instruments makes a DLS instrument which also measures a Zeta potential.
Figure 8:
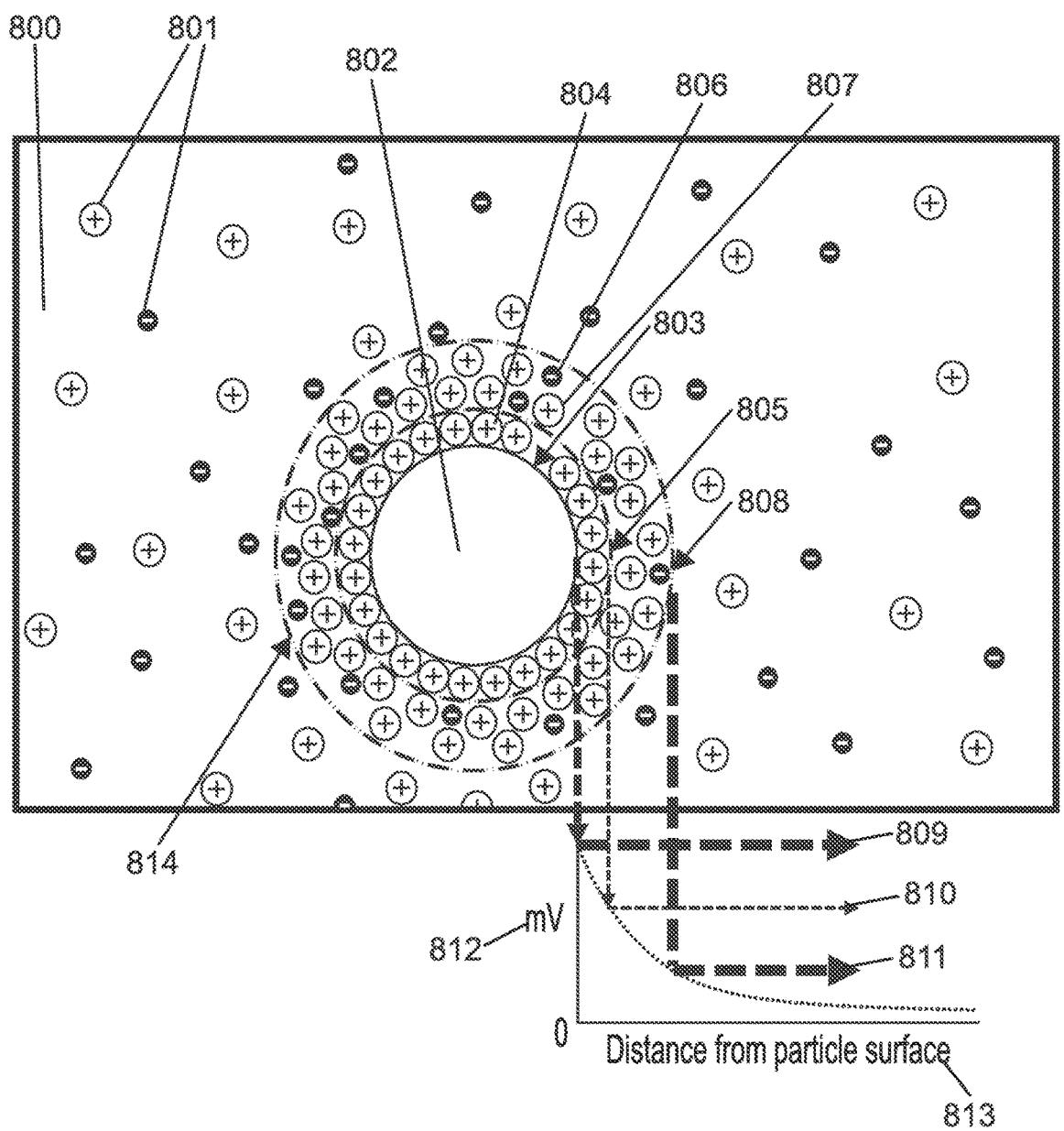
FIG. 8 depicts a prior art diagram of a theoretical model for a radial electrostatic charge distance 813 (mv) neutralization 812 of the static charge on the surface of a colloidal charged particle 802 at an interface 807 with an ionic aqueous medium 800, 801. In this aqueous radial electrostatic charge neutralization model there are three regions with the potential 809, 810, and 811. This model predicts 2 layers of aqueous ions. There is a measurable Zeta potential 811 but potentials 809 and 810 are theoretical.
Figure 9:
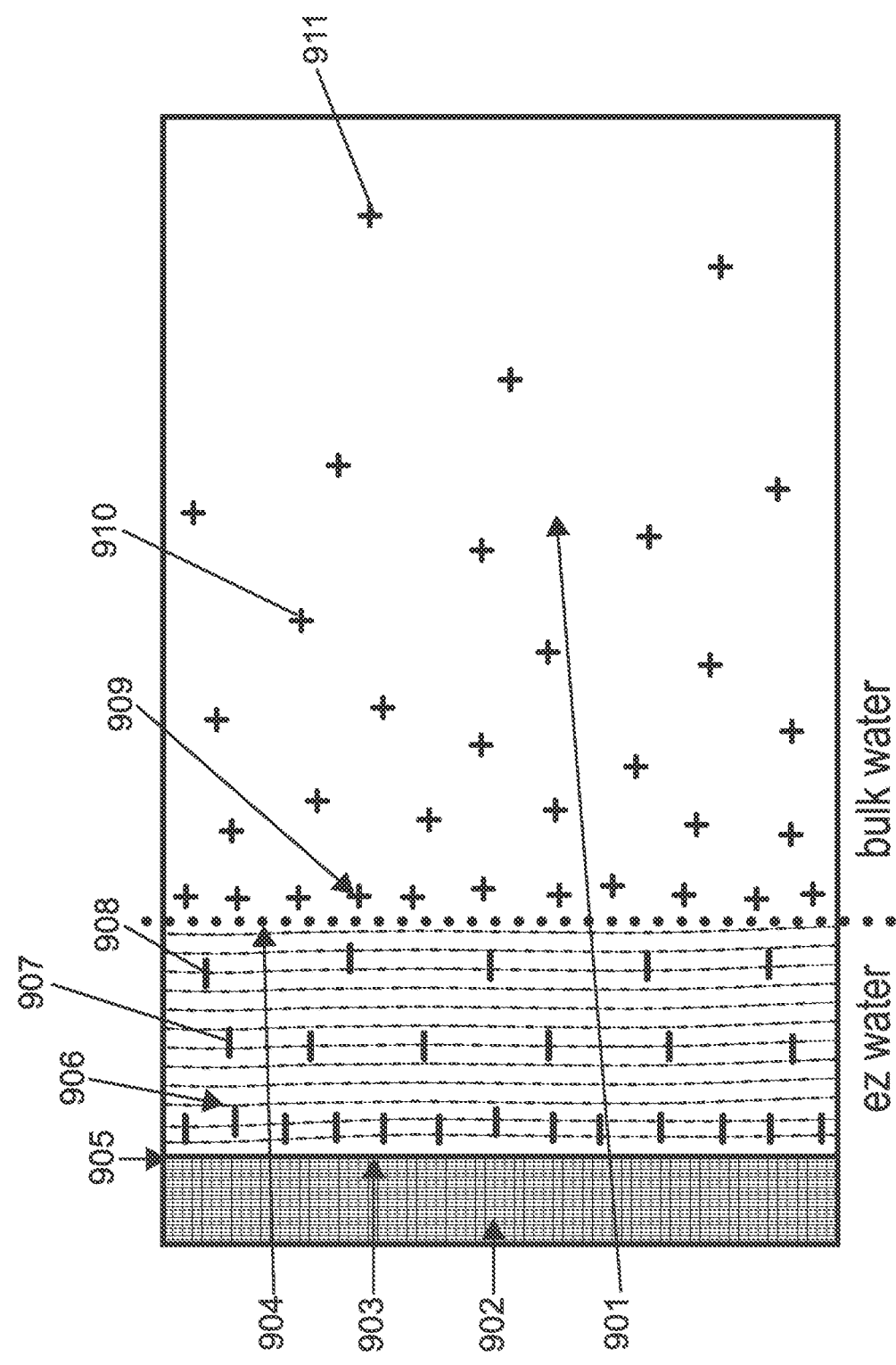
FIG. 9 depicts an alternative prior art theoretical model of the effect of a charged colloid in bulk ionic medium which contrasts with the theoretical model of FIG. 9.
Figure 10:
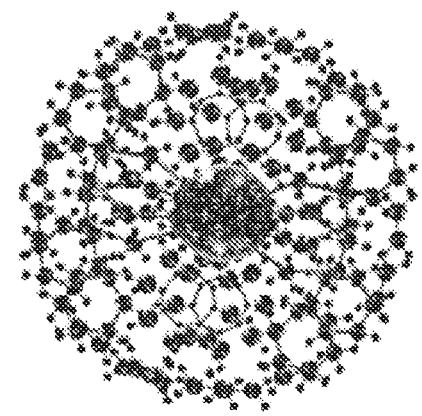
FIG. 10 (left side) presents a hypothetical large size water cluster containing a very large non-$H_2O$ substance (particle). The right side of FIG. 10 presents a small size water cluster containing a non-$H_2O$ substance (particle). The smaller sized water cluster can have an improved bioavailability relative to the larger sized water cluster. Thereoretical reasons for why a small water cluster may have a higher bioavailability than a larger water cluster are an area of a lot of research and scientific controversy as discussed in the Background of the Invention section. The particle size depicted in the larger water cluster appears exaggerated in size when related to the sizes of the depicted water molecules in the water clustering.
Figure 10:
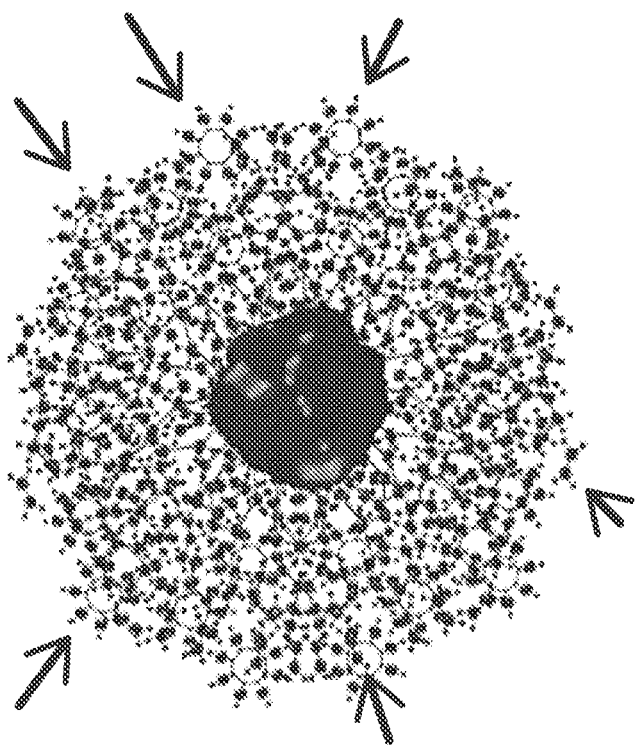

It is an important objective that the present invention test for quality control purposes the water cluster size of the products made for various uses. In this patent application, the term "nanoparticles" shall mean a nano-sized structure and is intended to include, and may be referring to, a nano-sized water cluster. The term nano-sized structure means a structure having a dimension which can be characterized in terms of nanometer units and generally will have a dimension between about 0.1 nanometers to about 10,000 nanometers (nm). In the present patent application's specification when inventors describe invention embodiments, such as mixing tank 1206 mixtures (i.e. blended aqueous formulation 1213), intermediate aqueous mixtures, and final aqueous mixture products (i.e. product 1220), then the term "water clusters" may be used as a part of the starting material, intermediate or final product details. See FIG. 12, FIG. 13. Particles in fluid are constantly moving due to Brownian motion which is defined as the erratic random movement of microscopic particles in a fluid, as a result of continuous bombardment from molecules of the surrounding medium. The extent of the Brownian motion of a particle in a fluid is related to the size of the particles. Larger water clusters move slowly compared to smaller water clusters which move faster due to Brownian motion particle collisions. As depicted in FIG. 7, a particulate (or reflective object in a fluid such as a water cluster size) can be measured in nanometers using a Malvern Instruments Company Zetasizer. Median water cluster sizes in an aqueous formulation of the present invention (invention processes intermediate products) were measured using the Malvern Instruments Company Zetasizer. A direct light scattering (DLS) instrument can analyze the Brownian motion of the particles in fluid under controlled conditions. An aqueous medium sample of the water clusters in a product 1220 (see FIG. 12 for an example of the process apparatus invention embodiment) of the invention or an intermediate product containing particles or water clusters can be tested using the Zetasizer. The Zetasizer tracks the random movement of the water clusters using laser light scattering and then correlates the laser speckle pattern in the sample and from the changes in their intensity can calculate the nanometer sizes of the particles including water clusters in a fluid sample. Essentially the Zetasizer uses DLS (dynamic light scattering) to obtain data on a nano-sized product of the present invention in an aqueous medium, and then uses a set of computer programs to identify various population size details concerning the nano-sized product (nanoparticle) of the present invention in an aqueous medium. The Zetasizer graphs the nanoparticle nanometers size data to depict the nanoparticles' size distributions it becomes clear how many modes of nanoparticles' sizes there are; the mean or median nanoparticle size at each mode, the width of each mode's distribution of sizes, and the skew/kurtosis profile of each mode's size distribution. See FIG. 7 for further details. Water cluster sizes measured in nanometers are reported in FIGS. 15, 16, 17, and 18 in a Malvern Instruments Zetasizer particle size distribution report by volume. The Y-axis of the histogram indicates a linear scale for percent abundance of DLS detected particles (the water clusters). The X-axis of the histogram indicates a logarithmic scale for water cluster size ranging between 0.1 to 1000 nanometers as a function of the particle sizes (the water cluster's sizes). Each report provides a specific computer calculated data particle size histogram. The inventors utilize this histogram data and its calculated median size data for invention embodiment products comprising formulation compositions which are aqueous medium comprising the water clusters with a non-$H_2O$ substance(s). The DLS detected particulates measured and analyzed by the Zetasizer are assumed to be measurements of the invention embodiment water clusters containing non-$H_2O$ substances).

Variations in Hollow Cylinder Apparatus and its Use in Process Step 8

For some apparatus embodiments for the process of making the products of the present invention, the angle of the long axis of the hollow cylinder 1218 is at an angle relative to the ground that may be changed. A vertical angle for the hollow cylinder 1218 is depicted in FIG. 12. Furthermore, the angle of the long axis of the hollow cylinder 1218 is defined 180° from the ground when the cylinder top 1219 is pointing away from gravity by 180°. In this case the tank drain 1227 points down (see FIG. 12 and FIG. 13). In another embodiment the cylinder top 1219 points downward and so the axis of the hollow cylinder is defined as pointing at 0°. When the axis of the hollow tank is horizontal then the axis of the hollow tank 2118 is 90° relative the force of gravity. In some embodiments the angle of the axis of the hollow tank is adjustable by a gimbal means supporting the hollow tank 1218. When the adjustable gimbal means is supporting the hollow tank, then the angle of the long axis of the hollow cylinder 1218 may be selected as an angle from the group consisting of 0°, 15°, 30°, 45°, 60°, 75°, 90°, 105°, 120°, 135°, 150°, 165°, and 180° degrees.

The interior surface 1225 of the hollow cylinder 1218 may be comprised of a plastic, a metal, or a glass material or another material capable of having a smooth surface or may have a smooth ridged surface in some embodiments. The interior surface 1225 should preferably be comprised of a material with a surface which will not undergo a chemical reaction with the blended aqueous formulation 1213. However, in some invention apparatus embodiments, a chemical reaction of the interior surface 1225 of the hollow cylinder 1218 and the blended aqueous formulation 1213 is an object of an embodiment of the invention. Such embodiments and processes will be later described. In one preferred embodiment the hollow cylinder 1218 has a wall 1226 of stainless steel. In some preferred embodiments a portion of the wall 1226 has a window section of the wall of a transparent material or the entire wall 1226 is all transparent material such as a transparent plastic such as transparent polyvinyl chloride (PVC) or polyethylene (PE) plastic. When the wall 1226 is transparent then the flow and continuity appearance of the blended aqueous formulation 1213 during Process step 8 can be monitored.

In some apparatus embodiments of the invention, the hollow cylinder 1218 has a length 1228 which is between two to twenty-five (2-25) times longer than the inner width 1229 of the hollow cylinder 1218. Preferably the hollow cylinder 1218 has a length 1228 which is between 3-10 times longer than the inner width 1229 of the hollow cylinder. 1218. More preferably the hollow cylinder 1218 has a length 1228 which is between 4-8 times longer than the inner width 1229 of the hollow cylinder 1218. Most preferably the hollow cylinder 1218 has a length 1228 which is between 4-5 times longer than the inner width 1229 of the hollow cylinder 1218. In one preferred embodiment for a 300 gallon mixing tank 1206, the transfer pipe 1217 has a 1" ID, the hollow cylinder 1218 has an inner length 1228 between 18-24 inches and an inner width 1229 between 3-5 inches. In a first prototype process example which is depicted in FIG. 12, the inventors used a transfer pipe 1217 with a 1" ID and a hollow cylinder 1218 with an inner length 1228 of about 18 inches and an inner width 1229 of about 4 inches. In a second prototype process the inventors used a transfer pipe 1217 with a 1" ID, and a hollow cylinder 1218 with an inner length 1228 of about 24 inches and an inner width 1229 of about 4 inches. Substitutes to hollow cylinder 1218 are contemplated which have other shape geometries and size ratios. It is planned to scale up the dimensions of the hollow cylinder 1218 for the Process 8 process as there becomes a need for a higher rate Process step 8 and/or a more efficient Process step 8.

Figure 13:
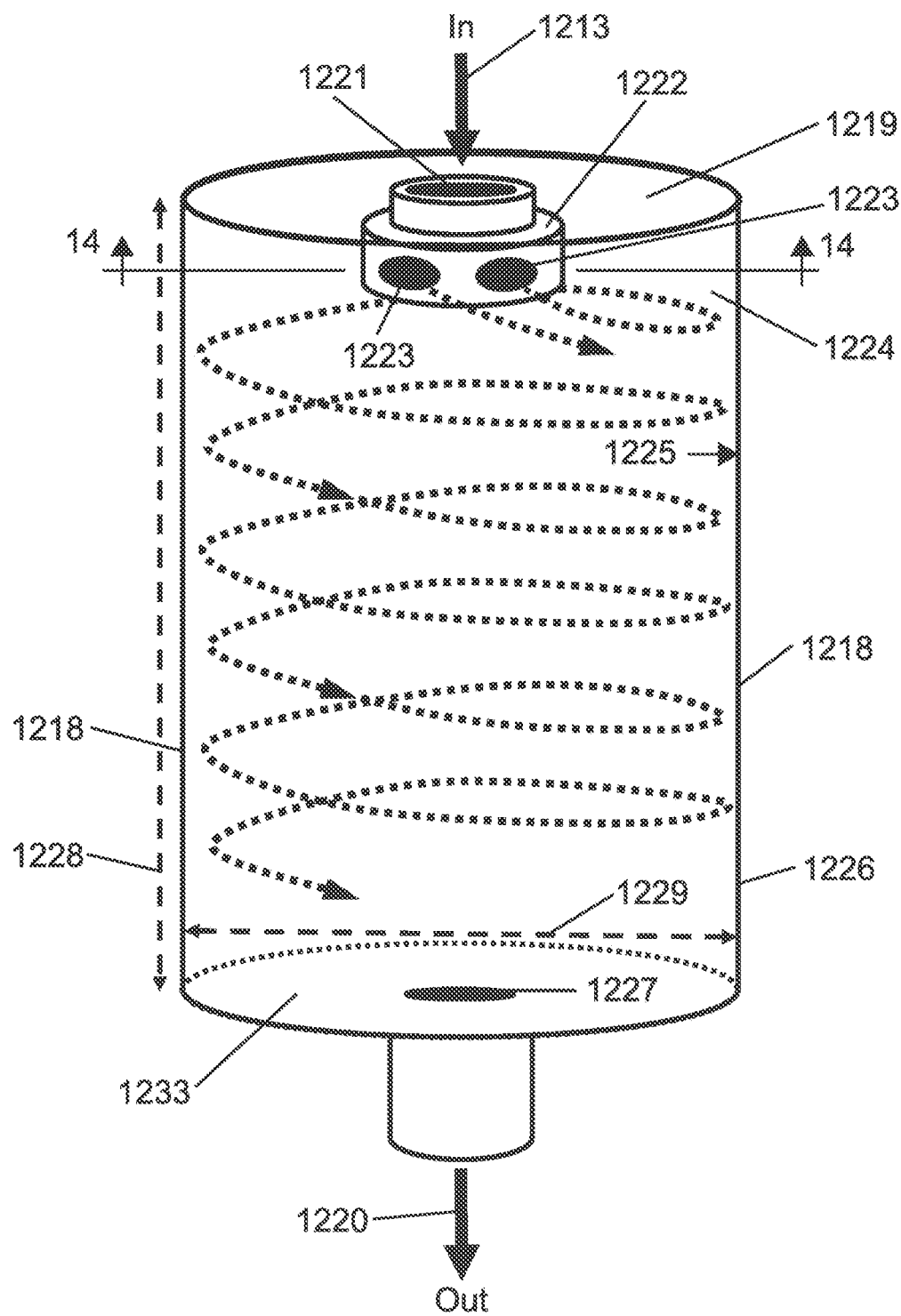
FIG. 13 depicts a schematic with a circular dashed line to represent a hypothetical fluid flow pattern inside hollow cylinder 1218. Rapid flowing blended aqueous formulation 1213 enters hole 1221 at top of hollow cylinder 1218. Reduced size water clusters product 1220 drains out from hole 1227 at bottom 1233 of hollow cylinder 1218.
Figure 14:
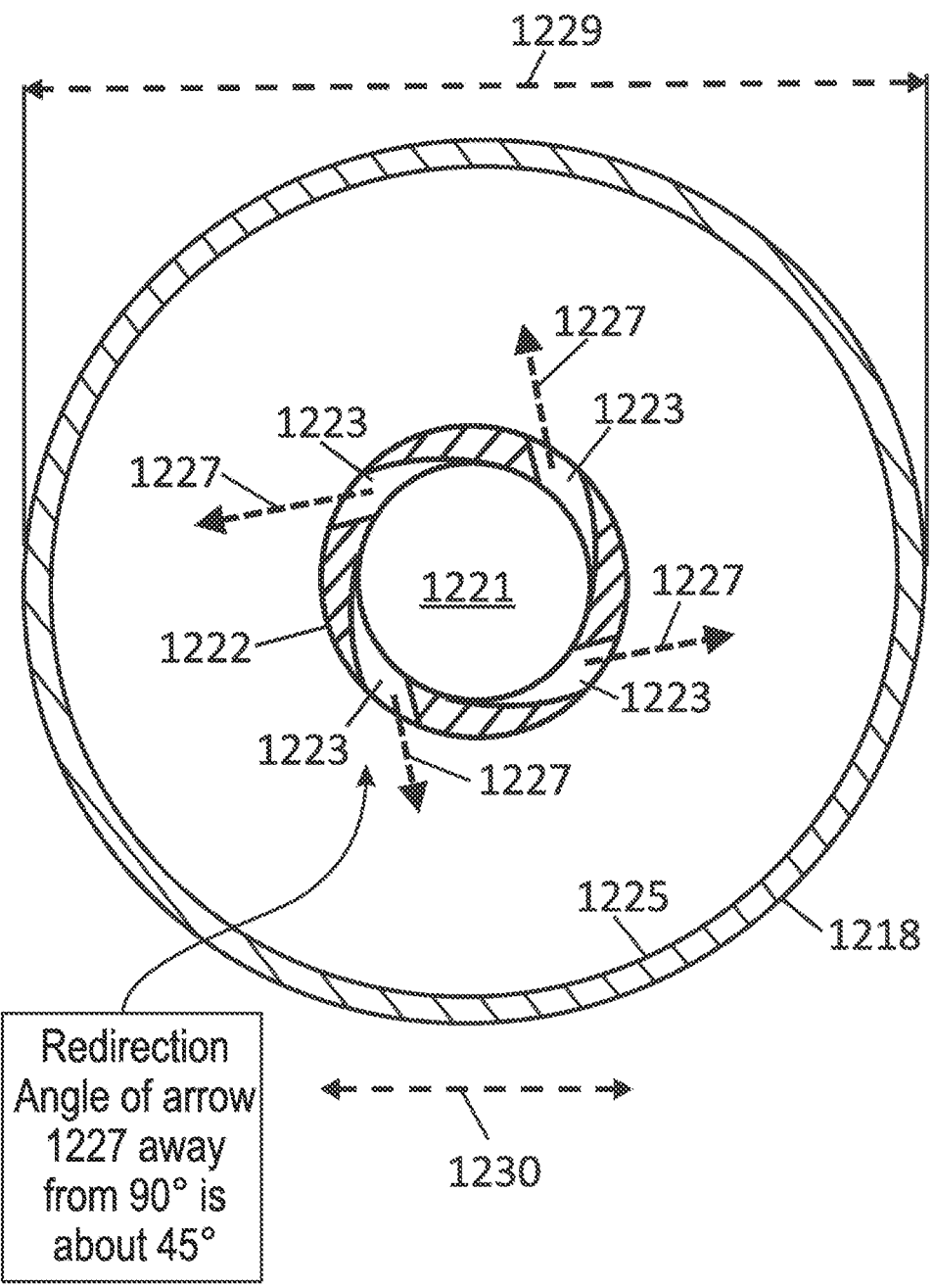
FIG. 14 depicts a schematic of a cross section A of hollow cylinder 1218 with a center located nozzle 1222 in cross section with the nozzle 1222 having jet openings 1223 which have a curved bore hole axis 1227. Rapid flowing blended aqueous formulation 1213 enters hole 1221 at top of hollow cylinder 1218 and then flows out nozzle 1222 via its jet openings 1223 as depicted by curved bore hole axis 1227. The flow depicted by arrows 1227 travels through acute angled and obtuse angled edges of the jet openings 1223.

Cross Sectional View of the Hollow Cylinder 1218 Depicts Example Jet Openings of a Nozzle In one example embodiment of the present invention, FIG. 14 depicts a schematic of a Cross Section A of the hollow cylinder 1218. The same example embodiment is depicted in FIG. 13 in a long axis view to illustrate that the inside of the hollow cylinder 1218 has a nozzle 1222 that is situated near the top 1219 inside of the hollow cylinder 1218. As depicted in FIG. 12, the transfer pipe 1217 is intended to transport a blended aqueous formulation 1213 (i.e, the water clusters in the UPW containing non-1120 substance(s)) from the mixing tank 1206, the water clusters in the fluid medium flow to the end of the transfer pipe 1217 and enter a nozzle(s) 1222. Blended aqueous formulation 1213 in the nozzle 1222 then exits from the nozzle by either by one or more jet opening(s) 1223. In one embodiment of the invention, the jet opening(s) 1223 are positioned inside the top hollow space 1224 of the hollow cylinder 1218. It is preferred that the nozzle 1222 has 1-10 jet openings 1223, more preferably 3 to 6 jet openings 1223, and most preferably 4 jet openings 1223. In some embodiments the inner diameter (ID) of each jet opening(s) 1223 is several-fold smaller than the transfer pipe 1217 ID, with the effect that the inner diameter of the jet opening(s) 1223 can expel the water clusters in the UPW containing non-$H_2O$ substance(s) at a fluid pressure about 2-25 times higher than the fluid pressure in the transfer pipe 1217 fluid.

The number of jet opening(s) 1223 of the nozzle 1222 can be selected from the group consisting of 1, 2, 3, 4, 5, 6, 7, 8, 9, 10, 11, 12, 13, 14, 15, 16, 17, 18, 19, 20 and any combination thereof.

Ratio of Nozzle Outer Width to Cylinder Inner Width Example for Hollow Cylinder 2018

In the example embodiment hollow cylinder 1218 that is depicted in the FIG. 14 Cross Section A, the nozzle outer width 1230 (NOW 1230) and the cylinder inner width 1229 (CIW 1229) are in a ratio of 1:3. In the example embodiment hollow cylinder 1218 that is depicted in the FIG. 13 long axis view the nozzle outer width 1230 (NOW 1230) and the cylinder inner width 1229 (CIW 1229) are in a ratio of 1:5. The test data presented in FIG. 15, FIG. 16, FIG. 17, and FIG. 18 are based on a prototype process (see FIG. 12) in which the hollow cylinder 1218 has a nozzle outer width 1230 and a cylinder inner width 1229 (CIW 1229) in a ratio of 1:4.

For the present invention, some embodiments are contemplated to have in regard to the ratio of the nozzle 1222 outer width 1230 to the cylinder inner width 1229 for the hollow cylinder 1218, with the ratio selected from the group consisting a ratio of about 1:1.15 to about 1.1.25, a ratio of 1:1.25 to about 1:1.33, a ratio of about 1:1.33 to about 1:1.50, a ratio of about 1:1.50 to about 1:1.75, a ratio of about 1:1.75 to about 1:2.0, a ratio of about 1:2.0 to about 1:2.35, a ratio of about 1:2.35 to about 1:2.70, a ratio of about 1:2.70 to about 1:3.0, a ratio of about 1:3.0 to about 1:3.40, a ratio of about 1:3.40 to about 1:3.70, a ratio of about 1:3.70 to about 1:4.0, a ratio of about 1:4.0 to about 1:4.30, a ratio of about 1:4.60 to about 1:4.80, a ratio of about 1:4.80 to about 1:5.10, a ratio of about 1:5.10 to about 1:5.50, a ratio of about 1:5.50 to about 1:5.90, a ratio of about 1.5.90 to about 1:6.50, a ratio of about 1:6.50 to about 1:7.50, and about a ratio of 1:7.50 to about 1:10.0.

Nozzle Jet Openings Example where there is a Redirection Angle which is in Orthogonal Plane to Hollow Cylinder Axis In the prototype embodiment of the present invention the nozzle 1222 can be viewed as having jet openings 1223 which are drawn in black in FIG. 13. During Invention Process step 8 a pressurized blended aqueous formulation 1213 flows into a nozzle fluid entry hole 1221 from distal end of the transfer pipe 1217 using the fluid pressure force generated by operation of a pipe transfer pump 1216. See FIG. 12 for apparatus schematic. The blended aqueous formulation 1213 the flows into nozzle 1222 and out nozzle jet openings 1223. As can be seen in terms of FIG. 13 and FIG. 14, the jet openings 1223 are arranged together around the outer width 1230 of the nozzle in a circular plane which is orthogonal to the long axis of the hollow cylinder 1218. The jet openings 1223 have a shape which when viewed perpendicular to the outer circumference of the nozzle 1222 appears to be an elliptical shape or an oval shape in FIG. 13.

FIG. 14 depicts a "Cross-section A" from FIG. 12 of the hollow cylinder 1218 at the height of the nozzle 1222. FIG. 14 depicts the nozzle in 2D (2D means in two (2) dimensions) as round in circumference but the nozzle 1222 could have a perimeter in a shape which is not round but instead has a perimeter with a 2D shape which is rectangular, square, hexagonal, or any kind of perimeter shape in cross section A view including a shape which is elliptical, or in 3D (3D means in three (3) dimensions) could look like a spherical cap. In FIG. 14, the depicted nozzle 1222 in cross section has four (4) jet openings 1223. Each jet opening 1223 is identified by its own "radially-oriented" headless arrow 1223. Each headless arrow 1223 is radial oriented in that each headless arrow 1223 is pointing perpendicular to the outer surface of each jet opening 1223 of the nozzle 1222 in FIG. 14.

Note also that the shape of the long axis bore hole 1227 of the jet opening 1223 of nozzle 1222 is depicted in FIG. 14 as curving 45 degrees in a counterclockwise direction from the 90 degree angle of the headless arrow 1223 to the nozzle exterior surface arrow 1227. So this counterclockwise backward 45 degree angle has been termed a "redirection angle". Thus the end transfer pipe 1217 pumps blended aqueous composition 1213 to nozzle input opening 1221. From nozzle 1222 input opening 1221, the blended aqueous composition can flow through the nozzle's curved bore holes 1227 which redirect the flow at a redirection angle of 45 degrees counter clockwise. Thus in the nozzle embodiment of FIG. 14 the axis 1227 of the bore hole of the jet openings is redirected by about 45 degrees counter-clockwise to the perpendicular angle" of the headless arrow 1223 to the outer surface of the nozzle 1222. The actual direction of the bore hole of the jet openings 1223 is depicted in FIG. 14 by the dashed arrow labeled 1227. FIG. 14 points out in a text box: "Angle of arrow 1227 away from 90° is about 45°". Using its depiction in FIG. 14, the redirection angle is defined as the change in direction of angle between the perpendicular line to the jet opening(s) 1223. dashed arrow 1227 and Thus the redirection angle is the 45 degree counterclockwise change in direction for fluid being expelled from arrow 1223 to arrow 1227. It is also note that the jet openings 1223 depicted in FIG. 14 have a number of acute angle edges and obtuse angled edges. These angled edges of the jet openings may disrupt laminar fluid flow of the blended aqueous composition 1213 exiting from around these edges in the jet opening(s) 1223.

The transfer pipe pressure mainly controls the flow rate of the blended aqueous formulation 1213. The flow rate of the blended aqueous formulation 1213 may be slightly increased due to the force of gravity acting on the hydrostatic column height of the blended aqueous composition 1213 once it is present in the hollow cylinder 1218. This can only happen because the hollow cylinder 1218 has a hole 1221 at its top 1219 and has a bottom drain hole 1227 at its bottom end 1233. Some flow of the blended aqueous formulation 1213 inside the hollow cylinder will be contacting curved inner surfaces 1225 of the hollow cylinder 1218. Some of this flow contacting the inner surface 1225 should continue to move around, the curved inner surfaces 1225. Inventors have illustrated this possible flow around the inside of the hollow cylinder by the revolving dashed line in FIG. 13. The blended aqueous formulation 1213 that is in the hollow cylinder 1218 will exit from the center hole drain 1230 of the hollow cylinder bottom 1233.

In one embodiment for example, the center drain hole has a 1" ID exit hole. The calculated hollow cylinder volume 1218 is 226 cubic inches for a hollow cylinder with an inner width of 4 inches and a height of 18 inches. A gallon is 231 cubic inches. Therefore for example, when the transfer pipe flow rate is 14-16 gallons per minute, then the fluid in the hollow cylinder is exchanging 14-16 times per minute or getting replaced about once every 4 seconds. When only 10-20 gallons of a 300 gallon batch of the blended aqueous formulation 1213 remains in the mixing tank 1206 during the process step 6 process, then some air from the mixing tank 1206 can get sucked down into the transfer pipe 1217, moves into the transfer pipe pump 1216 and causes a fall in the transfer pipe 1217 fluid pressure and flow rate. When the mixing tank 1206 air reaches the hollow cylinder 1218, then process step 8 will be stopped.

Differences Between the Present Invention and the Prior Art

Processes for making the intermediates and final products by the processes of the present invention have special and conditions and certain limitations that must be emphasized to distinguish the operations and uses and products by the processes of the present invention from the prior art inventions and processes. Water clusters sizes hydrating a non-$H_2O$ substance can be reduced in size by the processes of the present invention to less than 400 nanometers medican size, preferably to less than 300 nanometers median size according to Malvern Zetasizer DLS testing. Water clusters sizes in the range of 2 nanometers to 300 nanometers can be achieved by the present invention provided that the size of the non-H2O substance is recognized as having a significant controlling role in what will be the minimum size water cluster of a particular non-H2O substance enveloped in water clustering. The present invention cannot reduce a water cluster to a size which is smaller than the simplest hydrated water cluster size of a particular non-H2O substance particle.

In contrast to prior art invention processes and apparatuses, the present invention apparatus and process using hollow cylinder 1218 reduces water cluster size in the blended aqueous composition 1213 with the hollow cylinder 1218 functions without any moving mechanical part. The hollow cylinder has no parts inside the hollow cylinder 1218 that are in a movement during process step 8 creating reduced size water clusters. The water cluster size reduction occurring in the hollow cylinder is not using a moving turbine wheel nor a moving fan inside the hollow cylinder. The present invention processes for making an aqueous composition comprising an aqueous medium with reduced size water clusters containing a non-H2O substance is a process method which is not selected from the group consisting of a magnetic mixing process, a moving part mixing process, a moving impellor mixing process, a moving propeller mixing process, a moving turbine part mixing process, a moving solid baffle mixing process, a solid moving part mixing process, a moving solid rotor mixing process, a moving turbine blade mixing process, a motorized moving part mixing process, an electric motor mixing process, an electric current using process, an electric voltage using process, an electric field using process, a static electricity using process, a lightning using process, an electric spark using process, an electric shock using process, a ground isolated electric signal change using process, a ground isolated electrical pulse using process, an electric arc using process, a cathode electrode using process, an anode electrode using process, an electrolysis of water process, an electrophoresis using process, a plasma matter state using process, a permanent magnetic using process, an electromagnet using process, a magnetic field gradient using process, a linear magnetic field using process, a magnetic north field using process, a magnetic solenoid using process, a tesla coil using process, a superconducting magnet using process, a ferromagnetic field using process, a static water flow using process, a gas addition dependent process, a water steam energy using process, a water cleaning treatment plant process, a water evaporation process, a biological energy using process, an enzyme process, an Aquaporin water channel water transport process, an epithelial cell water transport process, a water insoluble liquid flow process, an extrusion of an aqueous medium through a porous wall process, a micron filtration process, an ultrafiltration process, a colloid filter process, a process using boiled water, a process in once distilled water, a non ultrapurified water using process, a cooling source using process, a crushing materials using process, an abrasive slurry using process, and any combination thereof.

It pointed out that what is the present invention depends upon is a pressurized flowing of blended aqueous composition of a volume of ultrapure water containing a non-H2O substance(s) into a nozzle 1222. The jetting of the blended aqueous composition from one or a plurality of jet opening(s) 1223 is a significant utility to the process working to reduced water cluster sizes containing a non-H2O substance particle which could be as small as ions of sodium or another ion. having acute and obtuse edges and a hollow cylinder as a means for causing a disruption of laminar flow, and particularly inside the hollow cylinder outside the jet opening(s) 1223 of the nozzle 1222. It is contemplated to be a preferred object of the present invention that the invention apparatus step 8 process involving the hollow cylinder and processes, functions to efficiently disrupt laminar flow of the blended aqueous composition passing through the jet opening(s) 1223. It is contemplated that said disruption in laminar flow creates a modest increase turbulent flow downstream and outside the jet openings 1223 as a means for reducing water cluster sizes in the blended aqueous composition 1213. Surprisingly process flow rate in the prototype apparatus depicted in FIGS. 12, 13, and 14 need to be fine-tuned because one inventor noticed (based on Zetasizer data) there are flow rates to avoid. Flow rates are too low when 10-12 (ten to twelve) gallons per minute or lower. Such low flow rates lead to an incomplete conversion of the populations of large water clusters with median size 300 to 400 nanometers to water clusters with median sizes 300 or lower nanometers. A flow rate of 14-16 (fourteen to sixteen) gallons per minute works to cause the most complete conversion of the initial mode(s) of median water cluster sizes that are too large for optimal bioavailability for hydration. This optimal flow rate is apparatus size and dimensions dependent. Also a flow as high as 20 gallons per minute increases the number of modes of populations of water cluster sizes and can aggregate water clusters so that new models with a larger size water cluster are occurring.

There is no stirring apparatus (no propeller or water wheel, or impellor or paddle moving inside the hollow cylinder 1218 to break down sizes of the water clusters. There are pumps to pressurize the blended aqueous composition outside the hollow cylinder 1218. However, process testing, see for example Zeatsizer data in FIGS. 15, 16, 17, and 18 show the reduction of median water cluster sizes of the blended aqueous composition occurs predominantly in the process occurring inside the hollow cylinder 1218 and not earlier in the transfer piper 1217 nor in mixing tank 1206. In the hollow cylinder the blended aqueous composition 1213 expelled from the jet openings 1223 should have higher speed flow nearer inner wall 1225 of hollow cylinder compared to its flow speed in center axis of the hollow cylinder. This because the blended aqueous composition is expelled as depicted by arrow 1227 in FIG. 14 towards inner surface 1225 of the hollow cylinder 1218.

Present invention embodiments are using that: (a) is not using magnets, is not using induced magnetic fields, is not using a magnetic non-H2O substance, is not using a magnetic solenoid; is not using electric fields, is not using sparks of electricity, is not shocking with voltage of AC or DC electricity, is not using slow or fast frequency voltage fluctuations; is not using a cathode nor a anode to cause oxidation or reduction reactions, is not causing $H_2O$ electrolysis to form hydrogen or oxygen gases; is not using an electric currents pass in the hollow cylinder; is not causing voltages; is not inducing magnetic fields; is not using a formation of a plasma phase of matter inside hollow cylinder 1218; and is not using gases from the mixing tank 1206 because the UPW is gas-free.

Process is using a continuous stream processing of the blended aqueous composition in a hollow cylinder with an inflow transfer pipe and an outflow drain pipe and not a static location process in a confined tank. The non-$H_2O$ ingredients blended into 1-10 gallons of UPW which represents 0.1 to at most 5% of the total volume of the blended aqueous composition which is processed in process step 8 using the hollow cylinder means. Product leaves the hollow cylinder in just one direction, and there is no recirculation of product in cylinder, and no exothermic reaction in hollow cylinder. The blended aqueous composition pH acidifies in hollow cylinder. Process does not store product under pressure, or with addition of any gases. The use of UV radiation for sterilization of the product is optional. The process causes a size reduction of water clusters, and improves bioavailability. The water cluster size reduction has been stable thus far for 2.5 years. Stability testing of reduced water cluster size shall continue. Additional substances can be added to final product without necessarily disrupting the small water cluster in the invention product. There is a narrow flow range specific range nozzle to cylinder diameters used in invention process apparatus which is hollow cylinder 1218, and the jet openings are directed back from being perpendicular to the nozzle outer circumference surface. There is a preferred ratio of transfer pipe to hollow cylinder diameter and a preferred width to length ratio for the hollow cylinder. There is generally an immediate use of UPW to make products and UPW is prepared on site of product production process. The contact area in hollow cylinder is 99% smooth wall. In some embodiments of the present invention, there are slight to no viscosity changes caused by process step 8 in the hollow cylinder. The gentle hollow cylinder water cluster size reduction process causes less damage to proteins and peptides.

Making the present invention process step 8 involves no use of radiation, microwaves, no use of electromagnetic radiation, no use of ultrasonic energy, no external use of transmitted energy directed at the hollow cylinder, and uses no sound waves.

All plumbing is plastic and non-reactive. Process is not light sensitive but light sensitive ingredient no-$H_2O$ substance may be processed in a dark or red lighted clean room. The change in pH in hollow cylinder to a lower pH may reflect release of H+ from some water clusters or a little atmospheric carbon dioxide getting into the final products drained from hollow cylinder 1218.

Process Step 7 Example—Storage of the Reduced Size of Water Clusters in the UPW Containing Non-$H_2O$ Substance(s).

One example embodiment for Process step 7 involves storing the product 1219 temporarily in a suitable air-tight stainless steel tank 1220. The product 1219 is the aqueous medium comprising the reduced size of water clusters with non-$H_2O$ substance(s). The shelf life of the product 1219 for various use formulations (see below) of the invention is being investigated using long term stability testing.

A. General and Some Specific Embodiments of the Present Invention

In some embodiments, the present invention is a process for reducing water cluster sizes in an aqueous composition containing a non-$H_2O$ substance in order to improve bioavailability of the aqueous composition, the process comprising the steps of: choosing an amount of the non-$H_2O$ substance to add to a volume of ultrapure water; adding the amount of the non-$H_2O$ substance to the volume of ultrapure water in a mixing tank to form a blended aqueous composition containing the non-$H_2O$ substance in the ultrapure water; pumping the blended aqueous composition at a selected flow rate from the mixing tank to a nozzle with one jet opening or a plurality of jet openings inside a hollow cylinder; using the one jet opening or the plurality of jet openings in the nozzle to jet the blended aqueous composition at a higher flow rate into the hollow cylinder; using the higher flow rate of the blended aqueous composition from the one jet opening or the plurality of jet openings inside the hollow cylinder to reduce sizes of the water clusters in the blended aqueous composition of the non-$H_2O$ substance in the ultrapure water; removing the aqueous composition with the reduced size water clusters containing the non-$H_2O$ substance at the selected flow rate from inside the hollow cylinder; and using the reduced size water clusters containing the non-$H_2O$ substance in the aqueous medium to improve the bioavailability of the aqueous composition.

In some embodiments, the present invention is a process wherein more specifically the reduced size water clusters containing the non-$H_2O$ substance in the aqueous medium may have a median water cluster size selected from the group consisting of between about 2 to 10 nanometers, about 10 to 50 nanometers, about 50 to 100 nanometers, about 100 to 200 nanometers, about 200 to 300 nanometers, about 300 to 400 nanometers, and a combination thereof.

In some embodiments, the present invention is a process, wherein more specifically the non-$H_2O$ substance comprises a ionizable salt, and wherein the amount of the ionizable salt added per gallon of the ultrapure water may be selected from the group consisting of between about 10 micrograms to 50 micrograms, about 50 micrograms to 100 micrograms, about 100 micrograms to 200 micrograms, about 200 micrograms to 400 micrograms, about 400 micrograms to 800 micrograms, about 800 micrograms to 1.6 milligrams, about 1.6 milligrams to 3.2 milligrams, about 3.2 milligrams to 6.4 milligrams, about 6.4 milligrams to 30 milligrams, and a combination thereof.

In some embodiments, the present invention is a process, wherein more specifically the ionizable salt may be comprised of ions selected from the group consisting of Aluminum ion, Ammonium ion, Antimony ion, Arsenic ion, Barium ion, Beryllium ion, Bismuth ion, Boron ion, Bromide ion, Cadmium ion, Calcium ion, Cerium ion, Cesium cation, Chloride ion, Chromium ion, Cobalt ion, Copper ion, Dysprosium ion, Erbium ion, Europium ion, Fluoride ion, Gadolinium ion, Gallium ion, Germanium ion, Gold ion, Hafnium ion, Holmium ion, Indium ion, Iodine ion, Iridium ion, Iron ion, Lanthanum ion, Lead ion, Lithium ion, Lutetium ion, Magnesium ion, Manganese ion, Mercury ion, Molybdenum ion, Neodymium ion, Nickel ion, Niobium ion, Osmium ion, Palladium ion, Phosphorus ion, Platinum ion, Potassium ion, Praseodymium ion, Rhenium ion, Rhodium ion, Rubidium ion, Ruthenium ion, Samarium ion, Scandium ion, Selenium ion, Silicon ion, Silver ion, Sodium ion, Strontium ion, Sulfate ion, Tantalum ion, Tellurium ion, Terbium ion, Thallium ion, Thorium ion, Thulium ion, Tin ion, Titanium ion, Tungsten ion, Vanadium ion, Ytterbium ion, Yttrium ion, Zinc ion, Zirconium ion, and a combination of thereof.

In some embodiments, the present invention is a process, wherein more specifically the selected flow rate from the mixing tank to the nozzle may result in a flow volume per minute which is a multiple of the hollow cylinder volume, the multiple selected from the group consisting of about 1 to 2, about 2 to 3, about 3 to 4, about 4 to 5, about 5 to 6, about 6 to 7, about 7 to 8, about 8 to 9, about 9 to 10, about 10 to 11, about 11 to 12, about 12 to 13, about 13 to 14, about 14 to 15, about 15 to 16, about 16 to 17, about 17 to 18, about 18 to 19, about 19 to 20, about 20 to 21, about 21 to 22, about 22 to 23, about 23 to 24, about 24 to 25, about 25 to 26, about 26 to 27, about 27 to 28, about 28 to 29, about 29 to 30.

In some embodiments, the present invention is a process, wherein more specifically the hollow cylinder has an inner width in inches which may be selected from the group consisting of between about 1 to 2 inches, about 2 to 3 inches, about 3 to 4 inches, about 4 to 5 inches, about 5 to 6 inches, about 6 to 7 inches, about 7 to 8 inches, about 8 to 9 inches, about 9 to 10 inches, about 10 to 11 inches, about 11 to 12 inches, about 12 to 13 inches, about 13 to 14 inches, about 14 to 15 inches, about 15 to 16 inches, about 16 to 17 inches, about 17 to 18 inches, about 18 to 19 inches, about 19 to 20 inches, and a combination thereof.

In some embodiments, the present invention is a process, wherein more specifically the hollow cylinder has an inner length in inches may be selected from the group consisting of between about 2 to 4 inches, about 4 to 6 inches, about 6 to 8 inches, about 8 to 10 inches, about 10 to 12 inches, about 12 to 14 inches, about 14 to 16 inches, about 16 to 18 inches, about 18 to 20 inches, about 20 to 22 inches, about 22 to 24 inches, about 24 to 26 inches, about 26 to 28 inches, about 28 to 30 inches, about 32 to 34 inches, about 34 to 36 inches, about 36 to 38 inches, about 38 to 40 inches, about 40 to 42 inches, about 42 to 44 inches, about 44 to 46 inches, about 46 to 48 inches, about 48 to 50, about 50 to 52, about 52 to 54, about 54 to 56, about 56 to 58, about 58 to 60, about 60 to 62, about 62 to 64, about 64 to 66, about 66 to 68, about 68 to 70, about 70 to 72, about 72 to 74, about 74 to 76, about 76 to 78, about 78 to 80 and a combination thereof.

In some embodiments, the present invention is a process, wherein more specifically the ratio of the nozzle outer diameter in inches to the hollow cylinder inner diameter in inches is a ratio which may be selected from the group consisting of about a ratio of 1:1.15 to about 1:1.25, a ratio of 1:1.25 to about 1:1.33, a ratio of about 1:1.33 to about 1:1.50, a ratio of about 1:1.50 to about 1:1.75, a ratio of about 1:1.75 to about 1:2.0, a ratio of about 1:2.0 to about 1:2.35, a ratio of about 1:2.35 to about 1:2.70, a ratio of about 1:2.70 to about 1:3.0, a ratio of about 1:3.0 to about 1:3.40, a ratio of about 1:3.40 to about 1:3.70, a ratio of about 1:3.70 to about 1:4.0, a ratio of about 1:4.0 to about 1:4.30, a ratio of about 1:4.30 to about 1:4.60, a ratio of about 1:4.60 to about 1:4.80, a ratio of about 1:4.80 to about 1:5.10, a ratio of about 1:5.10 to about 1:5.50, a ratio of about 1:5.50 to about 1:5.90, a ratio of about 1.5.90 to about 1:6.50, a ratio of about 1:6.50 to about 1:7.50, and about a ratio of 1:7.50 to about 1:12.0, and a combination thereof.

In some embodiments, the present invention is a process, wherein more specifically the nozzle may have the one jet opening or the plurality of the jet openings selected from the group consisting of 1, 2, 3, 4, 5, 6, 7, 8, 9, 10, 11, 12, 13, 14, 15, 16, 17, 18, 19, and 20.

Preferred are four (4) jet openings on a nozzle of the invention.

In some embodiments, the present invention is a process, wherein more specifically the ratio of sum total area of jet openings on nozzle outer side to area of nozzle inner diameter may be selected from the group consisting of the ratio of about 0.01 to 0.05, a ratio of about 0.05 to 0.10, a ratio of about 0.10 to 0.15, a ratio of about 0.15 to 0.20, a ratio of about 0.20 to 0.25, a ratio of about 0.25 to 0.30, a ratio of about 0.30 to 0.35, a ratio of about 0.35 to 0.40, a ratio of about 0.40 to 0.45, a ratio of about 0.45 to 0.50, a ratio of about 0.50 to 0.55, a ratio of about 0.55 to 0.60, a ratio of about 0.60 to 0.65, a ratio of about 0.65 to 0.70, a ratio of about 0.70 to 0.75, a ratio of about 0.75 to 0.80, a ratio of about 0.80 to 0.85, a ratio of about 0.85 to 0.90, a ratio of about 0.90-1.0, a ratio of about 1.0 to 1.2, a ratio of about 1.2 to 1.5, a ratio of about 1.5 to 1.7, and a combination thereof.

In some embodiments, the present invention is a process, wherein more specifically the nozzle may have one curved bore hole jet opening or a plurality of the curved bore hole jet openings providing an average redirection of the jet opening angle in degrees which may be selected from the group consisting of 0, 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, and 90 degrees. In some embodiments, the present invention is a process, wherein more specifically the nozzle has the curved bore hole jet opening providing the redirection of the jet opening angle as a clockwise redirection of the jet opening angle or as a counter-clockwise redirection of the jet opening angle.

In some embodiments, the present invention is a process, wherein more specifically the process for making an aqueous composition comprising an aqueous medium with reduced size water clusters containing a non-H2O substance is a process method which is not selected from the group consisting of a magnetic mixing process, a moving part mixing process, a moving impellor mixing process, a moving propeller mixing process, a moving turbine part mixing process, a moving solid baffle mixing process, a solid moving part mixing process, a moving solid rotor mixing process, a moving turbine blade mixing process, a motorized moving part mixing process, an electric motor mixing process, an electric current using process, an electric voltage using process, an electric field using process, a static electricity using process, a lightning using process, an electric spark using process, an electric shock using process, a ground isolated electric signal change using process, a ground isolated electrical pulse using process, an electric arc using process, a cathode electrode using process, an anode electrode using process, an electrolysis of water process, an electrophoresis using process, a plasma matter state using process, a permanent magnetic using process, an electromagnet using process, a magnetic field gradient using process, a linear magnetic field using process, a magnetic north field using process, a magnetic solenoid using process, a tesla coil using process, a superconducting magnet using process, a ferromagnetic field using process, a static water flow using process, a gas addition dependent process, a water steam energy using process, a water cleaning treatment plant process, a water evaporation process, a biological energy using process, an enzyme process, an Aquaporin water channel water transport process, an epithelial cell water transport process, a water insoluble liquid flow process, an extrusion of an aqueous medium through a porous wall process, a micron filtration process, an ultrafiltration process, a colloid filter process, a process using boiled water, a process in once distilled water, a non ultrapurified water using process, a cooling source using process, a crushing materials using process, an abrasive slurry using process, and any combination thereof.

In some embodiments, the present invention is a process for reducing water cluster sizes in an aqueous composition containing a non-$H_2O$ substance in order to improve bio-availability of the aqueous composition, the process comprising the steps of: choosing an amount of non-$H_2O$ substance to be added to a large volume of ultrapure water; blending all of the non-$H_2O$ substance in a small volume of the ultrapure water to make a small volume concentrate of the non-$H_2O$ substance in the ultrapure water; wherein the small volume concentrate of the non-$H_2O$ substance blended with the ultrapure water is a percent of the large volume of the ultrapure water that has been chosen, the percent may be selected from the group consisting of a 0.01 to 0.05 percent, a 0.05 to 0.1 percentage, a 0.1 to 0.2 percentage, a 0.2 to 0.3 percent, a 0.3 to 0.4 percent, a 0.4 to 0.5 percent, a 0.5 to 0.6 percent, a 0.6 to 0.7 percent, a 0.7 to 0.8 percent, a 0.8 to 0.9 percent, a 0.9 to 1.0 percent, a 1.0 to 2.0 percent, a 2.0 to 3.0 percent, a 3.0 to 4.0 percent, a 4.0 to 5.0 percent, a 5.0 to 10.0 percent, a 10.0 to 20.0 percent, and a combination thereof; filtering optionally, the small volume concentrate of the non-$H_2O$ substance in the ultrapure water using a clean filter to remove micron-sized particulates from the small volume concentrate, wherein the minimum particle sizes removed by the clean filter may be selected from the group consisting of about 1 to 2 microns, 2.5 microns, 3 microns, 4 to 7 microns, 6 microns, 8-10 microns, 11 microns, and 12-25 microns, and a combination thereof; recirculating the large volume of the ultrapure water in a mixing tank and slowly adding the small volume concentrate of the non-$H_2O$ substance in the ultrapure water to the mixing tank to form a blended aqueous composition containing the non-$H_2O$ substance in an aqueous medium; wherein the large volume amount of the ultrapure water may be selected from the group consisting of about 10 to 20 gallons, about 20 to 50 gallons, about 50 to 100 gallons, about 100-300 gallons, about 300 to 600 gallons, about 600 gallons to about 1000 gallons, about 1000 gallons to about 2500 gallons, and a combination thereof, and wherein the adding of the small volume concentrate volume of the non-$H_2O$ substance in the ultrapure water to the mixing tank to form a blended aqueous composition containing the non-$H_2O$ substance in the aqueous medium may be accomplished over a time period selected from the group consisting of about 1 to 5 minutes, about 5 to 10 minutes, about 10 to 15 minutes, about 15 to 20 minutes, about 20 to 25 minutes, about 25 to 30 minutes, about 30 to 35 minutes, about 35 to 40 minutes, and a combination thereof; pumping the blended aqueous composition at a selected flow rate from the mixing tank to a nozzle with a jet opening inside a hollow cylinder; using the jet opening in the nozzle to jet the blended aqueous composition at a higher flow rate into the hollow cylinder; using the higher flow rate of the blended aqueous composition from the jet opening inside the hollow cylinder to reduce sizes of the water clusters in the blended aqueous composition of the non-$H_2O$ substance in the ultrapure water; removing the aqueous composition with the reduced size water clusters containing the non-$H_2O$ substance at the selected flow rate from inside the hollow cylinder; and using the reduced size water clusters containing the non-$H_2O$ substance in the aqueous medium to improve the bioavailability of the aqueous composition.

In some embodiments, the present invention is a process, wherein more specifically the ultrapure water is prepared by a process comprising the steps of: filtering a volume of water from a supply of water with a carbon filter to produce an amount of water with a low chlorine content; removing ions by a reverse osmosis process from the carbon filtered water with the low chlorine content so as to produce a supply of a deionized water; electro-deionizing the supply of the deionized water from the reverse osmosis process to make an ultrapure water supply; testing the resistivity of the ultrapure water to determine if the resistivity of the ultrapure water is between about 17-18.2 meg-ohm cm; repeating a process step for preparing the ultrapure water and retesting the resistivity of the ultrapure water until the ultrapure water has a measured resistivity of between about 17 meg-ohm cm to 18.2 meg-ohm cm; irradiating the supply of the ultrapure water having a measured resistivity of between about 17 meg-ohm cm to 18.2 meg-ohm cm with ultraviolet light to make a sterilized ultrapure water supply; and storing the sterilized ultrapure water in a stainless steel container until sterilized ultrapure water is needed to be added in the process to make an aqueous composition comprising a aqueous medium with reduced size water clusters containing a non-$H_2O$ substance to improve bioavailability of the aqueous composition.

In some embodiments, the present invention is a process, wherein more specifically the non-$H_2O$ substance comprises a ionizable salt, wherein the amount of the ionizable salt added per gallon of the ultrapure water may be selected from the group consisting of between about 20 micrograms to 100 micrograms, about 100 micrograms to 500 micrograms, about 500 micrograms to 2.5 milligrams, about 2.5 milligrams to 5 milligrams, about 5 milligrams to 10 milligrams, wherein the ionizable salt is comprised of ions selected from the group consisting of Boron ion, Bromide ion, Calcium ion, Cerium ion, Cesium cation, Chloride ion, Chromium ion, Cobalt ion, Copper ion, Fluoride ion, Gold ion, Indium ion, Iodine ion, Iridium ion, Iron ion, Lanthanum ion, Lithium ion, Lutetium ion, Magnesium ion, Manganese ion, Molybdenum ion, Neodymium ion, Niobium ion, Osmium ion, Palladium ion, Phosphorus ion, Platinum ion, Potassium ion, Rhenium ion, Rhodium ion, Rubidium ion, Ruthenium ion, Scandium ion, Selenium ion, Silicon ion, Silver ion, Sodium ion, Strontium ion, Sulfate ion, Tantalum ion, Tin ion, Titanium ion, Tungsten ion, Vanadium ion, Zinc ion, Zirconium ion, and a combination of thereof.

In some embodiments, the present invention is a process, wherein more specifically the hollow cylinder has an inner width in inches which may be selected from the group consisting of between about 3 to 4 inches, about 4 to 5 inches, about 5 to 6 inches, about 6 to 7 inches, about 7 to 8 inches, and a combination thereof, and wherein the hollow cylinder has an inner length in inches selected from the group consisting of between about 8 to 10 inches, about 10 to 12 inches, about 12 to 14 inches, about 14 to 16 inches, about 16 to 18 inches, about 18 to 20 inches, about 20 to 22 inches, about 22 to 24 inches, about 24 to 26 inches, and a combination thereof.

In some embodiments, the present invention is a process, wherein more specifically the selected flow rate from the mixing tank to the nozzle results in a flow volume per minute which is a multiple of the hollow cylinder volume, the multiple selected from the group consisting of about 12 to 13, about 13 to 14, about 14 to 15, about 15 to 16, about 16 to 17, about 17 to 18, about 18 to 19, and a combination thereof. In some embodiments, the present invention is a process, wherein more specifically the reduced size water clusters containing the non-$H_2O$ substance in the aqueous medium have a median water cluster size from about 3 nanometers to about 300 nanometers.

In some embodiments, the present invention is a process, wherein more specifically the non-$H_2O$ substances are added to a volume of 50 gallons of ultrapure water, and wherein the non-$H_2O$ substances comprise:

between about 10 to 1200 milligrams of potassium chloride;

between about 0.0017 to 500 milligrams of vitamin B6;

between about 0.001 to 100 milligrams of ferric chloride;

between about 0.0011 to 800 milligrams of magnesium sulfate;

between about 0.6 to 5000 milligrams of sodium chloride;

between about 0.5 to 75 grams of Ionic Trace Minerals;

between about 1.1 to 1000 milligrams of kelp;

between about 10-500 milligrams of taurine;

between about 5.4 to 100 milligrams of alfalfa; and between about 0.0022 to 60 milligrams of sodium borate.

In some embodiments, the present invention is a process, wherein more specifically the non-$H_2O$ substances are added to a volume of 50 gallons of ultrapure water, and wherein the non-$H_2O$ substances comprise:

between about 0.02 ozs. to 25 ozs. of Capasaicin, between about 0.05 milligrams to 16 milligrams of Resveratrol, between about 10 milligrams to 850 milligrams of Quercetin, between about 500 milligrams to 12,000 milligrams of Vitamin D3, and between about 4 milligrams to 4,000 milligrams of *Panax Ginseng*.

In some embodiments, the present invention is a process, wherein more specifically the non-$H_2O$ substances are added to a volume of 50 gallons of ultrapure water, and, wherein the non-$H_2O$ substances comprise:

between about 0.001 grams to 1000 grams of Synapta;

between about 0.001 grams to 3000 grams of magnesium chloride;

between about 0.0001 liters to 3 liters of Concentrace Trace Mineral Drops; and between about 0.01 grams to 100 grams sodium benzoate.

In some embodiments, the present invention is a process, wherein more specifically the non-$H_2O$ substances are added to a volume of 50 gallons of ultrapure water, and, wherein the non-H$_2$O substances comprise:
  between about 0.001 grams to 1000 grams of Synapta;
  between about 0.001 grams to 3000 grams of magnesium chloride;
  between about 0.0001 liters to 3 liters of Concentrace Trace Mineral Drops; and
  between about 0.01 grams to 100 grams sodium benzoate.

In some embodiments, the present invention is a process, wherein more specifically the non-H$_2$O substances are added to a volume of 50 gallons of ultrapure water, and,
wherein the non-H$_2$O substances comprise:
  between about 0.001 grams to 1000 grams of Synapta;
  between about 0.001 grams to 3000 grams of magnesium chloride;
  between about 0.0001 liters to 3 liters of Concentrate Trace Mineral Drops; and between about 0.01 grams to 100 grams sodium benzoate.

In some embodiments, the present invention is a process, wherein more specifically the reduced size water clusters containing the non-H$_2$O substance in the aqueous medium is used to improve the bioavailability of the aqueous composition for a treatment of a chronic dehydration disorder in a mammal which has been producing physiological problems selected from the group consisting of dyspeptic pain, stress, depression, high blood cholesterol, high blood pressure, excess body weight, chronic fatigue, arthritis, asthma, allergy, insulin independent diabetes, and rheumatoid arthritis.

In some embodiments, the present invention is a process, wherein more specifically the reduced size water clusters containing the non-H2O substance in the aqueous medium is used to improve the bioavailability of a solution administered to a mammal in need of an acute rehydration.

In some embodiments, the present invention is a process, wherein more specifically the reduced size water clusters containing the non-H2O substance in the aqueous medium is used to improve the bioavailability of an aqueous composition of a pharmaceutical which is administered by an oral route, a parenteral route, a pulmonary route, an ocular route, an internasal route, an intravenous route, and a sublingual route of administration.

In some embodiments, the present invention is a process, wherein more specifically the reduced size water clusters containing the non-H$_2$O substance in the aqueous medium is used to improve the bioavailability of the aqueous composition of a beverage.

In some embodiments, the present invention is a process, wherein more specifically the reduced size water clusters containing the non-H$_2$O substance in the aqueous medium is used to improve the bioavailability of a therapeutic water source capable of providing a hydration treatment to a mammal for a hydration benefit selected from the group consisting of a healthy body weight, an increased metabolism, an increased energy levels, a reduced join back pain, an easier flushing a body waste, a prevention of headaches including migraine headaches, alleviating headaches, a better skin hydration and skin health, a slowing of aging, and a stimulation of nutrient intake from food.

B. Experimental Data Examples and Related Process Information Examples

Example 1—Experimental Data on Products of the Invention

The inventors observed a significant reduction in sizes of water clusters in blended aqueous compositions comprising ultrapure water and a non-H$_2$O substance(s). by the Present Invention Process embodiments: The Malvern Zetasizer was used to measure the median sizes of water cluster distributions in invention embodiment process samples taken before and after Process step 8. See FIG. 11 and FIG. 12 for Process steps. Two samples of the blended aqueous composition 1213 of Hangover formulation were sampled from the transfer pipe 1217 (See FIG. 12). Their Malvern Instrument's Zetasizer study reports are provided in FIG. 15 and FIG. 17.

Two samples of the blended aqueous composition 1213 of Hangover formulation after their Step 8 processing using the hollow cylinder 1218 were sampled from the process drain pipe 1235. Their Malvern Instrument's Zetasizer reports are provided in FIG. 15 and FIG. 18.

Figure 15:
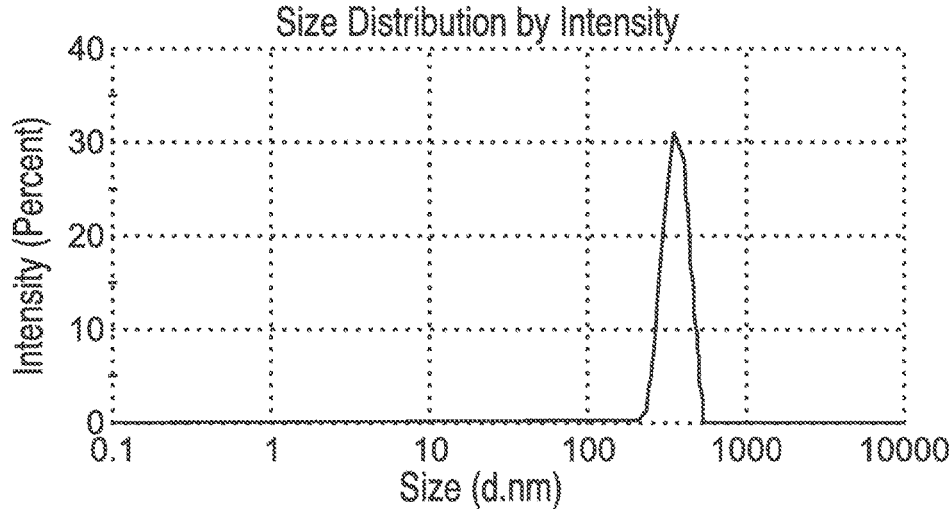
FIG. 15 presents Zetasizer data "Size distribution Reported by Volume" which is measurements of water cluster sizes in a first sample taken by an inventor from the flowing blended aqueous formulation 1213 in the transfer pipe 1217 (see FIG. 12 for transfer pipe 1217 location) BEFORE the flowing blended aqueous formulation 1213 has entered into hollow cylinder 1218. The non-1120 substance is some salt ions, There is a single mode distribution with a reported median water cluster size of 358 nanometers (nm) in the sample data record presented as FIG. 15 and it has a standard deviation of about 58 nanometers. See histogram at bottom of FIG. 15 for size distribution of the measured water clusters in the tested sample.

FIG. 15 presents Zetasizer measurements of water cluster sizes in a first sample taken from the flowing blended aqueous formulation 1213 in the transfer pipe 1217 (see FIG. 12 for transfer pipe 1217 location) BEFORE the flowing blended aqueous formulation 1213 enters into hollow cylinder 1218. The median water cluster size is 358 nanometers (nm) in the sample data record presented as FIG. 15. See histogram at bottom of FIG. 15 for size distribution of the measured water clusters in the tested sample.

Figure 16:
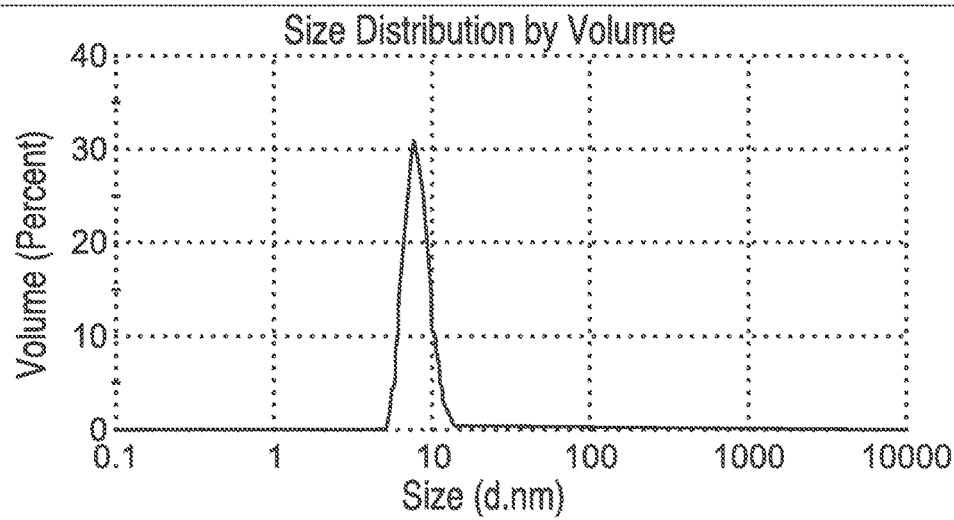
FIG. 16 presents Zetasizer data "Size distribution Reported by Volume" which is measurements of water cluster sizes in a first sample taken from the flowing blended aqueous formulation 1213 in the transfer pipe 1217 (see FIG. 12 for transfer pipe 1217 location) AFTER the flowing blended aqueous formulation 1213 enters into hollow cylinder 1218. The hollow cylinder 1218 process (process step 8, see FIGS. 11, 12, 13 and 14 for details) causes a reduction in the DLS based size measurement on the flowing blended aqueous formulation 1213. The non-$H_2O$ substance is some salt ions. There is a single mode distribution with a reported median size of 8 nanometers (nm) in the sample data record presented as FIG. 16 and it has a standard deviation of about 1.4 nanometers. See histogram at bottom of FIG. 16 for size distribution of the measured water clusters in the tested sample.

FIG. 16 presents Zetasizer measurements of water cluster sizes in a first sample taken from the flowing blended aqueous formulation 1213 in the transfer pipe 1217 (see FIG. 12 for transfer pipe 1217 location) AFTER the flowing blended aqueous formulation 1213 enters into hollow cylinder 1218. The hollow cylinder 1218 process (process step 8, see FIGS. 11, 12, 13 and 14 for details) reduced median water cluster size in the flowing blended aqueous formulation 1213 to a Zetasizer measured median size of 8 nanometers (nm) in the sample data record presented as FIG. 16. See histogram at bottom of FIG. 16 for size distribution of the measured water clusters in the tested sample. FIG. 16 data represents proof of a reduction to practice of the invention. Embodiments of the present invention based on testing of this first sample reduced water cluster size in flowing blended aqueous formulation 1213.

Figure 17:
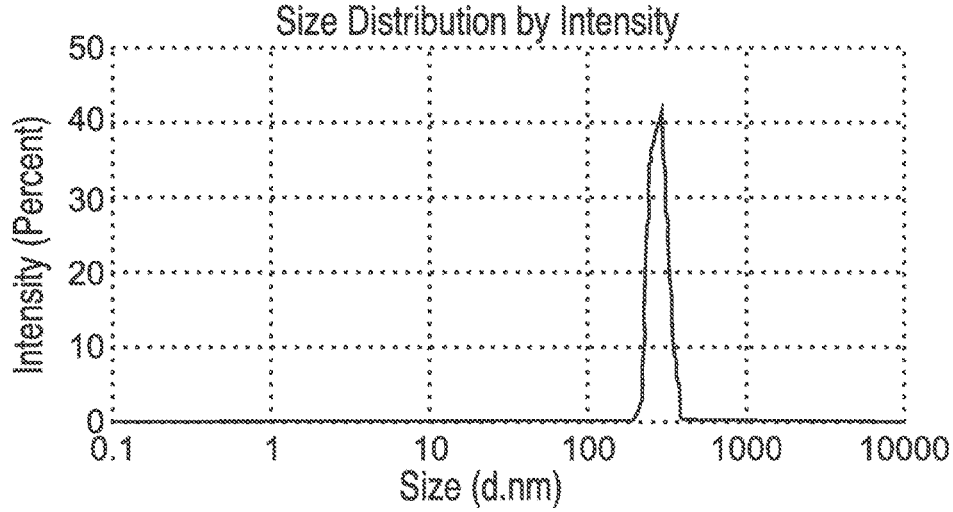
FIG. 17 presents Zetasizer data "Size distribution Reported by Volume" which is measurements of water cluster sizes in a second sample taken from the flowing blended aqueous formulation 1213 in the transfer pipe 1217 (see FIG. 12 for transfer pipe 1217 location) BEFORE the flowing blended aqueous formulation 1213 enters into hollow cylinder 1218. The median water cluster size is 286 nanometers (nm) in the sample data record presented as FIG. 17 with a standard deviation of about 32 nanometers. See histogram at bottom of FIG. 17 for size distribution of the measured water clusters in the tested sample.

FIG. 17 presents Zetasizer measurements of water cluster sizes in a second sample taken from the flowing blended aqueous formulation 1213 in the transfer pipe 1217 (see FIG. 12 for transfer pipe 1217 location) BEFORE the flowing blended aqueous formulation 1213 enters into hollow cylinder 1218. The median water cluster size is 286 nanometers (nm) in the sample data record presented as FIG. 17. See histogram at bottom of FIG. 17 for size distribution of the measured water clusters in the tested sample.

Figure 18:
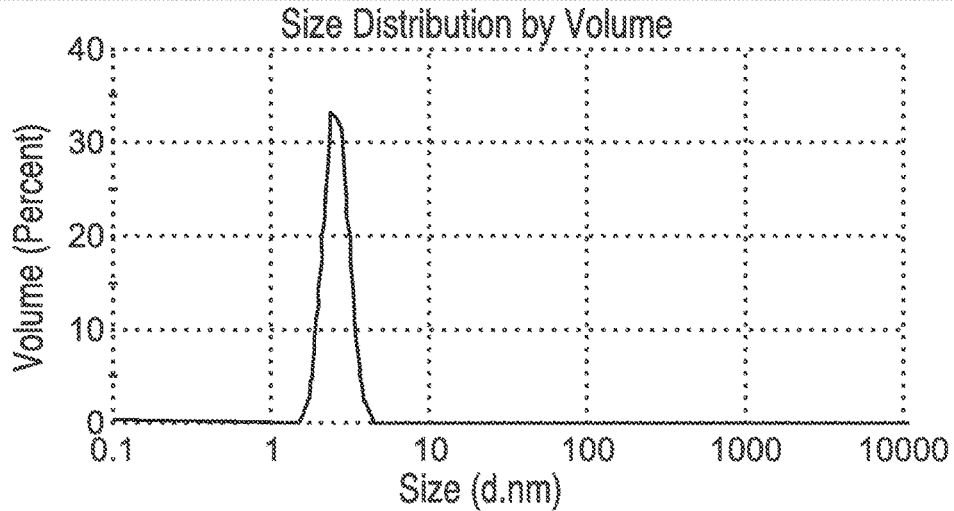
FIG. 18 presents Zetasizer data "Size distribution Reported by Volume" which is measurements of water cluster sizes in a second sample taken from the flowing blended aqueous formulation 1213 in the transfer pipe 1217 (see FIG. 12 for transfer pipe 1217 location) AFTER the flowing blended aqueous formulation 1213 enters into hollow cylinder 1218. The median water cluster size is 2.5 nanometers (nm) in the sample data record presented as FIG. 18 with a standard deviation of about 0.4 nanometers See histogram at bottom of FIG. 18 for size distribution of the measured water clusters in the tested sample.

FIG. 18 presents Zetasizer measurements of water cluster sizes in a second sample taken from the flowing blended aqueous formulation 1213 in the transfer pipe 1217 (see FIG. 12 for transfer pipe 1217 location) AFTER the flowing blended aqueous formulation 1213 enters into hollow cylinder 1218. The median water cluster size is 2.5 nanometers (nm) in the sample data record presented as FIG. 18. See histogram at bottom of FIG. 18 for size distribution of the measured water clusters in the tested sample. FIG. 18 data represents a second example proof of a reduction to practice of the invention. Embodiments of the present invention based on testing of this second sample reduced water cluster size in flowing blended aqueous formulation 1213.

Figure 19:
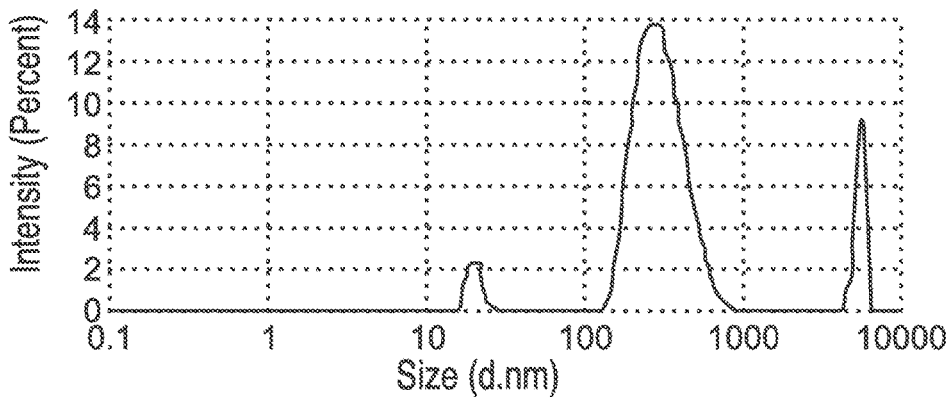
FIG. 19 presents Zetasizer data "Size distribution Reported by Volume" which is measurements of water cluster sizes in an "early" sample taken at the start of operating the process when the flow rate in the hollow cylinder was low and BEFORE the flowing blended aqueous formulation 1213 enters into hollow cylinder 1218. The data unlike
Figure 20:
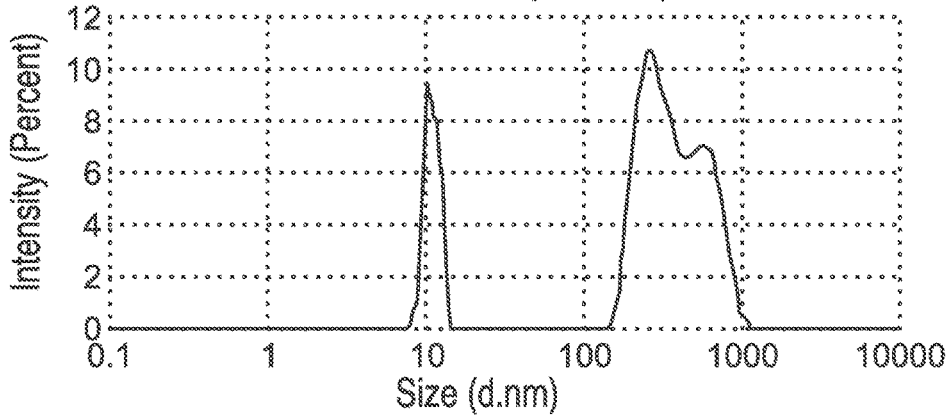
FIG. 20 presents Zetasizer data "Size distribution Reported by Volume" which is measurements of water cluster sizes in an "early" AFTER sample taken soon after the start of operating the process when the flow rate in the hollow cylinder was low. In this AFTER sample the water clusters got incomplete size reduction of water clusters in the aqueous formulation 1213 going through hollow cylinder 1218. from the flowing blended aqueous formulation 1213 in the transfer pipe 1217 (see FIG. 12 for transfer pipe 1217 location) The data is multi-modal unlike FIGS. 15 and 17. The standard deviation is 293 nm for the mode with a median value of 542 nm, and is 108 nm for the data with the median value of 310. The inventor who has worked on the process the longest indicates that low flow through the hollow cylinder 1218 can cause the water cluster distributions problems become multimodal and undergo less size reduction. As typical to exhibit increased median values when forces are too weak to reduce the size of the water clusters. It can be seen that the 84% BEFORE water clusters have median size water clusters of 309 nanometers which decline in abundance AFTER hollow cylinder to 55%. During this time there is 28% creation of 606 nm water clusters and 5% creation of 10 nanometer water clusters. At same time there is a disappearance of 11% large water clusters of 5400 nm. The point of FIG. 20 is to illustrate that low flow rate through the hollow cylinder is ineffective. The inventor MC who has done more than 100 sample studies on water cluster size reducing indicates that there is an optimum flow rate of 14 gallons per minute throught the hollow cylinder 1218 for the present prototype embodiment apparatus. He views the data of FIG. 20 representing low flow (5-10 gallons per minute) experimental results on water cluster size reduction. He found out experimentally and could not have predicted nor was it obvious in any manner that that there is a sensitive bell curve relationship for the dependence of water cluster size reduction on a narrow range of flow rates (gallons per minute) of the blended aqueous composition 1213 flowing through the hollow cylinder 1218. Too high flow rates through the hollow cylinder 1218 also are less efficient at reducing the water cluster sizes.

FIG. 19 presents Zetasizer data "Size distribution Reported by Volume" which is measurements of water cluster sizes in an "early" sample taken at the start of operating the process when the flow rate in the hollow cylinder was low and BEFORE the flowing blended aqueous formulation 1213 enters into hollow cylinder 1218. The data unlike FIGS. 15 and 17 depicts three modes of size distributions with median sizes of 310 nm, 542 nm, and 20 nm. The standard deviation is 293 nm for the mode with a median value of 542 nm, and is 108 nm for the data with the median value of 310. See histogram at bottom of FIG. 19 for size distribution of the measured water clusters in the tested sample. FIG. 19 represents the kind of problem data that can apparently arise when the invention apparatus has not fully yet operational. One inventor is of the opinion that this invention sample absorbed atmospheric air and this would hollow cylinder 1218 for the present prototype embodiment apparatus. He views the data of FIG. 20 representing low flow (5-10 gallons per minute) experimental results on water cluster size reduction. He found out experimentally and could not have predicted nor was it obvious in any manner that that there is a sensitive bell curve relationship for the dependence of water cluster size reduction on a narrow range of flow rates (gallons per minute) of the blended aqueous composition 1213 flowing through the hollow cylinder 1218. Too high flow rates through the hollow cylinder 1218 also are less efficient at reducing the water cluster sizes.

TABLE 2

Tabulated below are supporting Data related to samples taken to measure Size Distributions of Water Clusters in Blended Aqueous Formulation 1213 by Process Step 6.

| Transfer pipe flow rate (16 gallons/minute)* | Sample 1, 4 | Sample 2, 5 | Sample 3, 6 |
|---|---|---|---|
| Hollow cylinder Inner dimensions (width, length, inches") | 4' × 18' | 4' × 18' | 4' × 18' |
| Temperature before (° F.) | 93.2° F. | 93.2° F. | 93.0° F. |
| Temperature after (° F.) | 92.6° F. | 92.6° F. | 92.6° F. |
| Aqueous Medium pH before Step 6 | 7.81 | 5.88 | 5.79 |
| Aqueous Medium pH after Step 6 | 5.64 | 5.71 | 5.82 |
| ORP (millivolts, mV) before | +55.3 mV | +69.1 mV | +76.1 mV |
| ORP (millivolts, mV) after (Oxidation Reduction Potential) | +80.2 mV | +76.3 mV | +81.8 mV |

*Measured viscosity of the Aqueous Medium was 0.8872 centipoise before and after process step 6 process on Samples 1, 2, and 3.
**Samples 1, 2, and 3 contained Hangover Formulation TMC electrolytes and a salt as the non-H2O substance.

modify the water cluster sizes in ultrapurified water (UPW) BEFORE there has been any water cluster size reduction by the present invention.

FIG. 20 presents Zetasizer data "Size distribution Reported by Volume" which is measurements of water cluster sizes in an "early" AFTER sample taken soon after the start of operating the process when the flow rate in the hollow cylinder was low. In this AFTER sample the water clusters got incomplete size reduction of water clusters in the aqueous formulation 1213 going through hollow cylinder 1218. from the flowing blended aqueous formulation 1213 in the transfer pipe 1217 (see FIG. 12 for transfer pipe 1217 location) The data is multi-modal unlike FIGS. 15 and 17. The standard deviation is 293 nm for the mode with a median value of 542 nm, and is 108 nm for the data with the median value of 310. The inventor who has worked on the process the longest indicates that low flow through the hollow cylinder 1218 can cause the water cluster distributions problems become multimodal and undergo less size reduction. as typical. to exhibit increased median values when forces are too weak to reduce the size of the water clusters. It can be seen that the 84% BEFORE water clusters have median size water clusters of 309 nanometers which decline in abundance AFTER hollow cylinder to 55%. During this time there is 28% creation of 606 nm water clusters and 5% creation of 10 nanometer water clusters. At same time there is a disappearance of 11% large water clusters of 5400 nm. The point of FIG. 20 is to illustrate that low flow rate through the hollow cylinder is ineffective. The inventor MC who has done more than 100 sample studies on water cluster size reductioning indicates that there is an optimum flow rate of 14 gallons per minute throught the Example 2: Products with Reduced Size Water Clusters have Improved Bioavailability Inventors who have been using the Malvern Zetasizer to measure the median size of the water clusters in experimental product embodiments of the present invention, have also been evaluating the improvements in bioavailability of experimental product embodiments of the present invention which arise from the novel invention process of the present invention. The inventors observed that a composition with aqueous medium comprising UltraPure Water (UPW) and a non-H2O substance(s) has improved bioavailability when the median size of the water clusters in the aqueous medium is reduced to below 400 nanometers, preferably below 300 nanometers size, more preferably to below 250 nanometers size based on using a Malvern Zetasizer to determine median size of the water cluster size of the products of the invention. The inventor observed that an aqueous medium containing a non-$H_2O$ substance water clusters with a median size exceeding 400 nanometers can have very poor bioavailability.

The inventors conclude that aqueous medium compositions which comprise a blended mixture of UPW with a non-H2O substance(s) and which have been manufactures by a process of the present invention are found to have (a) reduced size water clusters based on Malvern Zetasizer testing by the inventor, and (b) an improved bioavailability based on bioavailability testing by the inventor.

In general, several of the inventors have experimentally observed that various invention process embodiments can be used to make compositions which comprise a blended mixture of UPW with a non-H2O substance(s) in which the aqueous medium has reduced size water clusters based on Malvern Zetasizer measurements of the median size of the populations of the water clusters in the products made by the invention processes. By a process embodiment of the present invention the median size of the water clusters in the blended mixture of the UPW with the non-H2O substance(s) (according to Malvern Zetasizer measurements) can be made to have a median size less than 400 nanometers, preferably to a median size between 1 to 300 nanometers.

Example 3: Storage Stability of Invention Products Having Reduced Size of Water Clusters in the UPW Containing Non-$H_2O$ Substance(s)

In one example, the Process step 7 product is stored temporarily in a suitable air-tight stainless steel tank 1220. The product 1219 is the aqueous medium comprises the reduced size of water clusters with non-$H_2O$ substance(s). The shelf life of the product 1219 for various use formulations (see below) of the invention is being investigated using long term stability testing. Product 1219 development and DLS measurements of product 1219 water cluster size distributions have been an ongoing experiment project for eight years by one of the inventors. Surprisingly and quite unexpectedly, the inventor has discovered that the measured water cluster size distributions in one batch of a product 1219 formulation has remained substantially unchanged and is stable after 8 years after it was made by the present invention process. In a second batch, the inventor confirmed that the measured reduction in water cluster size distributions in a second batch of a product 1219 formulation are substantially unchanged and are stable after 2 years of their making and storage started.

Example 4: Team Sports Hydration Bioavailability Experiment

A Confidential Troy Football Team Fall 2017 Study Confirmed the Improved Bioavailability of Present Invention's Hydration Drink which was Tested by the Inventors During Very Hot, Moderate Heat, and Cool Weather Conditions Football Game Conditions.

1. For the inventors of the present invention, the Troy University Football Team of Troy, Ala. in Fall 2017 conducted a confidential series of hydration experiments during their 12 week football season.

2. A sports hydration experiment was designed by the inventors to confirm the improved bioavailability of embodiments of the present invention compared to existing sports drinks or other hydration used by football players.

Note: Troy University Football Team played about 50 players in each of their football games. About 60% of the Troy University Football Team players (N=Approx. 30 players) drank a water drink formulation embodiment of the present invention as they wished as a hydration drink. Note: Other Troy University Football Team payers (N=Approx. 20 players) drank a water formulation embodiment of the present invention when they wished to which had been added Powerade™ sports drink powder, to make a sports hydration drink.

3. For the first seven weeks of their football game season Troy football players played football games in warm-very hot weather with temperatures ranging between 76° F.-97° F.

In warm to very hot weather Opponent Football Teams had twenty-two (22) of their football players needing a medical emergency IV (intravenous fluid) treatment on the football field or later to treat significant dehydration.

Surprisingly, Troy Football Team had zero (0) of their football players needing a medical emergency IV (intravenous fluid) treatment on the football field or afterwards.

4. For the last five weeks of their football game season Troy football players played football games in cooler temperatures between 52° F.-58° F.

Even in cool weather, Opponent Football teams had seven (7) of their football players needing a medical emergency IV treatment on the football field or after the game to treat significant dehydration.

Surprisingly, Troy Football players had zero (0) football players who needed a medical emergency IV treatments to help them to rehydrate from muscle cramping or other signs of dehydration in cool weather.

5. In the last week of their football season, Troy had a Championship Football Bowl game.

The Opponent Football Team had three (3) football players who played in the Bowl Game and needed a medical emergency IV treatments on the football field or afterwards to treat significant dehydration.

Surprisingly, Troy Football Team has zero (0) football players who played in the Bowl Game needed a medical emergency IV treatment on the football field or afterwards.

SUMMARY: Over 12 week season and a Bowl game, Troy Football players were functionally sufficiently well hydrated during their football games and needed no medical emergency IV rehydration.

However, conventional available hydration drinks FAILED to adequately hydrate 31 opponent football team players who as a result suffered dehydration and needed medical emergency IV treatment to rapidly correct their dehydration.

CONCLUSION: The present invention is an surprisingly improved water bioavailability product compared to the current (prior art) hydration drinks used by College Football Teams. The present invention drinks formulation has superior bioavailability to prior art hydration drinks in use by Football players in hot and cool weather.

Example 5: More Details on Enabling the Use of Malvern Zetasizer to Make Nanometer Size Measurements of the Water Clusters Containing a Non-$H_2O$ Substance(s) Using Dynamic Light Scattering Technology There are methods to measure particle size, for example by Dynamic Light Scattering (DLS) which is a technique in physics that can be used to determine the size distribution profile of small particles in suspension or polymers in solution, as well as the size distribution profile of the size of water clusters in the UPW containing non-$H_2O$ substance(s).

In the scope of DLS, temporal fluctuations are usually analyzed by means of the intensity or photon auto-correlation function (also known as photon correlation spectroscopy or quasi-elastic light scattering). In the time domain analysis, the autocorrelation function (ACF) usually decays starting from zero delay time, and faster dynamics due to smaller particles lead to faster decorrelation of scattered intensity trace. It has been shown that the intensity ACF is the Fourier transformation of the power spectrum, and therefore the DLS measurements can be equally well performed in the spectral domain. DLS can also be used to probe the behavior of complex fluids such as concentrated polymer solutions. (Dynamic light scattering, Wikipedia, 2018).

A monochromatic light source, usually a laser, is shot through a polarizer and into a sample. The scattered light then goes through a second polarizer where it is collected by a photomultiplier and the resulting image is projected onto a screen. This is known as a speckle pattern.

All of the molecules in the solution are being hit with the light and all of the molecules diffract the light in all directions. The diffracted light from all of the molecules can either interfere constructively (light regions) or destructively (dark regions). This process is repeated at short time intervals and the resulting set of speckle patterns are analyzed by an autocorrelator that compares the intensity of light at each spot over time. The polarizers can be set up in two geometrical configurations. One is a vertical/vertical (VV) geometry, where the second polarizer allows light through that is in the same direction as the primary polarizer. In vertical/horizontal (VH) geometry the second polarizer allows light not in same direction as the incident light.

When light hits small particles, the light scatters in all directions (Rayleigh scattering) as long as the particles are small compared to the wavelength (below 250 nm). Even if the light source is a laser, and thus is monochromatic and coherent, the scattering intensity fluctuates over time. This fluctuation is due to small molecules in solutions undergoing Brownian motion, and so the distance between the scatterers in the solution is constantly changing with time. This scattered light then undergoes either constructive or destructive interference by the surrounding particles, and within this intensity fluctuation, information is contained about the time scale of movement of the scatterers. Sample preparation either by filtration or centrifugation is critical to remove dust and artifacts from the solution. At short time delays, the correlation is high because the particles do not have a chance to move to a great extent from the initial state that they were in. The two signals are thus essentially unchanged when compared after only a very short time interval. As the time delays become longer, the correlation decays exponentially, meaning that, after a long time period has elapsed, there is no correlation between the scattered intensity of the initial and final states. This exponential decay is related to the motion of the particles, specifically to the diffusion coefficient. To fit the decay (i.e., the autocorrelation function), numerical methods are used, based on calculations of assumed distributions. If the sample is monodisperse then the decay is simply a single exponential. The Siegert equation relates the second-order autocorrelation function with the first-order autocorrelation function.

A correction factor that depends on the geometry and alignment of the laser beam in the light scattering setup. It is roughly equal to the inverse of the number of speckle (see Speckle pattern) from which light is collected. A smaller focus of the laser beam yields a coarser speckle pattern, a lower number of speckle on the detector, and thus a larger second order autocorrelation.

The most important use of the autocorrelation function is its use for size determination. The dynamic information of the particles is derived from an autocorrelation of the intensity trace recorded during the experiment. The second order autocorrelation curve is generated from the intensity trace.

Dynamic light scattering provides insight into the dynamic properties of soft materials by measuring single scattering events, meaning that each detected photon has been scattered by the sample exactly once. However, the application to many systems of scientific and industrial relevance has been limited due to often-encountered multiple scattering, wherein photons are scattered multiple times by the sample before being detected. Accurate interpretation becomes exceedingly difficult for systems with non-negligible contributions from multiple scattering. Especially for larger particles and those with high refractive index contrast, this limits the technique to very low particle concentrations, and a large variety of systems are, therefore, excluded from investigations with dynamic light scattering. It is possible to suppress multiple scattering in dynamic light scattering experiments via a cross-correlation approach. The general idea is to isolate singly scattered light and suppress undesired contributions from multiple scattering in a dynamic light scattering experiment. Different implementations of cross-correlation light scattering have been developed and applied. Currently, the most widely used scheme is the so-called 3D-dynamic light scattering method. The same method can also be used to correct static light scattering data for multiple scattering contributions. Alternatively, in the limit of strong multiple scattering, a variant of dynamic light scattering called diffusing-wave spectroscopy can be applied.

Depending on the anisotropy and polydispersity of the system, a resulting plot of ($\Gamma$/q2) vs. q2 may or may not show an angular dependence. Small spherical particles will show no angular dependence, hence no anisotropy. A plot of ($\Gamma$/q2) vs. q2 will result in a horizontal line. Particles with a shape other than a sphere will show anisotropy and thus an angular dependence when plotting of ($\Gamma$/q2) vs. q2. The intercept will be in any case the Dt. Thus there is an optimum angle of detection $\theta$ for each particle size. A high quality analysis should always be performed at several scattering angles (multiangle DLS). This becomes even more important in a polydisperse sample with an unknown particle size distribution. At certain angles the scattering intensity of some particles will completely overwhelm the weak scattering signal of other particles, thus making them invisible to the data analysis at this angle. DLS instruments which only work at a fixed angle can only deliver good results for some particles. Thus the indicated precision of a DLS instrument with only one detection angle is only ever true for certain particles. (Dynamic light scattering, Wikipedia, 2018).

Dt is often used to calculate the hydrodynamic radius of a sphere through the Stokes-Einstein equation. It is important to note that the size determined by dynamic light scattering is the size of a sphere that moves in the same manner as the scatterer. So, for example, if the scatterer is a random coil polymer, the determined size is not the same as the radius of gyration determined by static light scattering. It is also useful to point out that the obtained size will include any other molecules or solvent molecules that move with the particle. So, for example, colloidal gold with a layer of surfactant will appear larger by dynamic light scattering (which includes the surfactant layer) than by transmission electron microscopy (which does not "see" the layer due to poor contrast).

In most cases, samples are polydisperse. Thus, the autocorrelation function is a sum of the exponential decays corresponding to each of the species in the population It is tempting to obtain data for g1(q; $\tau$) and attempt to invert the above to extract G($\Gamma$). Since G($\Gamma$) is proportional to the relative scattering from each species, it contains information on the distribution of sizes. However, this is known as an ill-posed problem. The methods described below (and others) have been developed to extract as much useful information as possible from an autocorrelation function.

One of the most common methods is the cumulant method, from which in addition to the sum of the exponentials above, more information can be derived about the variance of the system as follows:

where $\Gamma$ is the average decay rate and $\mu 2/\Gamma 2$ is the second order polydispersity index (or an indication of the variance). A third-order polydispersity index may also be derived but this is necessary only if the particles of the system are highly polydisperse. The z-averaged translational diffusion coefficient Dz may be derived at a single angle or at a range of angles depending on the wave vector q.

One must note that the cumulant method is valid for small r and sufficiently narrow $G(\Gamma)$. One should seldom use parameters beyond $\mu 3$, because overfitting data with many parameters in a power-series expansion will render all the parameters including F less precise. The cumulant method is far less affected by experimental noise than the methods below. CONTIN algorithm An alternative method for analyzing the autocorrelation function can be achieved through an inverse Laplace transform known as CONTIN developed by Steven Provencher. CONTIN analysis is ideal for heterodisperse, polydisperse, and multimodal systems that cannot be resolved with the cumulant method. The resolution for separating two different particle populations is approximately a factor of five or higher and the difference in relative intensities between two different populations should be less than 1:10-5.

Maximum entropy method is an analysis method that has great developmental potential. The method is also used for the quantification of sedimentation velocity data from analytical ultracentrifugation. The maximum entropy method involves a number of iterative steps to minimize the deviation of the fitted data from the experimental data and subsequently reduce the $\chi 2$ of the fitted data.

Scattering of non-spherical particles—If the particle in question is not spherical, rotational motion must be considered as well because the scattering of the light will be different depending on orientation. According to Pecora, rotational Brownian motion will affect the scattering when a particle fulfills two conditions; they must be both optically and geometrically anisotropic. Rod shaped molecules fulfill these requirements, so a rotational diffusion coefficient must be considered in addition to a translational diffusion coefficient. In its most succinct form the equation appears as Where A/B is the ratio of the two relaxation modes (translational and rotational), Mp contains information about the axis perpendicular to the central axis of the particle, and M1 contains information about the axis parallel to the central axis.

In 2007, Peter R. Lang and his team decided to use dynamic light scattering to determine the particle length and aspect ratio of short gold nanorods. They chose this method due to the fact that it does not destroy the sample and it has a relatively easy setup. Both relaxation states were observed in VV geometry and the diffusion coefficients of both motions were used to calculate the aspect ratios of the gold nanoparticles.

Applications—DLS is used to characterize size of various particles including proteins, polymers, micelles, vesicles, carbohydrates, nanoparticles, biological cells, and gels. If the system is not disperse in size, the mean effective diameter of the particles can be determined. This measurement depends on the size of the particle core, the size of surface structures, particle concentration, and the type of ions in the medium.

Since DLS essentially measures fluctuations in scattered light intensity due to diffusing particles, the diffusion coefficient of the particles can be determined. DLS software of commercial instruments typically displays the particle population at different diameters. If the system is monodisperse, there should only be one population, whereas a polydisperse system would show multiple particle populations. If there is more than one size population present in a sample then either the CONTIN analysis should be applied for photon correlation spectroscopy instruments, or the power spectrum method should be applied for Doppler shift instruments.

Stability studies can be done conveniently using DLS. Periodical DLS measurements of a sample can show whether the particles aggregate over time by seeing whether the hydrodynamic radius of the particle increases. If particles aggregate, there will be a larger population of particles with a larger radius. In some DLS machines, stability depending on temperature can be analyzed by controlling the temperature in situ.

Malvern Instruments sells the Zetasizer Nano ZSP which is a high performance system and particularly suitable for the characterization of proteins and nanoparticles where the highest sensitivity for size and zeta potential measurement is required. It includes a Protein Measurement option for protein mobility measurements. The system incorporates a two angle particle and molecular size analyzer for the enhanced detection of aggregates and measurement of small or dilute samples, and samples at very low or high concentration using dynamic light scattering with 'NIBS' optics. The ZSP also incorporates a zeta potential analyzer that uses electrophoretic light scattering for particles, molecules and surfaces, and a molecular weight analyzer using static light scattering. Using Non-Invasive Backscatter optics (NIBS) it has significantly better performance than systems using 90 degree scattering optics. In addition, a microrheology option is available for measuring sample viscosity and viscoelastic properties. The flow mode option enables the system to be connected to an SEC or an FFF system to use as a detector for the size of proteins or nanoparticles. A choice of cuvettes are available, from disposable single-use to specific cells for viscous or high concentration samples or measuring the zeta potential of surfaces.

Parameters Measured:

Particle and molecule size, translational diffusion, electrophoretic mobility, zeta potential of particles at high and low concentrations, viscosity and viscoelasticity of protein and polymer solutions, concentration, MW, $A_2$, $k_D$.

An optional accessory enables measurement of the zeta potential of solid surfaces.

Exceptional sensitivity for the zeta potential measurement of proteins and nanoparticles using patented M3-PALS.

Size measurement from 0.3 nm (diameter) to 10 microns using patented NIBS (Non-Invasive Back Scatter) technology.

Zeta potential of surfaces using accessory cell.

Molecular weight measurement down to 980 Da.

Microrheology option to measure viscosity and viscoelasticity.

Outstanding protein size measurement sensitivity, 0.1 mg/mL (Lysozyme).

Sample concentrations from 0.1 ppm to 40% w/v.

Built-in protein calculators, including protein charge, $A_2$, $k_D$, and molecular conformation.

A 'Quality Factor' and 'Expert Advice System' gives the confidence of having an expert at your shoulder.
21CFR part 11 software option to enable compliance with ER/ES.
Research software option to give access to further features and analysis algorithms for the light scattering specialist.
Automation of measurements using an autotitrator option.
Chromatography detector capability to enable use as a size detector with GPC/SEC or FFF.
Optical filter option to improve measurements with fluorescent samples.
Note that polystyrene latex standards are used to demonstrate the accuracy, reliability and reproducibility of the NanoSampler accessory for the Zetasizer Nano series of instruments. 60 nm Polystyrene LTX3060A and 200 nm beads LTX3200A standard deviations of about 0.5% in batch, autosampled, as well as aliquot to.
Automate particle size measurements for the Zetasizer Nano using the NanoSample—a versatile, compact sample management accessory that precisely and reproducible loads your samples into the Zetasizer Nano.
Automated measurements reduce operator bias and improve laboratory efficiency.
Automate sample loading, reproducibility studies and increase sample throughput.
Unattended multivariate analysis simplifies exploration of the effect of key formulation parameters.
Makes the Zetasizer Nano even easier to use and enables 24/7 operation
Simple change over from automated to manual measurement.

Example 6: Nano-Sized Particle Shape (Nanoparticle Shape) Surface Area to Volume of Nano-Sized Particles Measurements of nanoparticle dimensions allow calculations of average nanoparticle surface area (SA) and average nanoparticle volume (Vol). A SA/Vol ratio can be calculated assuming the nanoparticle has a smooth and simple geometric surface and volume. Below Tables 1-4, compare calculated values of SA, Vol, and SA/Vol for four different nanoparticle volume shapes: cube, sphere, long round rod, and flat cylinder. In these examples, the long round rod has been made six times longer than its diameter. The flat cylinder has a diameter which is six times greater than its height. In Tables 1, 2, 3, and 4, the SA, the Vol, and the SA/Vol are shown for 1, 10, 100, and 1000 nm size nanoparticles.

TABLE 1

| Nanoparticle Cube SD = side wall | Smallest Dimension ("SD") (nm) | Surface Area ('SA') ($nm^2$) $SA = 6d^2$ | Volume ('Vol') ($nm^3$) $Vol = d^3$ | SA/Vol ($nm^{-1}$) | SA/Vol change compared to a 1 micron nanoparticle |
|---|---|---|---|---|---|
| | 1 | 6 | 1 | 6.0 | 1,000 |
| | 10 | 600 | 1,000 | 0.60 | 100 |
| | 100 | 60,000 | 1,000,000 | 0.060 | 10 |
| | 1,000 | 6,000,000 | 1,000,000,000 | 0.0060 | 1 |

TABLE 2

| Nanoparticle sphere SD = diameter | Smallest Dimension ("SD") (nm) | Surface Area ('SA') ($nm^2$) $SA = 4\pi(d/2)2 = \pi d^2$ | Volume ('Vol') ($nm^3$) Volume = $(4/3)\pi(d/2)^3 = (1/6)\pi d^3$ | SA/Vol ($nm^{-1}$) | SA/Vol change compared to a 1 micron nanoparticle |
|---|---|---|---|---|---|
| | 1 | 3.14 | 0.524 | 6.0 | 1,000 |
| | 10 | 314 | 524 | 0.60 | 100 |
| | 100 | 31,400 | 524,000 | 0.060 | 10 |
| | 1000 | 3,140,000 | 524,000,000 | 0.0060 | 1 |

Note 1: Table 1 and Table 2 calculations indicate a sphere with a diameter the same as the side wall length of a cube, has about one-half the surface area and about one half the volume of the cube.

Note 2: Table 1 and Table 2 calculations show that the SA/Vol ratio of the cube and sphere both increase 1,000-fold and at the same rate as the nanoparticle diameter becomes 1,000-fold less.

TABLE 3

| Nanoparticle Rod. SD = D and Length = 6D. | Smallest Dimension ("SD") (nm) | Surface Area ('SA') (nm$^2$) SA = $2\pi(d/2)2$ + $(6d)2\pi d/2$ = $6.5\pi d^2$ | Volume ('Vol") (nm$^3$) Vol = $6d\pi(d/2)^2$ = $1.5\pi d^2$ | SA/Vol (nm$^{-1}$) | SA/Vol change compared to a 1 micron nanoparticle |
|---|---|---|---|---|---|
| | 1 | 20.4 | 4.71 | 4.3 | 1,000 |
| | 10 | 2,040 | 4,710 | 0.43 | 100 |
| | 100 | 204,000 | 4,710,000 | 0.043 | 10 |
| | 1,000 | 20,400,000 | 4,710,000,000 | 0.0043 | 1 |

TABLE 4

| Nanoparticle Disk of Thickness = D/6 ("D") (nm) | Smallest Dimension is diameter | Surface Area ('SA') (nm$^2$) SA = $2\pi(d/2)2$ + $(d/6)2\pi d/2$ = $(2/3)\pi d^2$ | Volume ('Vol") (nm$^3$) Vol = $(d/6)\pi(d/2)^2$ = $(2/3)\pi d^3$ | SA/Vol (nm$^{-1}$) | SA/Vol change compared to a 1 micron nanoparticle |
|---|---|---|---|---|---|
| | 1 | 2.09 | 2.09 | 1 | 1,000 |
| | 10 | 209 | 2090 | 0.1 | 100 |
| | 100 | 20,900 | 2,090,000 | 0.01 | 10 |
| | 1000 | 2,900,000 | 2,090,000,000 | 0.001 | 1 |

The rates and amounts of molecular events occurring at the surface of the nanoparticle are scaled as a function of the SA per nanoparticle and these events may alter an environment outside the nanoparticle as a function of the total SA of the nanoparticles dispersed in this environment. The surface of the nanoparticle with respect to its external environment creates an interface where various chemical, thermodynamic, and entropic forces interplay. Due to differences between the surface and its events in relation to external environment differences and events, the zone above the nanoparticle in which there the chemical, thermodynamic, and entropic forces need to be considered can be viewed as having a thickness. Thus the interface should not be visualized as necessarily a thin surface but as a potentially complex atmosphere surrounding a nanoparticle, particularly when the nanoparticle is contained within a biological external environment.

Figure 21:
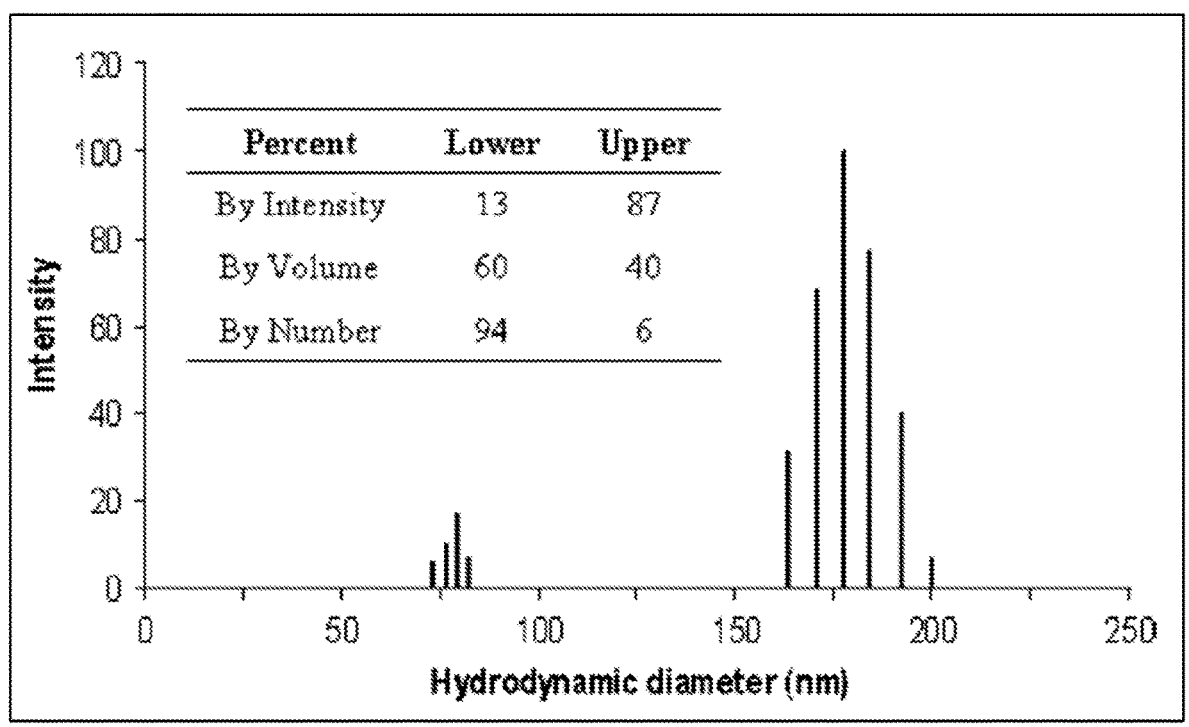
FIG. 21 presents FIG. 2 of Keresztessy et al. 2009 which shows that DLS reported a bimodal distribution for hydrodynamic diameter ranging between 70-90 and 160-200 nm with mean values of 80 and 178 nm, respectively.

Example 7—Example of Validation Method to Support Quantification of Particles and Water Clusters Size by Using Calibrated Zetasizer Dynamic Light Scattering The presence of individual nanoparticles can be confirmed and their size distribution characterized by dynamic light scattering (DLS). DLS reported a bimodal distribution for hydrodynamic diameter ranging between 70-90 and 160-200 nm with mean values of 80 and 178 nm, respectively (Keresztessy et al. 2009 FIG. 21). Calibration standards may be a considered for a quantitative proof of invention concept testing.

Example 8—Fundamental Need for Products of the Present Invention

Due to chronic dehydration the fundamental terrain of the human body experiences over time, and especially during aging of a large number of indices, signs, and measures of physiological dehydration which include: (1) dyspeptic pain, (2) stress, (3) depression, (4) high blood cholesterol, (5) high blood pressure, (6) excess body weight, (7) chronic fatigue, (8) arthritis, (9) asthma, (10) allergy, (11) insulin independent diabetes, and (12) rheumatoid arthritis.

Evidence for chronic dehydration is the rehydration response of a dehydrated person. The benefits of hydration include: (1) a healthy body weight; (2) increased metabolism, (3) increased energy levels, (4) reduced join back pain, (5) easier flushing out of body waste, (6) preventing headaches; (7) alleviating headaches, (8) better skin hydration and skin health, (9) slower aging, (10) stimulation of the primary mode of transport of all nutrients because nutrient transport needs bioavailable water due to its primary role as solute in dissolving nutrients. One factor is smaller water clusters can be a better solute in breaking down cellular debris and allow for its transfer more effectively.

Example 9: Contemplated Uses of the Present Invention Include the Following (1) Human Health Uses, (2) Modulating cellular performance, (3) Intra-cellular & extra-cellular hydration, (4) Delivery system for nutritional agents or medicine, (5) Agriculture Uses, (6) superior delivery of fertilizers/nutritional agents, (7) Superior hydration method for all forms of plant species, (8) Livestock Farming Uses, (9) Improving health and lifespan of livestock (chickens, horses), and (10) Immune enhancement of livestock

Example 10: Use of Present Invention in Improving Tissue Bio-Preservation

A growing body of evidence indicates that organ and tissue preservation is now achievable. Recent promising discoveries include organ cryopreservation and subzero cooling, perfusion, interventions before organ and tissue recovery, and adaptations that allow dozens of species in nature to enter suspended animation at subfreezing temperatures. Together, these approaches form a blueprint for a leap forward in preservation capabilities, centered on a combination of two promising strategies: (1) Providing organ 'life support' by recapitulating aspects of the organ's healthy physiological environment. (2) Effectively controlling biological time by slowing or halting metabolism to decrease the rate of deterioration. Progress on both fronts is needed because each preservation approach involves tradeoffs often requiring the application of combined strategies in the same organ or tissue. For instance, slowing organ deterioration for extended preservation periods can be achieved by lowering organ temperature and metabolic rates, but this also entails the loss of normal organ function and opportunities for beneficial interventions, such as organ assessment, repair, and functional augmentation. Thus, some embodiments of the present invention may concern protecting cadaver tissues. The aim of bio-preservation is first an environment to keep a particular organ or tissue healthy on its way to transplantation (or use in research), and a process during which the organ or tissue traverses multiple preservation conditions and temperature ranges that are used synergistically. To make an integrated approach to preservation successful, we must combine and advance a family of research areas that includes cryopreservation, programmed metabolic suppression, subzero preservation and supercooling, and perfusion and ex vivo maintenance at a variety of temperatures, ranging from hypothermia (refrigeration) to normothermia (body temperature), and donor management before organ and tissue recovery. In one embodiment the present invention concerns a biopreservation media for a hypothermic 2-8° C. biopsy sample preservation. Optionally may be included components that scavenge free radicals, provide pH buffering, oncotic/osmotic support, energy substrates, and ionic concentrations that balance the intracellular state at low temperatures. These components can reduce post-preservation necrosis and apoptosis and extend post-preservation viability.

Example 11: Use of the Present Invention as a Hydration Drink

Embodiments of the present invention can be used in the commercial beverage industry as the primary ingredient of any given trademarked bottling formula, in order to maintain critical consistency of taste, clarity, and color. Embodiments of the present invention can be used as healthy drinks and can be a good substitute to a person drinking purified water, particularly a person who is an athlete engaged in muscular work needing continual good hydration for suitable and safe functioning of their body, or a person engaged in a lot of intellectual work where their brain needs good hydration and ability to concentrate on their mental tasks.

1. Example Embodiment of a 8 Ounce Sports Drink Formulation of the Present Invention.

| | |
|---|---|
| Ultrapure Water (UPW) | 8 fluid ounces |
| Sugar | 4.1 mg |
| Vitamin C (citrate) * | 0.027 mg |
| Magnesium * | 0.068 mg |
| Chloride * | 0.23 mg |
| Sodium * | 0.0045 mg |
| Potassium * | 0.045 mg |
| Sulfate * | 0.011 mg |
| Boron + | 0.36 mcg |
| Total weight of ions * | 0.38 mg |

+ Boron is an unstable +3 cation.
In water $B(OH)_4^-$ forms.

The present Invention drink embodiments frequently include an amount of minerals from a Trace Mineral Concentrates™ (TMC™) as a convenient concentrated source of a non-H2O substance for use in Process steps 6 and 7. The ions that are present at more than a 0.5 mcg/ml concentration in the Trace Minerals Concentrate™ (TMC) are listed in the table below.

Boron, Chloride, Magnesium, Potassium, Sodium and Sulfate are the predominate ions in the TMC Concentrate used to make one embodiment of the hydration drink.

| Chemical Ion Species | Concentration Called For by Specification |
|---|---|
| Aluminum | <10 micrograms/ml |
| Boron | 0.420-0.650 milligrams/ml |
| Calcium | <165 micrograms/ml |
| Chloride | 264-350 milligrams/ml |
| Copper | not established |
| Fluoride | <100 micrograms/ml |
| Iodine | <25 micrograms/ml |
| Iron | <31 micrograms/ml |
| Magnesium | 101.5-110 milligrams/ml |
| Phosphorus | <10 micrograms/ml |
| Potassium | 1.25-2.5 milligrams/ml |
| Rubidium | <2 microgramns/ml |
| Silicon | <5 micrograms/ml |
| Sodium | <4 milligrams/ml |
| Sulfate | 16.5-35 milligrams/ml |
| Titanium | <4 micrograms/ml |
| Zinc | <3.5 micrograms/ml |
| Zirconium | <3.5 micrograms/ml |

Preferred genuses of the ions that are present at more than a 0.5 mcg/ml concentration n the Trace Minerals Concentrate™ (TMC™) include the following lists.

A Non-H2O substance may be a cation and an anion combination which maintains charge electroneutrality. For example the combination of ions can make an electrolyte solution. Such combinations of an anion(s) and a cation(s) may selected from the group consisting of an Aluminum cation, an Antimony cation, an Arsenic cation, a Barium cation, a Beryllium cation, a Bismuth cation, a Boron ion, a Bromide anion, a Cadmium cation, a Calcium cation, a Cerium cation, a Cesium cation, a Chloride anion, a Chromium cation, a Cobalt cation, a Copper cation, a Dysprosium cation, an Erbium cation, a Europium cation, a Fluoride anion, a Gadolinium cation, a Gallium cation, a Germanium cation, a Gold cation, a Hafnium cation, a Holmium cation, an Indium cation, a Iodine anion, an Iridium cation, a Iron cation, a Lanthanum cation, a Lead cation, a Lithium cation, a Lutetium cation, a Magnesium cation, a Manganese cation, a Mercury cation, a Molybdenum cation, a Neodymium cation, a Nickel cation, a Niobium cation, an Osmium cation, a Palladium cation, a Phosphorus anion, a Platinum cation, a Potassium cation, a Praseodymium cation, a Rhenium cation, a Rhodium cation, a Rubidium cation, a Ruthenium cation, a Samarium cation, a Scandium cation, a Selenium cation, a Silicon cation, a Silver cation, a Sodium cation, a Strontium cation, a Sulfate anion, a Tantalum cation, a Tellurium cation, a Terbium cation, a Thallium cation, a Thorium cation, a Thulium cation, a Tin cation, a Titanium cation, a Tungsten cation, a Vanadium cation, a Ytterbium cation, a Yttrium cation, a Zinc cation, and a Zirconium cation.

A smaller mixture of trace minerals than 1. may be useful. A non-H2O substance may be a cation and an anion combination which maintains charge electro-neutrality. For example the combination of ions can make an electrolyte solution. Such combinations of an anion(s) and a cation(s) may selected from the group consisting of an Aluminum cation, an Antimony cation, a Barium cation, a Bismuth cation, a Boron ion, a Bromide anion, a Calcium cation, a Cerium cation, a Cesium cation, a Chloride anion, a Chromium cation, a Cobalt cation, a Copper cation, a Dysprosium cation, an Erbium cation, a Europium cation, a Fluoride anion, a Gadolinium cation, a Gallium cation, a Germanium cation, a Gold cation, a Hafnium cation, a Holmium cation, an Indium cation, a Iodine anion, an Iridium cation, a Iron cation, a Lithium cation, a Lutetium cation, a Magnesium cation, a Manganese cation, a Molybdenum cation, a Neodymium cation, a Niobium cation, an Osmium cation, a Palladium cation, a Phosphorus anion, a Platinum cation, a Potassium cation, a Praseodymium cation, a Rhenium cation, a Rhodium cation, a Rubidium cation, a Ruthenium cation, a Samarium cation, a Scandium cation, a Selenium cation, a Silicon cation, a Silver cation, a Sodium cation, a Strontium cation, a Sulfate anion, a Tantalum cation, a Tellurium cation, a Terbium cation, a Thulium cation, a Tin cation, a Titanium cation, a Tungsten cation, a Vanadium cation, a Ytterbium cation, a Yttrium cation, a Zinc cation, and a Zirconium cation.

An even shorter list of minerals than 2. may be useful. A non-H2O substance may be a cation and an anion combination which maintains charge electro-neutrality. For example the combination of ions can make an electrolyte solution. Such combinations of an anion(s) and a cation(s) may selected from the group consisting of an Antimony cation, a Barium cation, a Bismuth cation, a Boron ion, a Bromide anion, a Calcium cation, a Cerium cation, a Chloride anion, a Chromium cation, a Cobalt cation, a Copper cation, a Europium cation, a Fluoride anion, a Gold cation, a Iodine anion, a Iron cation, a Lithium cation, a Magnesium cation, a Manganese cation, a Molybdenum cation, a an Osmium cation, a Palladium cation, a Phosphorus anion, a Platinum cation, a Potassium cation, a Rubidium cation, a Ruthenium cation, a Scandium cation, a Selenium cation, a Silicon cation, a Silver cation, a Sodium cation, a Strontium cation, a Sulfate anion, a Tantalum cation, a Tin cation, a Titanium cation, a Tungsten cation, a Vanadium cation, and a Zinc cation.

Example 12: Formulations are Listed Below which are Other Important Embodiments of the Present Invention for Various Uses 1. A formulation for treating a brain health need comprises: ultra pure water; Synapta (SynaptaGenX™ dietary supplement); a magnesium salt; Concentrate Trace Mineral Drops™; and sodium benzoate. To 300 gallons of ultra pure water are added the following brain health formulation ingredients: 0.001-1000 grams of Synapta™; 0.01-3000 grams of magnesium chloride; 0.08-3.8 liters of Trace Mineral Drops™; and 0.01-240 grams of sodium benzoate.

2. A formulation for treating an anxiety disorder comprises: ultra pure water; 40K Volts Electrolyte Concentrate™ (dietary supplement made by Trace Minerals, Utah); CBD; sodium bicarbonate; sodium benzoate; and Concentrace Trace Mineral Drops™. To 300 gallons ultra pure water are added 0.005-300 gms CBD; 0.001-10.8 liters Trace Mineral Drops™; 0.001-6.9 liters of 40K Volts Electrolyte Concentrate™ 40K, 1-360 grams sodium bicarbonate, and 0.01-240 grams of sodium benzoate.

3. A formulation for losing weight comprises: ultra pure water; Moringa; Medium Chain Triglycerides (MCT); Saffron; Narringin; Green select Phytosome; Forskolin; Niacin (Nicotinic acid); sodium benzoate; *Panax Ginseng*; and Curcumin. To 200-1200 gallons of ultra pure water add 12-108 grams.

Moringa—0.08-15 g/275 gallons (Note: Moringa plant is from India. Provides antioxidants and anti-inflammatory).

MCT™—1-15 g/275 gallons. (Note: C8 MCTs and Acacia Fibers known to be brain food.)

Saffron—10-200 mg/275 gallons

Narringin—10-2000 mg/275 gallons (Note: An antioxidant, blood lipid lowering and anticarcinogenic activity).

Greenselect Phytosome—230-890 mg/275 gallons. (Note: Green tea assisting in weight vloss.)

Curcumin—125-400 mg/275 gallons (Note: AntiFungal, antibacterial, antiviral, and antioxidant properties from Tumeric Extract.)

*Panax Ginseng*™—200-600 mg/275 gallons

Forskolin—100-750 mg/275 gallons (Note appetite suppressor.)

Niacin—200-580 mg/275 gallons

Sodium Benzoate—1-4 ozs/275 gallons

4. CBD Formulation—Formulation Ingredients:

Ultra Pure Water

CBD

40K Volts Electrolyte Concentrate™

Concentrace Trace Mineral Drops™

Sodium Bicarbonate

Formulation Ingredients ratio:

Ultra Pure Water—100 gallons

CBD (crystal)—1-20 g/100 gallons

40K Volts Electrolyte Concentrate™—2-8 oz/100 gallons

Trace Mineral Drops™—1-4 oz/100 Gallons

Sodium Benzoate—0.2-3 oz/100 gallons

Ultra Pure Water—275 gallons

CBD—12-30 g/275 gallons

40K Volts Electrolyte Concentrate™—10-32 oz/275 gallons

Trace Mineral Drops™-8-32 oz/275 gallons

Sodium Benzoate—4-16 oz/275 gallons

5. Hydration Formulation—Formulation Ingredients:

Ultra Pure Water

40K Volts Electrolyte Concentrate™

Concentrace Trace Mineral Drops™

Sodium Benzoate

Formulation Ingredients Ratio:

Ultra Pure Water—50 gallons

40K Volts Electrolytes™—1-4 oz/50 gallons

Trace Mineral Drops™—0.1-0.8 oz/50 gallons

Sodium Benzoate—0.01-4 oz/50 gallons

Ultra Pure Water—275 gallons

40K Volts Electrolytes™-1-9 oz/275 gallons
Trace Mineral Drops™—1-4 oz/275 gallons
Sodium Benzoate—1-5 ozs/275 gallons
6. Alkaline Electrolyte Formulation—Formulation Ingredients:
Ultra Pure Water
Concentrace Trace Mineral Drops™
Himalayan Pink Salt
40K Volts Electrolyte Concentrate™
Sodium Bicarbonate
Formulation Ingredients ratio:
Ultra Pure Water—50 gallons
Trace Mineral Drops™—0. q-0.8 oz/50 gallons
Himalayan Pink Salt—25-950 mg/50 gallons
Sodium Bicarbonate—1-12 oz/50 gallons
40K Volts Electrolyte Concentrate™-1-6 oz/50 gallons
Ultra Pure Water—275 gallons
Trace Mineral Drops™—0.3-5 oz/275 gallons
Himalayan Pink Salt—1-5 g/275 gallons
Sodium Benzoate—20-65 ozs/275 gallons
40K Volts Electrolyte Concentrate™—2-12 oz/275 gallons.
7. Dyspepsia Formulation
Formulation Ingredients:
Ultra Pure Water
Bio Nutrition Gout Out™ (Note Goutout is by BIO Nutrition a dietary supplement.)
Tart Cherry
Sodium Benzoate
Formulation Ingredients Ratio:
Ultra Pure Water—50 gallons
Bionutrition Gout Out™—1-8 caps/50 gallons
Tart Cherry—1-4 caps/50 gallons
Sodium Benzoate—0.4-4 oz/50 gallons
8. Headache Formulation
Formulation Ingredients:
Ultra Pure Water
Resveratrol™ 0.5-4 pill/50 gallons. Liver Care is in powdered form and is an herbamof 7 sun
Liver Care™
D-Ribose
40K Volts Electrolyte Concentrate™
Concentrace Trace Mineral Drops™
Sodium Benzoate
Formulation Ingredients Ratio:
Ultra Pure Water—50 gallons
Resveratrol™—25% 0.5 pill 10 mg/50 gallons is by Reseveratrol Nutritiuon, Gainsville, Fla., a dietary supplement made from 8 natural herbs
Liver Care™—0.10-0.80 mg/50 gallons
D-Ribose—0.1-0.6 mg/50 gallons
40K Electrolyte Concentrate™—1-4 oz/50 gallons
Trace Mineral Drops™—10-120 drops/50 gallons
Sodium Benzoate—0.2-1 oz/50 gallons
Ultra Pure Water—275 gallons
Resveratrol™—2 pills/275 gallons
Liver Care™—2 g/275 gallons
D-ribose—2 tablets/275 gallons
40K Electrolyte Concentrate™—4 oz/275 gallons
Trace Mineral Drops™—300 drops/275 gallons
Sodium Benzoate—2 oz/275 gallons
9. Agriculture Humic Formulation
Formulation Ingredients:
Ultra Pure Water
Fulvic Humic Liquid
Formulation Ingredients Ratio:
Ultra Pure water—275 gallons
Fulvic Humic liquid—5-25 ozs/275 gallons. Made from mineral mined natural Humic
10. Cold Remedy Formulation
Formulation Ingredients:
Ultra Pure Water
CBD
Capsaicin
Concentrace Trace Mineral Drops™
Resveratrol™
Sodium Benzoate
Formulation Ingredients Ratio:
Ultra Pure Water—50 gallons
Capsaicin—1-4 ozs/50 gallons (Note Capsaicin is Cayenne Pepper)
CBD—0.1-2 g/50 gallons
Trace Mineral Drops™—0.2-0.6 oz/50 gallons
Resveratrol™—0.1-2 mg/50 gallons
Sodium Benzoate—0.1-5 oz
/50 gallons
Ultra Pure Water—275 gallons
Capsaicin—1-20 oz/275 gallons
CBD—1-10 g/275 gallons
Trace Mineral Drops™-1-4 oz/275 gallons
Resveratrol™—1-10 mg/275 gallons
Sodium Benzoate—2-5 oz/275 gallons
11. An Elder Care Formulation
Formulation Ingredients:
Ultra Pure Water
Multi 5 Collagen™
Silicon/Choline™ ch—OSA)
Nicotinamide Riboside
Trans—Resveratrol™
B Vitamin Complex
Vitamin C
Sodium Benzoate
Formulation Ingredients Ratio:
Ultra Pure Water—50 gallons
Multi 5 Collagen™—0.5-4 g/50 gallons (Note: Five types of protein in powder form. MultiCollage Protein™ by Axe Products.
Silicon/Choline™—2-12 drops/50 gallons
Nicotinamide Riboside—0.25-1.25 tabs/50 gallons (Note FDA Ingredient Naigin)
Trans-Resveratrol™—0.1-1 cap/50 gallons
B Vitamin Complex—0.5-3 cap/50 gallons
Vitamin C—1-4 g/50 gallons
Sodium Benzoate—1-12 ozs/50 gallons
Ultra Pure Water—275 gallons
Multi 5 Collagen™—6-9 g/275 gallons
Silicon/Choline™—10-30 drops/275 gallons
Nicotinamide—1-5 tabs/275 gallons
Trans-Resveratrol™—0.5-3 caps/275 gallons
B Vitamin Complex—1-3 caps/275 gallons
Vitamin C—4-8 g/275 gallons
Sodium Benzoate—1-4 ozs/275 gallons
12. Diabetic Binge formulation
Ultra Pure Water
Berberine HCL™ (Note: Glucose booster by Health Direction.com)
Zychrome™—(Note: Optimized Chromium by Quality Supplements and Vitamins)
Gymnema Sylvestre™ (Organix Glucose Gymnema Elite by Nutrusta).
R-ALA—Alpha Lipoic Acid (R-Alpha Lipoic Acid (R-ALA) helps lower blood glucose)
Cinnamon

*Panax Ginseng*™ (Fermented Korean *Panax Ginseng*—Testosterone Booster).
Magnesium
Fenugreek™ (note: Testosterone booster by Barlowe's).
Ultra Pure Water—50 gallons
Berberine HCL™—200-700 mg/50 gallons
Zychrome™—10-150 mcg/50 gallons
Gymnema Sylvestre™—12-140 mg/50 gallons
ALA—2-30 mg/50 gallons
Cinnamon—0.1-4.0 g/50 gallons
*Panax Ginseng*™—10-110 mg/50 gallons
Magnesium—10-200 mg/50 gallons
Fenugreek™—3-400 mg/50 gallons
Ultra Pure Water—275 gallons
Berberine HCL™—1000-3000 mg/275 gallons
Zychrome™—100-700 mcg/275 gallons
Gymnema Sylvestre™—300-600 mg/275 gallons
ALA—90-180 mg/275 gallons
Cinnamon—1.5-6 g/275 gallons
*Panax Ginseng*™—250-750 mg/275 gallons
Magnesium 100-550 mg/275 gallons
Fenugreek™—120-2000 mg/275 gallons 13. Reflex Neurology Formulation
Formulation Ingredients:
Ultra Pure Water
R-ALA (Alpha Lipoic Acid)
B-Complex
Acetyl-L-Carnitine
GLA (Gamma Linolenic Acid)
Chromium
Curcumin
Vitamin C
Vitamin E
Vitamin K2 & D3
Magnesium
Corydalis
Cayenne
L-Arginine
Feverfew™ *Tanacetum Parthenium*)
Sodium Benzoate
Formulation Ingredients Ratio:
Ultra Pure Water—50 gallons
R-ALA—1/10-1/2 capsule/50 gallons
Acetyl-L-Carnitine—50-280 mg/50 gallons
GLA—50-400 mg/50 gallons
Chromium—25-125 mcg/50 gallons
Curcumin 20-160 mg/50 gallons AntiFungal, antibacterial, antiviral, and antioxidant properties from Tumeric Extract.)
Vitamin C—200-2000 mg/50 gallons
Vitamin K-2 & D-3—25-100 mcg/50 gallons
Magnesium—20-120 mg/50 gallons
Corydalis—125-375 mg/50 gallons
Cayenne—10-150 mg/50 gallons
L-Arginine—60-1000 mg/50 gallons
Feverfew™—10-120 mg/50 gallons (Herbal Supplement containing parthenolide for migraine relief, anxiety and stress, Lower inflammation, Pain Reduction).
Sodium Benzoate—0.1-2.0 ozs
Ultra Pure Water—275 gallons
R-ALA—0.5-3 capsule/275 gallons
B—Complex—1-5 capsules/275 gallons
Acetyl-L-Carnitine—100-350 mg/275 gallons
GLA—15-2000 mg/275 gallons
Chromium—300-500 mg/275 gallons
Curcumin—50-500 mg/275 gallons
Vitamin C—40-450 mg/275 gallons
Vitamin E—100-300 mg/275 gallons
Vitamin K2 & D3—0.2-0.6 mcg (1 capsule)/275 gallons
Magnesium—0.20-140 mg/275 gallons
Corydalis—50-150 mg/275 gallons
Cayenne—50-250 mg/275 gallons
L-Arginine—250-5000 mg/275 gallons
Feverfew™—35-450 mg (1 capsule)/275 gallons
Sodium Benzoate—0.5-5 ozs/275 gallons 14. ED Formulation
Formulation Ingredients:
Ultra Pure Water
L-arginine
Horny Goat Weed
Mondia Whitei
Long Jack™ (Note: 200 mg/50 gallons Libido, and stamina booster from natural herbs)
*Panax Ginseng*
Yohimbine (From Libido Health is a common plank alkaloid.
Tribulus Terrestrius (Note: Fruit-producing Me3ditterean plant that assists n prostrate health.)
Tadalafil
Sodium Benzoate
Formulation Ingredients Ratio:
Ultra Pure Water—50 gallons
L-Arginine—5.5-25 g/50 gallons
Horny Goat Weed—1.5-7 g/50 gallons
Mondia Whitei—10-450 mg/50 gallons
Long Jack™—2-300 mg/50 gallons
*Panax Ginseng* ™—10-345 mg/50 gallons
Yohimbine—0.1-10 mg/50 gallons
Tribulus Terrestrius—10-140 mg/50 gallons
Tadalafil—5-40 mg/50 gallons
Sodium Benzoate—0.3-0.9 ozs/50 gallons
Ultra Pure Water—275 gallons
L-Arginine—4-7 g/275 gallons
Horny Goat Weed—2-5 g/275 gallons
Mondia Whitei—350-700 mg/275 gallons
Long Jack™—60-1200 mg/275 gallons
*Panax Ginseng*™—300-800 mg/275 gallons
Yohimbine—0.2-12 mg/140-210 gallons
Tribulus Terrestrius—900-1100 mg/275 gallons
Tadalafil—15-50 mg/275 gallons
Sodium Benzoate—1.5-3 Ozs/275 gallons 15. CNS Wellness Formulation
Formulation Ingredients:
Ultra Pure Water
Caffeine
Theanine
B 6 Complex
*Ginkgo Biloba*
Curcumin
Huperzine A™
Cognizine Citicoline™
40K Volts Electrolyte Concentrate™
Concentrace Trace Mineral Drops™
Medium Chain Triglyceride Oil Powder
Nicotinomide Riboside
*Rhodiola*
Ketone Esters
Resveratrol™
Sodium Benzoate
Formulations Ingredients ratio:
Ultra Pure Water—100 gallons
Caffeine—0:25-6 mg/100 gallons Theanine—0.125-400 mg/100 gallons (Note: Stress reduces and relaxer, reduces elevated blood pressure and improves heart rate).
B 6 Complex—0.250-0.500 mg/50 gallons
*Ginkgo Biloba*—0 10-30 mg/50 gallons
Curcumin—0.625 mg/50 gallons
Huperzine A™—150-175 mg/50 gallons (Note: Whole herb assisting in memory and focus.)
Cognizine Citicoline™—0.07-0.9 mg/50 gallons
40K Volts Electrolyte Concentrate™—1-5 ozs/50 gallons
Trace Mineral Drops™—0.2-0.8 ozs/50 gallons
MCT Oil Powder™—2-4 g/50 gallons (C8 MCT and Acacia fibers known to be brain food.)
Nicotinomide Riboside—100-200 mg/50 gallons
*Rhodiola*—0.0.3-0.6 ml (two full drop)/50 gallons. Note: Extract from roots that assists in memory and reduces stress.)
Ketone Esters—4.7 g/50 gallons. (Note: Ketone salts that includes calcium and potassium for energy boosting.)
Resveratrol™—0.12-36 mg/50 gallons. (Note: Reseratrol is by Reseveratrol Nutrition, Gainsville, Fla., a dietary supplement made from grapes.)
Sodium Benzoate—0.0.9 ozs/50 gallons
Ultra Pure Water—200 gallons
Theanine—0.6 mg/200 gallons
B 6 Complex—200 gallons
*Ginkgo Biloba*—0.4-0.8 mg/200 gallons
Curcumin—1500 mg/200 gallons
Huperzine A—0.94 mg/200 gallons
Cognizine Citicoline™—0.438 mg/200 gallons
40K Volts Electrolyte Concentrate™—16 ozs/200 gallons
Trace Mineral Drops™—3 ozs/3600 s
MCT Oil Powder—14.0 gallons
Nicotinomide Riboside 250-1250 mg/275 gallons
*Rhodiola*—3.6-4.8 ml (7-11 full drops)/275 gallons
Ketone Esters—2-0.2 g/275 gallons
Resveratrol™—0.80-290 mg/275 gallons
Sodium Benzoate—0.5-3.8 ozs/275 gallons Example 13: Additional Uses Embodiments of the Present Invention 1. Purified water and embodiments of the present invention can be used in the pharmaceutical industry. Water of this grade is widely used as a raw material, ingredient, and solvent in the processing, formulation, and manufacture of pharmaceutical products, active pharmaceutical ingredients (APIs) and intermediates, compendia articles, and analytical reagents. The microbiological content of the water is of importance and the water must be regularly monitored and tested to show that it remains within microbiological control. Embodiments of the present invention are useful source of water for a pharmaceutical use, manufacturing of pharmaceutical products, medical devices, biologics, cell- and tissue-based products, and many other medical products. The two major categories are bulk water (i.e., produced on-site where used from an internal water system) and packaged water (i.e., produced elsewhere, packaged, sterilized to preserve microbial quality throughout the packaged shelf life, and purchased). Regardless of whether its bulk water or packaged water, the type of water is then determined by the testing performed, as defined by United States Pharmacopeia (USP) <1231> Namely—USP <1231> Water for Pharmaceutical Purposes. (Rockville, Md., Mar. 8, 2017. There are a number of pharmaceutical water types. (a) Purified water is most commonly used as a diluent in the production of non-sterile products for injection, infusion or implantation, cleaning equipment, and cleaning non-sterile product-contact components. Purified water systems must be validated to consistently produce and distribute water of acceptable chemical and microbiological quality. However, they may be susceptible to biofilms, undesirable levels of viable microorganisms, or endotoxins, which means frequent sanitization and monitoring to ensure appropriate quality at the points of use. (b) Water for injection (WFI) is most often used as an excipient in the production of sterile products and other preparations when endotoxin content must be controlled. Examples are pharmaceutical applications such as cleaning of certain equipment and sterile product-contact components. WFI must meet all the same chemical requirements of purified water with added bacterial endotoxin specifications, because endotoxins are produced by microorganisms that are prone to inhabit water. As with a water system producing purified water, WFI systems also must be validated to reliably and consistently produce and distribute water of acceptable chemical and microbiological quality. (c) Pure steam is intended for use in steam-sterilizing porous loads and equipment and in other processes, such as cleaning, where condensate would directly contact official articles, containers for these articles, process surfaces that would in turn contact these articles, or materials which are used in analyzing such articles. Pure steam is prepared from suitably pretreated source water, analogous to the pretreatment used for purified water or WFI, vaporized with a suitable mist elimination, and distributed under pressure. (d). Water for hemodialysis is specifically for hemodialysis applications and primarily for the dilution of hemodialysis concentrate solutions. Water for hemodialysis is typically produced and used on site as bulk water. This water contains no added antimicrobials and is not intended for injection.

(e). Sterile purified water is packaged and rendered sterile. It is used for preparation of sterile products or in analytical applications requiring purified water when access to a validated system is not practical and only a small quantity is needed. It is also used when bulk packaged purified water is not suitably microbiologically controlled. (f.) Sterile water for injection is packaged and rendered sterile. This water is for the processing of sterile products intended to be used intravenously. Additionally, it is used for other applications where bulk WFI or purified water is indicated but access to a validated water system is either not practical or only a relatively small quantity is needed. Sterile WFI is typically packaged in single-dose containers that are typically less than 1 L in size. (g). Sterile water for irrigation is packaged and rendered sterile. This water is commonly used when sterile water is required, but when the application does not have particulate matter specifications. Sterile water for irrigation is often packaged in containers that are typically greater than 1 L in size. (h). Sterile water for inhalation is packaged and rendered sterile. This water is usually intended for use with inhalators and in preparation of inhalation solutions. It carries a less stringent specification for bacterial endotoxins than sterile WFI and, therefore, is not suitable for parenteral applications.

(i). Bacteriostatic water for injection is a sterile water for injection to which one or more suitable antimicrobial preservatives have been added. This water is typically intended for use as a diluent in the preparation of sterile products, mostly for multi-dose products that require repeated content withdrawals, such as liquid pharmaceuticals. It may be packaged in single-dose or multiple-dose containers, usually less than 30 mL. With nine different types of water, each with specific testing requirements and applications, it is crucial to understand how they can impact products. In summary, embodiments of the present invention can be used for a pharmaceutical grade water use may be selected from the group consisting of a purified water, water for injection (WFI), pure steam, a water for hemodialysis, an intravenous water, an enema water, an eye wash, an eye drop, a nose drop, an ear drop, a sterile water for injection, a sterile water for inhalation including a ventilator delivering an aerosol to the nasal cavity or pulmonary airway, a sterile water for irrigation of a body cavity, a bacteriostatic water for injection, and a combination thereof.

5. Embodiments of the present invention can be used in a laboratory uses. Technical standards on water quality have been established by a number of professional organizations, including the American Chemical Society (ACS), ASTM International, the U.S. National Committee for Clinical Laboratory Standards (NCCLS) which is now CLSI, and the U.S. Pharmacopeia (USP). The ASTM, NCCLS, and ISO 3696 or the International Organization for Standardization classify purified water into Grade 1-3 or Types I-IV depending on the level of purity. These organizations have similar, although not identical, parameters for highly purified water. Note that the European Pharmacopeia uses Highly Purified Water (HPW) as a definition for water meeting the quality of Water For Injection, without however having undergone distillation. In the laboratory context, highly purified water is used to denominate various qualities of water having been "highly" purified. Regardless of which organization's water quality norm is used, even Type I water may require further purification depending on the specific laboratory application. For example, water that is being used for molecular-biology experiments needs to be DNase or RNase-free, which requires special additional treatment or functional testing. Water for microbiology experiments needs to be completely sterile, which is usually accomplished by autoclaving. Water used to analyze trace metals may require the elimination of trace metals to a standard beyond that of the Type I water norm. IN some cases, an embodiment of the present invention could be used in lab work and biological experiments. Electrical conductivity—The electrical conductivity of ultra-pure water is $5.5 \times 10-6$ S/m (18 MΩ·cm in the reciprocal terms of electrical resistivity) and is due only to H+ and OH− ions produced in the water dissociation equilibrium. This low conductivity is only achieved, however, in the presence of dissolved monatomic gases. Completely de-gassed ultrapure water has a conductivity of $1.2 \times 10-4$ S/m, whereas on equilibration to the atmosphere it is $7.5 \times 10-5$ S/m due to dissolved $CO_2$ in it. The highest grades of ultrapure water should not be stored in glass or plastic containers because these container materials leach (release) contaminants at very low concentrations. Storage vessels made of silica are used for less-demanding applications and vessels of ultrapure tin are used for the highest-purity applications. It is worth noting that, although electrical conductivity only indicates the presence of ions, the majority of common contaminants found naturally in water ionize to some degree. This ionization is a good measure of the efficacy of a filtration system, and more expensive systems incorporate conductivity-based alarms to indicate when filters should be refreshed or replaced. For comparison,[12] sea water has a conductivity of perhaps 5 S/m (53 mS/cm is quoted), while normal un-purified tap water may have conductivity of 5 mS/m (50 μS/cm) (to within an order of magnitude), which is still about 2 or 3 orders of magnitude higher than the output from a well-functioning demineralizing or distillation mechanism, so low levels of contamination or declining performance are easily detected. [citation needed]

6. Embodiments of the present invention may be used as an "ingredient" in many cosmetics and pharmaceuticals, where it is sometimes referred to as "aqua" on product ingredient labels; see International Nomenclature of Cosmetic Ingredients. When used as a rinse after washing cars, windows, and similar applications, some embodiments of the present invention dry without leaving spots caused by dissolved solutes; embodiments of the present invention may be used in humidors to prevent cigars from collecting bacteria, mold, and contaminants, as well as to prevent residue from forming on the humidifier material. Embodiments of the present invention may be used by window cleaners using water-fed pole systems also use purified water because it enables the windows to dry by themselves leaving no stains or smears.

7. Some embodiments of the present invention are useful water sources for drinking or for use as a water supply for an animal, including an insect, invertebrates, shell fish, lobsters, crabs, oysters, fish, amphia, reptiles, birds, mammals including a human. Some embodiments of the present invention are useful water sources for growing plants, germinating seeds, and in various cell culture aqueous media and gels/agars. Some embodiments of the present invention are useful for soaking vegetables, and washing food, 8. The drinking of purified water as a replacement of drinking water has been both advocated and discouraged for health reasons. Purified water lacks minerals and ions such as calcium that play key roles in biological functions, such as in nervous system homeostasis, and are normally found in potable water. The lack of naturally occurring minerals in distilled water has raised some concerns. The Journal of General Internal Medicine published a study on the mineral contents of different waters available in the US. The study found that "drinking water sources available to North Americans may contain high levels of calcium, magnesium, and sodium and may provide clinically important portions of the recommended dietary intake of these minerals". It encouraged people to "check the mineral content of their drinking water, whether tap or bottled, and choose water most appropriate for their needs". Since distilled water is devoid of minerals, supplemental mineral intake through diet is needed to maintain proper health. The consumption of "hard" water (water with minerals) is associated with beneficial cardiovascular effects. As noted in the American Journal of Epidemiology, the consumption of hard drinking water is negatively correlated with atherosclerotic heart disease.

9. Ultra Pure Water (UPW)

According to Wikipedia (2018), Ultrapure water (also UPW or high-purity water) is water that has been purified to uncommonly stringent specifications. Ultrapure water is a commonly used term in the semiconductor industry to emphasize the fact that the water is treated to the highest levels of purity for all contaminant types, including: organic and inorganic compounds; dissolved and particulate matter; volatile and non-volatile, reactive and inert; hydrophilic and hydrophobic; and dissolved gases. UPW and commonly used term deionized (DI) water are not the same. In addition to the fact that UPW has organic particles and dissolved gases removed, a typical UPW system has three stages: a pretreatment stage to produce purified water, a primary stage to further purify the water, and a polishing stage, the most expensive part of the treatment process. A number of organizations and groups develop and publish standards associated with the production of UPW. Pharmaceutical plants follow water quality standards as developed by pharmacopeias, of which three examples are the United States Pharmacopeia, European Pharmacopeia, and Japanese Pharmacopeia. The most widely used requirements for UPW quality are documented by ASTM D5127 "Standard Guide for Ultra-Pure Water Used in the Electronics and Semiconductor Industries" and SEMI F63 "Guide for ultrapure water used in semiconductor processing". Bacteria, particles, organic and inorganic sources of contamination vary depending on a number of factors including the feed water to make UPW as well as the selection of the piping materials to convey it. Bacteria are typically reported in colony-forming units (CFU) per volume of UPW. Particles use number per volume of UPW. Total organic carbon (TOC), metallic contaminants, and anionic contaminants are measured in dimensionless terms of parts per notation, such as ppm, ppb, ppt and ppq. Bacteria have been referred to as one of the most obstinate in this list to control. Techniques that help in minimizing bacterial colony growth within UPW streams include occasional chemical or steam sanitization (which is common in the pharmaceutical industry), ultrafiltration (found in some pharmaceutical, but mostly semiconductor industries), ozonation and optimization of piping system designs that promote the use of Reynolds Number criteria for minimum flow along with minimization of dead legs. In modern advanced UPW systems positive (higher than zero) bacteria counts are typically observed in the newly constructed facilities. This issue is effectively addressed by sanitization using ozone or hydrogen peroxide. With proper design of the polishing and distribution system no positive bacteria counts are typically detected throughout the life cycle of the UPW system. Particles can be controlled by use of filtration and ultrafiltration. Sources can include bacterial fragments, the sloughing of the component walls within the conduit's wetted stream and also the cleanliness of the jointing processes used to build the piping system.

Total organic carbon (TOC) in ultrapure water can contribute to bacterial proliferation by providing nutrients, can substitute as a carbide for another chemical species in a sensitive thermal process, react in unwanted ways with biochemical reactions in bioprocessing and, in severe cases, leave unwanted residues on production parts. TOC can come from the feed water used to produce UPW, from the components used to convey the UPW (additives in the manufacturing piping products or extrusion aides and mold release agents), from subsequent manufacturing and cleaning operations of piping systems or from dirty pipes, fittings and valves.

Metallic and anionic contamination in UPW systems can shut down enzymatic processes in bioprocessing, Depending on the level of purity needed, detection of these contaminants can range from simple conductivity (electrolytic) readings to sophisticated instrumentation such as ion chromatography (IC), atomic absorption spectroscopy (AA) and inductively coupled plasma mass spectrometry (ICP-MS).

10. Applications—The polishing stage is a set of treatment steps and is usually a recirculation and distribution system, continuously treating and recirculating the purified water in order to maintain stable high purity quality of supplied water. Traditionally the resistivity of water serves as an indication of the level of purity of UPW. Deionized (DI) water may have a purity of at least one million ohms-centimeter or one Mohm·cm. Typical UPW quality is at the theoretical maximum of water resistivity (18.18 Mohm·cm at 25° C.). Therefore the term has acquired measurable standards that further define both advancing needs and advancing technology in ultrapure water production. If in-line conductivity exceeds values additional testing is required before a conclusion can be made. Refer to the respective pharmacopoeia for details.

Ultrapure water is treated through multiple steps to meet the quality standards for different users. The "ultrapure water" term became more popular in the later 1970s and early 1980s as a way of describing the particular quality of water used in power, pharmaceutical, or semiconductor facilities. While each industry uses what it calls "ultrapure water", the quality standards vary, meaning that the UPW used by a pharmaceutical plant is different than that used in a semiconductor fab or a power station. The standards tie into the UPW use. For instance, semiconductor plants use UPW as a cleaning agent, so it is important that the water not contain dissolved contaminants that can precipitate or particles that may lodge on circuits and cause microchip failures. The power industry uses UPW as a source to make steam to drive steam turbines; pharmaceutical facilities will use UPW as a cleaning agent, as well as an ingredient in products, so they seek water free of endotoxins, microbials, and viruses.

11. Ion exchange (IX) and electrodeionization (EDI) are the primary deionization technologies associated with UPW production, in most cases following reverse osmosis (RO). Depending on the required water quality, UPW treatment plants often also feature degasification, microfiltration, ultrafiltration, ultraviolet irradiation, and measurement instruments (e.g., total organic carbon [TOC], resistivity/conductivity, particles, pH, and specialty measurements for specific ions). In pure water systems, electrolytic conductivity or resistivity measurement is the most common indicator of ionic contamination. The same basic measurement is read out in either conductivity units of microsiemens per centimeter ($\mu$S/cm), typical of the pharmaceutical and power industries or in resistivity units of megohm-centimeters (Mohm·cm) used in the microelectronics industries. These units are reciprocals of each other. Absolutely pure water has a conductivity of 0.05501 $\mu$S/cm and a resistivity of 18.18 Mohm·cm at 25° C., the most common reference temperature to which these measurements are compensated. An example of the sensitivity to contamination of these measurements is that 0.1 ppb of sodium chloride raises the conductivity of pure water to 0.05523 $\mu$S/cm and lowers the resistivity to 18.11 Mohm·cm.

Ultrapure water is easily contaminated by traces of carbon dioxide from the atmosphere passing through tiny leaks or diffusing through thin wall polymer tubing when sample lines are used for measurement. Carbon dioxide forms conductive carbonic acid in water. For this reason, conductivity probes are most often permanently inserted directly into the main ultrapure water system piping to provide real-time continuous monitoring of contamination. These probes contain both conductivity and temperature sensors to enable accurate compensation for the very large temperature influence on the conductivity of pure waters. Conductivity probes have an operating life of many years in pure water systems. They require no maintenance except for periodic verification of measurement accuracy, typically annually. Sodium is usually the first ion to break through a depleted cation exchanger. Sodium measurement can quickly detect this condition and is widely used as the indicator for cation exchange regeneration. The conductivity of cation exchange effluent is always quite high due to the presence of anions and hydrogen ion and therefore conductivity measurement is not useful for this purpose. Sodium is also measured in power plant water and steam samples because it is a common corrosive contaminant and can be detected at very low concentrations in the presence of higher amounts of ammonia and/or amine treatment which have a relatively high background conductivity. On-line sodium measurement in ultrapure water most commonly uses a glass membrane sodium ion-selective electrode and a reference electrode in an analyzer measuring a small continuously flowing sidestream sample. The voltage measured between the electrodes is proportional to the logarithm of the sodium ion activity or concentration, according to the Nernst equation. Because of the logarithmic response, low concentrations in sub-parts per billion ranges can be measured routinely. To prevent interference from hydrogen ion, the sample pH is raised by the continuous addition of a pure amine before measurement.

Calibration at Low Concentrations is Often Done

Non-volatile residue—Another type of contamination in UPW is dissolved inorganic material, primarily silica. Silica is one of the most abundant mineral on the planet and is found in all water supplies. TOC—Total organic carbon is most commonly measured by oxidizing the organics in the water to $CO_2$, measuring the increase in the $CO_2$ concentration after the oxidation Oxidation of organics to $CO_2$ is most commonly achieved in liquid solutions by the creation of the highly oxidizing chemical species, the hydroxyl radical (OH.). For the typical TOC levels in UPW systems most methods utilize hydroxyl radicals in the liquid phase. There are multiple methods to create sufficient concentrations of hydroxyl radicals needed to completely oxidize the organics in water to $CO_2$, each method being appropriate for different water purity levels. For typical raw waters feeding into the front end of an UPW purification system the raw water can contain TOC levels between 0.7 mg/L to 15 mg/L and require a robust oxidation method that can insure there is enough oxygen available to completely convert all the carbon atoms in the organic molecules into CO2. Robust oxidation methods that supply sufficient oxygen include the following methods; Ultraviolet light (UV) & persulfate, heated persulfate, combustion, and super critical oxidation. Typical equations showing persulfate generation of hydroxyl radicals follows.

$$S_2O_8^{-2}+h\nu(254\ nm)\rightarrow 2SO_2^{-1}.\ \text{and}\ SO_2^{-1}.+H_2O\rightarrow HSO_4^{-1}+OH.$$

When the organic concentration is less than 1 mg/L as TOC and the water is saturated with oxygen UV light is sufficient to oxidize the organics to $CO_2$, this is a simpler oxidation method. The wavelength of the UV light for the lower TOC waters must be less than 200 nm and is typically 184 nm generated by a low pressure Hg vapor lamp. The 184 nm UV light is energetic enough to break the water molecule into OH and H radicals. The hydrogen radicals quickly react to create $H_2$. The equations follow: $H_2O+h\nu$ (185 nm)$\rightarrow$OH.+H. and H.+H.$\rightarrow H_2$ 12. UPW Purification process (Wikipedia, 2018) involves the following processes. Typically city feed water (containing all the unwanted contaminants previously mentioned) is taken through a series of purification steps that, depending on the quality of UPW wanted, includes gross filtration for large particulates, carbon filtration, water softening, reverse osmosis, exposure to ultraviolet (UV) light for TOC and/or bacterial static control, polishing using either ion exchange resins or electrodeionization (EDI) and finally filtration or ultrafiltration.

Some systems use direct return, reverse return or serpentine loops that return the water to a storage area, providing continuous re-circulation, while others are single-use systems that run from point of UPW production to point of use. The constant re-circulation action in the former continuously polishes the water with every pass. The latter can be prone to contamination build up if it is left stagnant with no use. For modern UPW systems it is important to consider specific site and process requirements such as environmental constraints (e.g., wastewater discharge limits) and reclaim opportunities (e.g., is there a mandated minimum amount of reclaim required). UPW systems consist of three subsystems: pretreatment, primary, and polishing. Most systems are similar in design but may vary in the pretreatment section depending on the nature of the source water Pretreatment: Pretreatment produces purified water. Typical pretreatments employed are two pass Reverse Osmosis, Demineralization plus Reverse Osmosis or HERO (High Efficiency Reverse Osmosis). In addition, the degree of filtration upstream of these processes will be dictated by the level of suspended solids, turbidity and organics present in the source water. The common types of filtration are multimedia, automatic back washable filters and ultrafiltration for suspended solids removal and turbidity reduction and Activated Carbon for the reduction of organics. The Activated Carbon may also be used for removal of chlorine upstream of the Reverse Osmosis of Demineralization steps. If Activated Carbon is not employed then sodium bisulfite is used to de-chlorinate the feed water. Primary: Primary treatment consists of ultraviolet light (UV) for organic reduction, EDI and or mixed bed ion exchange for demineralization. The mixed beds may be non-regenerable (following EDI), in-situ or externally regenerated. The last step in this section may be dissolved oxygen removal utilizing the membrane degasification process or vacuum degasification.

Polishing: Polishing consists of UV, Heat exchange to control constant temperature in the UPW supply, non-regenerable ion exchange, membrane degasification (to polish to final UPW requirements) and ultrafiltration to achieve the required particle level. Some semiconductor Fabs require hot UPW for some of their processes. In this instance polished UPW is heated in the range of 70 to 80 C before being delivered to manufacturing. Most of these systems include heat recovery wherein the excess hot UPW returned from manufacturing goes to a heat recovery unit before being returned to the UPW feed tank to conserve on the use of heating water or the need to cool the hot UPW return flow.[39]

Stainless steel remains a piping material of choice for the pharmaceutical industry. Due to its metallic contribution, most steel was removed from microelectronics UPW systems in the 1980s and replaced with high performance polymers of polyvinylidene fluoride (PVDF),[1] perfluoroalkoxy (PFA), ethylene chlorotrifluoroethylene (ECTFE) and polytetrafluoroethylene (PTFE) in the US and Europe. In Asia, polyvinyl chloride (PVC), chlorinated polyvinyl chloride (CPVC) and polypropylene (PP) are popular, along with the high performance polymers.

The polishing stage is a set of treatment steps and is usually a recirculation and distribution system, continuously treating and recirculating the purified water in order to maintain stable high purity quality of supplied water. Traditionally the resistivity of water serves as an indication of the level of purity of UPW. Deionized (DI) water may have a purity of at least one million ohms-centimeter or one Mohm·cm. Typical UPW quality is at the theoretical maximum of water resistivity (18.18 Mohm·cm at 25° C.).

Certain terminology may be used in the following description for convenience only and is not limiting. The words "lower" and "upper" and "top" and "bottom" designate directions in the drawings to which reference is made. The terminology includes the words above specifically mentioned, derivatives thereof and words of similar import. Where a term is provided in the singular, the inventors also contemplate aspects of the invention described by the plural of that term. As used in this specification and in the appended claims, the singular forms "a", "an" and "the" include plural references unless the context clearly dictates otherwise, e.g., "a tip" includes a plurality of tips. Thus, for example, a reference to "a method" includes one or more methods, and/or steps of the type described herein and/or which will become apparent to those persons skilled in the art upon reading this disclosure. Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods, constructs and materials are now described. All publications mentioned herein are incorporated herein by reference in their entirety. Where there are discrepancies in terms and definitions used in references that are incorporated by reference, the terms used in this application shall have the definitions given herein. It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

What is claimed:

1. A method for producing ultrapure water that generates increased cellular permeation comprising:
    pumping a first solution of ultrapure water through a transfer pipe and a nozzle into a hollow cylinder,
    wherein the nozzle is located at the proximal end of the hollow cylinder and comprises:
        (i) an intake hole in a proximal face of the nozzle connected to the transfer pipe; and
        (ii) jet openings in a distal face of the nozzle that open into a chamber defined by the hollow cylinder, wherein the jet openings are radially arranged around the nozzle in a plane that is orthogonal to the long axis of the hollow cylinder, wherein the jet openings expel the ultrapure water toward an inner surface of the hollow cylinder and wherein the jet openings are configured to create a vortex of ultrapure water in contact with the inner surface of the chamber to produce a second solution of ultrapure water; and
    wherein the second solution of ultrapure water generates increased cellular permeation as compared to a first solution of ultrapure water.

2. The method of claim 1, wherein the first solution is pumped through the transfer pipe at a flow rate between about 10 to about 25 gallons per minute.

3. The method of claim 2, wherein the flow rate is between about 12 to about 18 gallons per minute.

4. The method of claim 2, wherein the width of the chamber is between about 1 to about 20 inches, the length of the chamber is between about 1 to about 80 inches, and the flow rate is equal to or greater than about 14 gallons per minute.

5. The method of claim 2, wherein the width of the chamber is about 4 inches, the length of the chamber is about 18 inches, and the flow rate is about 14 gallons per minute.

6. The method of claim 1, wherein the first solution is pumped through the transfer pipe under a pressure of between about 10 to about 70 pounds per square inch.

7. The method of claim 1, wherein the first solution is pumped through the transfer pipe under a pressure of between about 25 to about 40 pounds per square inch.

8. The method of claim 1, wherein the resistivity of the first solution of ultrapure water is between about 17 to about 18.2 meg-ohm cm.

9. The method of claim; wherein the first solution has a pH of about 6 to about 7.

10. The method of claim 1, wherein the first solution has an oxidative reduction potential of about 88 to about 92 my.

11. The method of claim 1, wherein the second solution has an oxidative reduction potential of about 140 to about 160 mV.

12. The method of claim 1, wherein the first solution of ultrapure water is prepared by carbon filtration, slow sand filtration, reverse osmosis, electro-deionization treatment, ultraviolet light exposure, or a combination thereof.

13. The method of claim 1, wherein the jet openings redirect the ultrapure water by an average of between about 0 to 90 degrees relative to a long axis of the transfer pipe.

14. The method of claim 1, wherein the first solution further comprises one or ore solutes.

15. The method of claim 14, wherein the one or more solutes comprise an ion of an ionizable salt.

16. The method of claim 15, wherein the ion is selected from the group consisting of selected from aluminum ion, ammonium ion, antimony ion, arsenic ion, barium ion, beryllium ion, bismuth ion, boron ion, bromide ion, cadmium ion, calcium ion, cerium ion, cesium cation, chloride ion, chromium ion, cobalt ion, copper ion, dysprosium ion, erbium ion, europium ion, fluoride ion, gadolinium ion, gallium ion, germanium ion, gold ion, hafnium ion, holmium ion, indium ion, iodine ion, iridium ion, iron ion, lanthanum ion, lead ion, lithium ion, lutetium ion, magnesium ion, manganese ion, mercury ion, molybdenum ion, neodymium ion, nickel ion, niobium ion, osmium ion, palladium ion, phosphorus ion, platinum ion, potassium ion, praseodymium ion, rhenium ion, rhodium ion, rubidium ion, ruthenium ion, samarium ion, scandium ion, selenium ion, silicon ion, silver ion, sodium ion, strontium ion, sulfate ion, tantalum ion, tellurium ion, terbium ion, thallium ion, thorium ion, thulium ion, tin ion, titanium ion, tungsten ion, vanadium ion, ytterbium ion, yttrium ion, zinc ion, and zirconium ion.

17. The method of claim 14, wherein the one or more solutes are comprised of:
    (i) potassium chloride, vitamin B6, ferric chloride, magnesium sulfate, sodium chloride, ionic Trace Minerals, kelp, taurine, alfalfa; and sodium borate; or
    (ii) capasaicin, resveratrol, quercetin, vitamin D3, and *Panax ginseng*; or
    (iii) synapta, magnesium chloride, concentrated trace minerals, and sodium benzoate;
or a combination thereof.

* * * * *